United States Patent
Ware et al.

(10) Patent No.: US 10,487,061 B2
(45) Date of Patent: *Nov. 26, 2019

(54) MORPHIC FORMS OF HEXADECYLOXYPROPYL-PHOSPHONATE ESTERS AND METHODS OF SYNTHESIS THEREOF

(71) Applicant: Chimerix, Inc., Durham, NC (US)

(72) Inventors: Roy Wendell Ware, Raleigh, NC (US); Aaron Leigh Downey, Durham, NC (US)

(73) Assignee: Chimerix, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/135,171

(22) Filed: Sep. 19, 2018

(65) Prior Publication Data

US 2019/0016687 A1 Jan. 17, 2019

Related U.S. Application Data

(60) Continuation of application No. 15/828,935, filed on Dec. 1, 2017, now Pat. No. 10,112,909, which is a continuation of application No. 15/160,885, filed on May 20, 2016, now Pat. No. 9,862,687, which is a division of application No. 14/604,334, filed on Jan. 23, 2015, now Pat. No. 9,371,344, which is a continuation of application No. 14/512,335, filed on Oct. 10, 2014, now Pat. No. 8,962,829.

(60) Provisional application No. 61/904,857, filed on Nov. 15, 2013.

(51) Int. Cl.
- C07D 239/47 (2006.01)
- C07F 9/6512 (2006.01)
- C07F 9/53 (2006.01)

(52) U.S. Cl.
CPC .......... *C07D 239/47* (2013.01); *C07F 9/6512* (2013.01); *C07F 9/53* (2013.01)

(58) Field of Classification Search
CPC ............ C07F 9/650911; C07F 9/65742; C07F 9/65125; C07F 9/65121; C07F 9/65122; C07F 9/40; C07F 9/4006
See application file for complete search history.

(56) References Cited

U.S. PATENT DOCUMENTS

| | | | |
|---|---|---|---|
| 5,476,938 A | 12/1995 | Vemishetti et al. | |
| 6,716,825 B2 | 4/2004 | Hostetler et al. | |
| 7,034,014 B2 | 4/2006 | Hostetler et al. | |
| 7,094,772 B2 | 8/2006 | Hostetler et al. | |
| 7,098,197 B2 | 8/2006 | Hostetler et al. | |
| 7,452,898 B2 | 11/2008 | Hostetler et al. | |
| 7,612,072 B2 | 11/2009 | Ferlita et al. | |
| 7,687,480 B2 | 3/2010 | Hostetler et al. | |
| 7,749,983 B2 | 7/2010 | Hostetler et al. | |
| 7,790,703 B2 | 9/2010 | Hostetler et al. | |
| 7,994,143 B2* | 8/2011 | Hostetler | C07F 9/6552 514/43 |
| 8,008,308 B2 | 8/2011 | Hostetler et al. | |
| 8,309,565 B2 | 11/2012 | Hostetler et al. | |
| 8,569,321 B2 | 10/2013 | Ware et al. | |
| 8,614,200 B2 | 12/2013 | Painter et al. | |
| 8,642,577 B2* | 2/2014 | Almond | A61K 31/675 514/410 |
| 8,962,829 B1* | 2/2015 | Ware, Jr. | C07D 239/47 544/243 |
| 9,006,218 B2 | 4/2015 | Almond et al. | |
| 9,303,051 B2* | 4/2016 | Ware | C07F 9/3808 |
| 9,371,344 B2* | 6/2016 | Ware, Jr. | C07D 239/47 |
| 9,862,687 B2* | 1/2018 | Ware, Jr. | C07D 239/47 |
| 10,112,909 B2* | 10/2018 | Ware | C07D 239/47 |
| 2002/0022659 A1 | 2/2002 | Harris et al. | |
| 2002/0025980 A1 | 2/2002 | Katz et al. | |
| 2006/0172974 A1 | 8/2006 | Chen et al. | |
| 2007/0003516 A1 | 1/2007 | Almond et al. | |
| 2007/0003608 A1 | 1/2007 | Almond et al. | |
| 2007/0021430 A1 | 1/2007 | Chen et al. | |
| 2008/0009462 A1 | 1/2008 | Hostetler et al. | |
| 2008/0167477 A1 | 7/2008 | Jetti et al. | |
| 2009/0137613 A1 | 5/2009 | Ceric et al. | |
| 2009/0156545 A1 | 6/2009 | Hostetler et al. | |
| 2009/0286981 A1 | 11/2009 | Vasireddy et al. | |
| 2010/0249056 A1 | 9/2010 | Hostetler et al. | |
| 2010/0292470 A1 | 11/2010 | Galimi | |
| 2011/0009368 A1 | 1/2011 | Dova | |

(Continued)

FOREIGN PATENT DOCUMENTS

| | | |
|---|---|---|
| CN | 1414854 A | 4/2003 |
| CN | 101143879 A | 3/2008 |

(Continued)

OTHER PUBLICATIONS

E.R. Kern et al., 46 Antimicrobial Agents and Chemotherapy 991-995 (2002) (Year: 2002).*
R. Lanier et al., 2 Viruses, 2740-2762 (2010) (Year: 2010).*
Anderson, Practical Process & Research Development 81-111, 114-143, (2000).
Brittain, H.G., "Preparation and Identification of Polymorphs and Solvatomorphs", Preformulation in Solid Dosage Form Development, Boca Raton, FL: CRC Press, Blachére et al., eds. 3.4:229-252 (2008).
Brittain, H.G., "Preparation and Identification of Polymorphs and Solvatomorphs", Preformulation in Solid Dosage Form Development, Boca Raton, FL: CRC Press, Adeyeye et al., eds. 3.3:185-228 (2008).

(Continued)

*Primary Examiner* — Alexander R Pagano
(74) *Attorney, Agent, or Firm* — Cooley LLP; Ivor R. Elrifi; Heidi A. Erlacher

(57) ABSTRACT

The disclosure describes methods of synthesis of phosphonate ester compounds. The methods according to the disclosure allow for large-scale preparation of phosphonate ester compounds having high purity and stability. Also disclosed are morphic forms of phosphonate ester compounds.

31 Claims, 30 Drawing Sheets

(56) References Cited

U.S. PATENT DOCUMENTS

| | | | |
|---|---|---|---|
| 2011/0015149 A1* | 1/2011 | Almond | A61K 31/675 514/51 |
| 2011/0263536 A1 | 10/2011 | Lanier et al. | |
| 2011/0319422 A1 | 12/2011 | Blumberg et al. | |
| 2012/0010170 A1* | 1/2012 | Painter | A61K 9/0053 514/81 |
| 2012/0058976 A1 | 3/2012 | Ware et al. | |
| 2012/0164104 A1* | 6/2012 | Lanier | C07F 9/65586 424/85.5 |
| 2012/0165295 A1* | 6/2012 | Painter | A61K 9/0048 514/86 |
| 2013/0035313 A1 | 2/2013 | Almond et al. | |
| 2013/0072458 A1* | 3/2013 | Painter | A61K 31/675 514/81 |
| 2014/0011769 A1* | 1/2014 | Lanier | A61K 31/675 514/81 |
| 2014/0046085 A1 | 2/2014 | Ware et al. | |
| 2014/0121186 A1 | 5/2014 | Painter et al. | |
| 2014/0303092 A1* | 10/2014 | Painter | A61K 31/675 514/20.5 |
| 2015/0087619 A1* | 3/2015 | Painter, Jr. | A61K 31/675 514/86 |
| 2015/0203519 A1 | 7/2015 | Almond et al. | |
| 2015/0210724 A1 | 7/2015 | Ware et al. | |
| 2015/0329575 A1 | 11/2015 | Ware et al. | |
| 2016/0264531 A1 | 9/2016 | Ware et al. | |
| 2016/0303147 A1* | 10/2016 | Painter | A61K 9/0053 |
| 2017/0029451 A1 | 2/2017 | Ware et al. | |
| 2017/0368082 A1* | 12/2017 | Ware | A61K 9/0019 |
| 2018/0086721 A1 | 3/2018 | Ware et al. | |

FOREIGN PATENT DOCUMENTS

| | | | |
|---|---|---|---|
| JP | H06-503807 | 4/1994 | |
| WO | WO 2001/039724 A2 | 6/2001 | |
| WO | WO-0139724 A2 * | 6/2001 | C07F 9/3873 |
| WO | WO 2005/087788 A2 | 9/2005 | |
| WO | WO 2006/014429 A2 | 2/2006 | |
| WO | WO 2006/110655 A2 | 10/2006 | |
| WO | WO 2006/110656 A2 | 10/2006 | |
| WO | WO-2006110655 A2 * | 10/2006 | A61K 31/675 |
| WO | WO 2007/130783 A2 | 11/2007 | |
| WO | WO 2008/133966 A1 | 11/2008 | |
| WO | WO 2011/011519 A1 | 1/2011 | |
| WO | WO 2011/017253 A1 | 2/2011 | |
| WO | WO 2011/053812 A1 | 5/2011 | |

OTHER PUBLICATIONS

Brittain, H.G., "Theory and Principles of Polymorphic Systems", Poylmorphism in Pharmaceutical Solids, 2nd Ed., Drugs and the Pharmaceutical Sciences, 192(1):1-23 (H.G. Brittain ed., 2nd ed., 2009).

Brodfuehrer et al., 35 Tetrahedron Letters, 3243-3246 (1994).

Bronson et al., 9 Nucleosides & Nucleotides, 745-769 (1990).

Byrn et al. "Pharmaceutical Solids: A Strategic Approach to Regulatory Considerations" Pharmaceutical Research, 12(7) p. 945-954 (1995).

Cans, P.W., "Classical Methods of Preparation of Polymorphs and Alternative Solid Forms", Poylmorphism in Pharmaceutical Solids, 2nd Ed., Drugs and the Pharmaceutical Sciences, Informa Healthcare USA, Inc., New York, NY, 4:76-138 (H.G. Brittain ed., 2nd ed., 2009).

Caira, M.R., "Crystalline Polymorphism of Organic Compounds", Topics in Current Chemistry, 198:163-208 (1998).

Grant, "Polymorphism in Pharmaceutical Solids" edited by Brittain et al., (Chapter 1), p. 1-33 (1999).

Guillory, J.K.,"Generation of Polymorphs, Hydrates, Solvates, and Amorphous Solids", Poylmorphism in Pharmaceutical Solids, 183-220 (H.G. Brittain, ed. 1999).

Kern, E.R. et al. "Enhanced Inhibition of Orthopoxvirus Replication In Vitro by Alkoxyalkyl Esters of Cidofovir and Cyclic Cidofovir", Antimicrob. Agents Chemo., 46(4):991-995 (2002).

Lanier R. "Development of CMX001 for the Treatment of Poxvirus Infections", Viruses, 2010, vol. 2, No. 12, p. 2740-2762.

Leonard, J. et al., "Working Up The Reaction" and "Purification", Advanced Practical Organic Chemistry, 10-11:177-226 (2nd ed., 1995).

Mirozoeva S. et al. J. Med. Chem. 45, 563-566 (2002).

Morissette, S.L. et al. "High-Throughput Crystallization: Polymorphs, Salts, Co-Crystals and Solvates of Pharmaceutical Solids", Adv. Drug Deliv. Rev. 56:275-300 (2004).

Oxford Dictionary of Chemistry 169 (John Daintith ed., 6th ed., 2008).

Painter et al. "First Pharmacokinetic and Safety Study in Humans of the Novel Lipid Antiviral Conjugate CMX001, a Broad-Spectrum Oral Drug Active against Double-Stranded DNA Viruses", Antimicrobial Agents and Chemotherapy, 2012, vol. 56, No. 5, p. 2726-2734.

Painter et al. et al., 33 Drugs of the Future, 655-661 (2008).

Painter et al. et al., 22 Trends in Biotechnology, 423-427 (2004).

Price, S.L., "Computational Methodologies: Toward Crystal Structure and Polymorph Prediction", Poylmorphism in Pharmaceutical Solids, 2nd Ed., Drugs and the Pharmaceutical Sciences, Informa Healthcare USA, Inc., New York, NY, 3:52-75 (H.G. Brittain ed., 2nd ed., 2009).

Prichard M. et al., 52 Antimicrobial Agents and Chemotherapy, 4326-4330 (2008).

Reznikov, A.N. et al., "Synthesis of Adamantylalkyl Tosyloxymethylphosphonates", Russian Journal of General Chemistry, 79(8):1755-1757 (2009).

Solid State Characterization of Pharmaceuticals 4 73-491, 490 (R.A. Storey et al., eds., 2011).

Toth et al., 105 PNAS, 7293-7297 (2008).

Valiaeva, N. et al., "Synthesis and antiviral evaluation of alkoxyalkyl esters of acyclic purine and pyrimidine nucleoside phosphonates against HIV-1 in vitro", Antiviral Research, 72(1):10-19 (2006).

Vrbkova, S. et al., "Synthesis of phosphonomethoxyethyl 1,3-bis(phosphonomethoxy) propan-2-yl lipophilic esters of acyclic nucleoside phosphonates", Tetrahedron, 63(46):11391-11398 (2007).

Vippagunta, S.R. et al., "Crystalline Solids", Adv. Drug Deliv. Rev., 48:3-26 (2001).

Yang, L. and Guanhua, D. *Polymorphic Drugs*, People's Medical Publishing House, Co., Ltd., 1st Edition, 2009. (English summary attached).

* cited by examiner

| CMX001-069 | | | | |
|---|---|---|---|---|
| Peak# | Ret. Time | RRT | Calculated % | Reported % |
| 1 | 7.264 | 0.75 | -0.017 | 0 |
| 2 | 8.771 | 0.91 | 0.041 | 0.04 |
| 3 | 9.654 | 1 | | |
| 4 | 10.459 | 1.08 | 0.168 | 0.17 |
| 5 | 11.212 | 1.16 | 0.097 | 0.10 |
| 6 | 14.367 | 1.49 | 0.094 | 0.09 |
| 7 | 14.95 | 1.55 | 0.007 | 0.01 |
| 8 | 15.536 | 1.61 | 0.544 | 0.54 |
| 9 | 16.145 | 1.67 | 0.038 | 0.04 |
| 10 | 16.648 | 1.72 | 0.514 | 0.51 |
| | | | Impurities | 1.5 |
| | | | Purity | 98.5 |

| CMX001-092 | | | | |
|---|---|---|---|---|
| Peak# | Ret. Time | RRT | Calculated % | Reported % |
| 1 | 8.779 | 0.91248311 | -0.031 | 0 |
| 2 | 9.621 | 1 | | |
| 3 | 10.452 | 1.086373558 | -0.016 | 0 |
| 4 | 11.212 | 1.165367425 | 0.000 | 0 |
| 5 | 15.536 | 1.614800956 | 0.399 | 0.40 |
| 6 | 16.145 | 1.67809999 | -0.034 | 0 |
| 7 | 16.658 | 1.73142085 | 0.060 | 0.06 |
| | | | Impurities | 0.5 |
| | | | Purity | 99.5 |

| CMX001-097 | | | | |
|---|---|---|---|---|
| Peak# | RT | RRT | Calculated % | Reported %Impurity |
| 1 | 8.315 | 0.84 | -0.10 | 0 |
| 2 | 9.038 | 0.91 | -0.09 | 0 |
| 3 | 9.879 | 1 | | |
| 4 | 11.479 | 1.16 | -0.07 | 0 |
| | | | Impurities | 0.0 |
| | | | Purity | 100.0 |

| LV-345-21-H | | | | |
|---|---|---|---|---|
| Peak# | Ret. Time | RRT | Calculated % | Reported %Impurity |
| 1 | 9.754 | | | |
| 2 | 11.515 | 1.18 | 0.0492 | 0.0 |
| | | | Impurities | 0.0 |
| | | | Purity | 100.0 |

MORPHIC FORMS OF HEXADECYLOXYPROPYL-PHOSPHONATE ESTERS AND METHODS OF SYNTHESIS THEREOF

RELATED APPLICATIONS

This application is a continuation of U.S. patent application Ser. No. 15/828,935, filed Dec. 1, 2017 (now allowed), which is a continuation of U.S. patent application Ser. No. 15/160,885, filed May 20, 2016, and issued as U.S. Pat. No. 9,862,687 on Jan. 9, 2018, which is a divisional application of U.S. patent application Ser. No. 14/604,334, filed Jan. 23, 2015, and issued as U.S. Pat. No. 9,371,344, on Jun. 21, 2016, which is a continuation of U.S. patent application Ser. No. 14/512,335, filed Oct. 10, 2014 and issued as U.S. Pat. No. 8,962,829 on Feb. 24, 2015, which claims priority to U.S. Provisional Application No. 61/904,857, filed Nov. 15, 2013, the entire content of which is incorporated herein by reference in its entirety.

TECHNICAL FIELD

This disclosure relates to solid crystalline forms of Phosphonic acid, [[(S)-2-(4-amino-2-oxo-1(2H)-pyrimidinyl)-1-(hydroxymethyl) ethoxy]methyl]mono[3-(hexadecyloxy)propyl] ester, and related compositions and methods. The methods provided in the present disclosure provide synthesis of morphic forms of Compound 1 with high purity, high yield, and high stability, and crystals thereof.

BACKGROUND OF THE INVENTION

In the pharmaceutical drug development there is a need for reproducible manufacturing methods for obtaining pharmaceutically active ingredients in chemically and morphologically pure form. Obtaining the pharmaceutically active ingredient in homogeneous solid state is a precondition for complying with the requirements of the industrial manufacture of finished dosage forms. Solid forms of the same active ingredient having different morphology may exhibit significant differences in the rate of dissolution, bioavailability and chemical stability. From the viewpoint of industrial chemical and pharmaceutical technology, it is important, therefore, that different solid forms of an active ingredient can possess significantly different properties with regard to the operations of the technology, e.g. rate of filtration or drying, solubility, behavior during tableting. The properties mentioned here have a direct impact on the efficiency, economy, reproducibility and complexity of the industrial manufacturing process and may result in a morphologically homogeneous product.

It is generally accepted that crystalline forms of pharmaceutically active ingredients possess improved chemical stability as compared to the amorphous form. Due to the different decomposition processes during the manufacture and shelf-life of the finished dosage form, this difference in stability is of general importance. Therefore, manufacturers of medicinal products prefer to use crystalline forms of the active ingredients during pharmaceutical development.

The polymorphism of a pharmaceutically active ingredient can be exploited in several ways. For example, using a crystalline form having suitable stability and impurity profile (purity) for the manufacture of a finished dosage form is of paramount importance. It is also significant that a crystalline active ingredient should have appropriate properties for manipulations of large-scale manufacturing and pharmaceutical technology on an industrial scale. However, different properties of polymorphs, e.g. dissolution rate, particle size etc. can also be exploited during the design of different finished dosage forms. A polymorph having lower dissolution rate may contribute to the properties of a delayed release dosage form, while the skilled person may appreciate a form having higher solubility or higher dissolution rate during the formulation of an immediate release dosage form. Moreover, it is not routine practice in the art to make a specific polymorph. The present invention is directed at providing unique polymorphs of Compound 1 with desirable features.

SUMMARY OF THE INVENTION

The present disclosure, in part, provides a method for manufacturing industrial scale solid forms (e.g. crystalline forms) of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1). In some embodiments, the present invention provides methods of synthesizing Compound to provide it in high purity and high yield. In some embodiments, the crystalline forms of Compound 1 synthesized by the method of the present disclosure are stable as compared to the amorphous form.

It is an object of this disclosure to provide novel process for the preparation of solid forms (e.g., crystalline forms) of phosphonic acid, [[(S)-2-(4-amino-2-oxo-1(2H)-pyrimidinyl)-1-(hydroxymethyl) ethoxy]methyl]mono[3-(hexadecyloxy)propyl] ester ("Compound 1") in good yield, in large amounts, and with desired purity. Provided herein are novel solid forms (e.g., crystalline forms) of phosphonic acid, [[(S)-2-(4-amino-2-oxo-1(2H)-pyrimidinyl)-1-(hydroxymethyl) ethoxy]methyl]mono[3-(hexadecyloxy)propyl] ester ("Compound 1").

One embodiment is directed to polymorph or morphic Form II (the terms "polymorph" or "morphic Form" are used interchangeably in this disclosure). In some embodiments, a composition comprising the morphic Form II of the present disclosure is substantially free of impurities, i.e., not a sufficient amount of impurities are present in the sample of Form II. In some embodiments, a composition comprising the morphic Form II is substantially free of amorphous Compound 1. The embodiments of the present disclosure also provide that the Form II is substantially free of hydrate form. In some embodiments, a composition comprising Form II is anhydrous.

In some embodiments, a composition comprising the morphic Form II of the present disclosure is less than about 3 mg/mL soluble in 1:1 methanol:water ratio at room temperature and less than about 14 mg/mL soluble at about 63° C. A composition comprising morphic Form II of the present disclosure can have an X-ray diffraction pattern including prominent peaks at about 2.81 and about 5.63 degrees 2Θ.

In one embodiment, a composition comprising the morphic Form II of the compound of the present embodiment is characterized by an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and/or have a DSC Thermogram substantially similar to that set forth in FIG. 4, FIG. 15, FIG. 16, or FIGS. 22-24.

One embodiment of the present disclosure provides a morphic Form II of a compound having Formula II or III characterized by an X-ray diffraction pattern with two or more (e.g., three or more, four or more, five or more, six or more, seven or more, eight or more, nine or more, or ten or more) peaks expressed in degrees 2Θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61, or having an X-ray diffraction pattern substantially similar to that set forth in FIG. 1, FIG. 7, FIG. 13, FIG. 14, FIG. 20, FIG. 21, or FIG. 25. In one embodiment, a composition comprising the morphic Form II has indexing substantially similar to that set forth in FIG. 2 and/or a DSC Thermogram substantially similar to that set forth in FIG. 4, FIG. 15, FIG. 16 or FIGS. 22-24. In some embodiments, a composition comprising the morphic Form II is characterized by $^1$H NMR substantially similar to that set forth in FIG. 6.

The present disclosure provides, morphic Form II of a compound of Formula II or III (or a pharmaceutically acceptable salt thereof) characterized by an X-ray diffraction pattern with two or more (e.g., three or more, four or more, five or more, six or more, seven or more, eight or more, nine or more, or ten or more) peaks expressed in degrees 2Θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61, or having an X-ray diffraction pattern substantially similar to that set forth in FIG. 1, FIG. 7, FIG. 13, FIG. 14, FIG. 20, FIG. 21, or FIG. 25, and/or characterized by $^1$H NMR substantially similar to that set forth in FIG. 6, administered at a dose of about 100 mg twice a week or at a dose of about 200 mg once a week. In one embodiment, a composition comprising the morphic Form II having indexing substantially similar to that set forth in FIG. 2 and/or a DSC Thermogram substantially similar to that set forth in FIG. 4, FIG. 15, FIG. 16 or FIGS. 22-24 is administered at a dose of about 100 mg twice a week or at a dose of about 200 mg once a week.

The present disclosure provides morphic Form II of a compound of Formula II or III (or a pharmaceutically acceptable salt thereof) characterized by an X-ray diffraction pattern with two or more (e.g., three or more, four or more, five or more, six or more, seven or more, eight or more, nine or more, or ten or more) peaks expressed in degrees 2Θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61, or having an X-ray diffraction pattern substantially similar to that set forth in FIG. 1, FIG. 7, FIG. 13, FIG. 14, FIG. 20, FIG. 21, or FIG. 25, and/or characterized by $^1$H NMR substantially similar to that set forth in FIG. 6, administered at a dose of about 1-4 mg/kg (e.g., about 1.0-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg).

In some embodiments, a composition comprising the morphic Form II having indexing substantially similar to that set forth in FIG. 2 and/or a DSC Thermogram substantially similar to that set forth in FIG. 4, FIG. 15, FIG. 16 or FIGS. 22-24 is administered at a dose of about 1-4 mg/kg (e.g., about 1.0-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg).

The present disclosure provides, morphic Form H of a compound of Formula II or III (or a pharmaceutically acceptable salt thereof) characterized by an X-ray diffraction pattern substantially similar to that set forth in FIG. 18, administered at a dose of about 100 mg twice a week or at a dose of about 200 mg once a week. In one embodiment, a composition comprising the morphic Form H having indexing substantially similar to that set forth in FIG. 3 and/or a DSC Thermogram substantially similar to that set forth in FIG. 17 is administered at a dose of about 100 mg twice a week or at a dose of about 200 mg once a week.

In some embodiments, a composition comprising the morphic Form H is characterized by an X-ray diffraction pattern substantially similar to that set forth in FIG. 18, having indexing substantially similar to that set forth in FIG. 3, and/or a DSC Thermogram substantially similar to that set forth in FIG. 17 is administered at a dose of about 1-4 mg/kg (e.g., about 1.0-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg).

In some embodiments, Form II is distinguished from Form H. For instance, FIG. 25 shows a comparison of the X-ray powder diffraction spectra for two samples of Form II (top two spectra) and one sample of Form H (bottom sample). As seen from the comparison, Form II is different from Form H in that it has significant peaks at about, for instance, 24.8° 2Θ and 22.9° 2Θ. In contrast, in some embodiments Form II does not have substantial peaks that are seen in Form H, for instance at about 24.1° 2Θ, 21.5° 2Θ, 20.9° 2Θ, and 12.6° 2Θ.

In some embodiments the present disclosure provides Compound 1 Form II (or a pharmaceutically acceptable salt thereof) formulated as a pharmaceutical composition (see Tables 11 and 12). In one embodiment, Compound 1 Form II (or a pharmaceutically acceptable salt thereof) is formulated as a tablet of formulation 1 (see Table 11). In another embodiment, Compound 1 Form II (or a pharmaceutically acceptable salt thereof) is formulated as a tablet of formulation 2 (see Table 11). In yet another embodiment, Compound 1 Form II (or a pharmaceutically acceptable salt thereof) is formulated as a suspension of formulation 3 (see Table 12). In another embodiment, Compound 1 Form II (or a pharmaceutically acceptable salt thereof) is formulated as a suspension of formulation 4 (see Table 12).

A composition comprising morphic Form II of the compound according to the present disclosure can be produced by a purification process comprising recrystallizing a preparation of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1) from methanol.

In some preferred embodiments, the Compound 1 produced by the process set forth herein is purified by a series of five distinct recrystallizations. For instance, Compound 1 can first be purified by three distinct, sequential recrystallizations from methanol. Then, Compound 1 can be recrystallized from n-heptane and methanol. In some preferred embodiments, the methanol recrystallizations remove a different set of impurities than the n-heptane/methanol recrystallization. Finally, Compound 1 can be purified again from methanol. In some preferred embodiments, the final recrystallization from methanol is carried out with seeding with an amount of morphic Form II and proceeds with a slow, controlled cooling that ensures the formation of morphic Form II.

The present disclosure also provides a method for synthesizing a composition comprising the morphic Form II of Compound 1. The method of synthesis of a composition comprising the morphic Form II of the present disclosure involves the following steps:
  a. heating a mixture of (S)—N$^1$-[(2-hydroxy-3-triphenylmethoxy)propyl]cytosine (Compound 2), P-[[[4-methylphenyl)sulfonyl]oxy]methyl]-, mono[3-(hexadecyloxy)propyl]ester, sodium salt (Compound 4), magnesium tert-butoxide, and dimethylformamide (DMF);
  b. cooling and adding isopropyl acetate;
  c. washing sequentially with HCl solution and NaCl solution;
  d. diluting the concentrate with methanol and forming a mixture containing phosphonic acid, [[(S)-2-(4-amino-2-oxo-1(2H)-pyrimidinyl)-1-(hydroxymethyl)-2-(triphenylmethoxy)ethyl]methyl]mono[3-(hexadecyloxy)propyl]ester (Compound 3);
  e. diluting the concentrate containing Compound 3 in methanol;
  f. adding HCl gas and maintaining temperature below about 20° C.;
  g. filtering to remove impurities and preparing slurry in acetone;
  h. filtering the slurry and washing with acetone;
  i. recrystallizing from methanol;
  j. recrystallizing a second time from methanol;
  k. recrystallizing a third time from methanol;
  l. recrystallizing from n-heptane and methanol;
  m. dissolving crude product in methanol;
  n. adding to the solution a seed stock of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1) and stirring;
  o. cooling, filtering, and washing the solution with methanol and drying;
thereby synthesizing morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1).

The present disclosure provides Form II synthesized is more than or equal to about 91% wt/wt, more than or equal to about 95% wt/wt, or more than or equal to about 99% wt/wt pure.

The present disclosure also provides a method for synthesizing a composition comprising the morphic Form II of Compound 1. The method of synthesis of a composition comprising the morphic Form II of the present disclosure involves the following steps:
  heating a mixture of (S)—N$^1$-[(2-hydroxy-3-triphenylmethoxy)propyl]cytosine (Compound 2), P-[[[4-methylphenyl)sulfonyl]oxy]methyl]-, mono[3-(hexadecyloxy)propyl] ester, sodium salt (Compound 4), magnesium tert-butoxide, and dimethylformamide (DMF) at between about 75-85° C. for about 3 hours;
  a. cooling the mixture to about 25-35° C. and adding isopropyl acetate;
  b. further cooling the solution to about 15-25° C. and washing sequentially with HCl solution and NaCl solution;
  c. removing isopropyl acetate by vacuum distilling the organic phase thereby forming a concentrate;
  d. diluting the concentrate with methanol and further removing isopropyl acetate thereby re-concentrating and forming a mixture containing phosphonic acid, [[(S)-2-(4-amino-2-oxo-1(2H)-pyrimidinyl)-1-(hydroxymethyl)-2-(triphenylmethoxy)ethyl]methyl]mono[3-(hexadecyloxy)propyl]ester (Compound 3);
  e. diluting the concentrate containing Compound 3 in methanol;
  f. adding HCl gas at a rate that maintains the temperature between about −5 and 15° C.;
  g. maintaining the reaction about 10-20° C. for 2 hours before filtering to remove solid impurities;
  h. diluting the filtrate with water and adjusting pH to about 2.3-2.7 with NaOH;
  i. filtering the solids and washing the solids with water before preparing a slurry in acetone at about 35-45° C. for about 1 hour;
  j. filtering the slurry and washing with acetone;
  k. drying the acetone washed crude product at a temperature of equal to or less than about 40° C. for about 12 hours;
  l. heating the crude product at about 60-70° C. in methanol
  m. polish filtering, cooling to about 58-62° C., stirring for one hour, cooling to about 48-52° C. for about six hours, then to about 17-23° C. for two hours, filtering, and then washing with methanol;
  n. repeating steps l-m twice or more;
  o. heating the product in methanol at about 64° C. and slowly adding n-heptane over 40 min while keeping the temperature above 50° C.;
  p. holding at a temperature about 55° C. for 30 min and cooling to 40° C. over a 6 h period;
  q. stirring at 40° C. for 2 h, then cooling to 20° C. over six hours;
  r. stirring for 2 h at 20° C.
  s. filtering and washing with n-heptane and methanol and drying under vacuum;
  t. dissolving solids in methanol before cooling to about 59-61° C. and then stirring for about 20 minutes;
  u. adding to the solution a seed stock of phosphonic acid, [[(S)-2-(4-amino-2-oxo-1(2H)-pyrimidinyl)-1-(hydroxymethyl) ethoxy]methyl]mono[3-(hexadecyloxy) propyl] ester (Compound 1) and stirring for two hours;

v. cooling the solution to about 47-53° C. by stirring for about eight hours, and then stirring for about two hours;

w. cooling the stirred solution further to about 17-23° C. over about six hours, and further stirring for about two hours;

x. filtering and washing the solution with methanol;

y. drying at a temperature of equal to or less than about 40° C. for about twenty-four hours; and thereby synthesizing morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1).

The present disclosure provides a method of preparing Form II of Compound 1, comprising the step of combining (S)—$N^1$-[(2-hydroxy-3-triphenylmethoxy)propyl]cytosine (Compound 2), P-[[[4-methylphenyl)sulfonyl]oxy]methyl]-, mono[3-(hexadecyloxy)propyl]ester, sodium salt (Compound 4) with magnesium tert-butoxide, and dimethylformamide (DMF).

The present disclosure provides a method for synthesizing a crystalline morphic Form II of Compound 1, by performing a crystallization step. For instance, a solution (e.g., a methanol solution) comprising Compound 1 can be seeded with about 0.5%, about 3%, or about 7% of seed of the phosphonic acid (e.g., the seed can be Form I or Form II of Compound 1). The solution can then be allowed to crystallize. In some embodiments, the crystalline morphic form II of Compound 1 is crystallized with slow stirring or agitation during the crystallization process. In one embodiment, the rate of stirring affects the type of morphic form produced. In another embodiment, the rate of stirring does not affect the type of morphic form produced. The embodiments provide morphic Form II crystallization by a process comprising methanol. The embodiments further provide crystallization process for forming morphic Form II by seeding with Form II or Form I of the phosphonic acid. Additionally, in some embodiments, morphic Form II is provided by cooling the methanol slowly. For instance, in some preferred embodiments, Compound 1 can be dissolved in methanol at about 65° C. (e.g., about reflux temperature) and held at about 65° C. for 1 hour then cooled to 61° C. before seeding with morphic Form II. The contents can be stirred at 60° C. for 1 hour and cooled to 50° C. over a period of eight hours. The contents can be held at 50° C. for two hours, and then further cooled from 50° C. to 20° C. for at least six hours (e.g., overnight) and stirred at 20° C. for at least two hours before filtering. In some preferred embodiments, the slow cooling protocol can help ensure the formation of Form II.

In one embodiment, the present disclosure provides production of Form II with starting material about 100 Kg without seeding. The process of production of Form II without seeding involves quick cool-down methanol recrystallization, which results in smaller particle size compared to the particle size of Form II when the process includes seeding and slow cool-down.

In some embodiments, a composition comprising morphic Form II synthesized following the method of the present disclosure is substantially free of impurities. In some embodiments, a composition comprising morphic Form II synthesized following the method of the present embodiment is more than or equal to about 99% wt/wt pure. In some preferred embodiments, the substantial (e.g., about 100% pure) purity is the result of a series of recrystallizations that can remove a host of impurities. In some embodiments, although any particular recrystallization technique can remove impurities, certain recrystallizations can be more effective at removing certain specific impurities compared with other recrystallizations. For instance, in some embodiments, three initial recrystallizations from methanol remove certain impurities. Next, in some embodiments, a recrystallization from n-heptane and methanol can remove additional (e.g., different) impurities remaining in Compound 1 that were not fully removed by the recrystallizations from methanol alone. A final recrystallization from methanol with seeding and a slow cool-down can remove additional trace impurities and produce morphic Form II of Compound 1.

In some embodiments, a composition comprising morphic Form II synthesized by the method of the present disclosure can be a hydrate. In some embodiments, a composition comprising the morphic Form II of the compound of the present disclosure is not a hydrate. In some embodiments, a composition comprising the morphic Form II synthesized by the method of the present disclosure is substantially free of the hydrate form. In some embodiments, a composition comprising the morphic form II partially hydrated or a partial hydrate.

In some embodiments, a composition comprising morphic Form II of the present disclosure partially converts to a hydrate form after being exposed to about 43% RH for about 12 days. In some embodiments, a composition comprising The morphic Form II of the present embodiment shows a minor endotherm at about 41-43° C. (peak max) followed by overlapping major endotherms at about 90 and about 95° C. (peak max) in a DSC thermogram. The final endotherm of a composition comprising the morphic Form II of the present embodiment has an onset at about 196° C.

The present disclosure provides a method of synthesis of a morphic Form II of a compound having Formula II or III characterized by an X-ray diffraction pattern with two or more (e.g., three or more, four or more, five or more, six or more, seven or more, eight or more, nine or more, or ten or more) peaks expressed in degrees 2Θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61.

The present disclosure further provides a method of synthesis of a morphic Form II of a compound having Formula II or III characterized by an X-ray diffraction pattern substantially similar to that set forth in FIG. 1, FIG. 7, FIG. 13, FIG. 14, FIG. 20, FIG. 21, or FIG. 25.

Some embodiments of the present disclosure provides a method of synthesis of a morphic Form II of a compound having Formula II or III characterized by a DSC Thermogram substantially similar to that set forth in FIG. 4, FIG. 15, or FIG. 16.

The present disclosure provides a Form II of a compound of Formula II or III in a stable crystalline form.

The present disclosure provides a method of synthesizing (S)—$N^1$-[(2-hydroxy-3-triphenylmethoxy)propyl] cytosine (Compound 2), including the following steps:

a. heating a mixture of (S)-trityl glycidyl ether, cytosine, potassium carbonate, and N, N-dimethylformamide (DMF);

b. cooling the reaction mixture and quenching with toluene;

c. cooling the resulting slurry of step b., filtering, washing with toluene;

d. slurrying the solids in toluene, filtering, and then washing with acetone;

e. triturating the solids in water/acetone, filtering, and washing with and suspending in acetone;

f. optionally repeating steps d-e to remove residual cytosine and process-related impurities; and g. drying the filter cake in vacuo, thereby yielding (S)—N$^1$-[(2-hydroxy-3-triphenylmethoxy)propyl] cytosine (Compound 2).

In one embodiment, HPLC (AUC) purity of the synthesized compound is equal to or greater than 91% wt/wt, equal to or greater than 91% wt/wt, or equal to or greater than 99% wt/wt.

The present disclosure also provides a method of synthesizing (S)—N$^1$-[(2-hydroxy-3-triphenylmethoxy)propyl] cytosine (Compound 2), including the following steps:

a. heating a mixture of (S)-trityl glycidyl ether, cytosine, potassium carbonate, and N, N-dimethylformamide (DMF) at about 85-95° C. for about 9 hours;

b. cooling the reaction mixture of step a. to about 66-70° C. and quenching with toluene;

c. cooling the resulting slurry of step b. to about −10 to 5° C., filtering, washing with toluene;

d. slurrying the solids in toluene (168.8 kg) at about 15-25° C., filtering, and then washing with acetone;

e. triturating the solids in water/acetone (90.0 kg/54.0 kg) at about 17-22° C., filtering, and washing with acetone (36.0 kg);

f. suspending filter cake of the filtrate in acetone (178.9 kg) and heated at approximately about 35-45° C. for about 3 hours, filtered, and washed with acetone (36.0 kg).

g. The washes and triturations are optionally repeated as needed to remove residual cytosine and process-related impurities. The cake is dried in vacuo at a temperature equal to or less than about 40° C. for about 12 hours to yield about 45.0 kg (about 65.0%) of Compound 2. HPLC (AUC) purity of the synthesized compound is equal to or greater than 99%.

A number of unique features and advantages set forth in the present disclosure will become apparent to one of skill in the art and are elaborated in the Detailed Description below. A first advantage of the present invention is increased purity of the parent compound, Compound 1. It is readily understood in the chemical and pharmaceutical arts that purity is of utmost importance when characterizing compounds and dosing them for use as pharmaceutical agents. In some preferred embodiments, the current technology provides for five distinct recrystallizations of Compound 1. In some preferred embodiments, the first three recrystallizations are from methanol and are used to remove certain impurities (e.g., Compounds A and B, below) from Compound 1. In some preferred embodiments, a fourth recrystallization (e.g., of Compound 1) from n-heptane and methanol is employed to remove other impurities (e.g., Compounds C and D, below) that remain after the initial three methanol recrystallizations. Accordingly, the present technology provides a system of using distinct and orthogonal purification methods to effectively remove impurities in Compound 1 and to arrive at a composition of Compound 1 that is substantially (e.g., >99% or >99.9%) pure.

A second advantage of the present invention is the ability to generate a specific polymorph of Compound 1 for use in pharmaceutical manufacturing (e.g., commercial pharmaceutical manufacturing). In some preferred embodiments, the fifth recrystallization (e.g., from methanol with a slow cooling and seeding with Form II) can produce Form II reliably and consistently. A skilled artisan will readily recognize that a given compound (e.g., Compound 1) can exist as a variety of different polymorphs. These polymorphs can have significantly different physical properties such as density, solubility, and even chemical reactivity. The heterogeneity between different polymorphs of the same compound can confuse efforts to reliably provide accurate and precise dosages of a given pharmaceutical agent (e.g., Compound 1). For instance, if two different polymorphs of the same compound have different densities, it can be difficult to formulate a pharmaceutical composition comprising that compound that reliably has the same amount, on a molar basis, of the compound itself. Similarly, if different polymorphs have different solubility profiles, they can act differently in the body (e.g., different polymorphs may dissolve faster or slower in the blood). This can complicate efforts to reliably provide, for example, an immediate-release or an extended release dosage form. In other words, polymorphism can be responsible for inconsistencies encountered in the performance of different pharmaceutical agents. See, e.g., Caira, M. R. *Crystalline Polymorphism in Organic Compounds*. Accordingly, a polymorph of a given compound (e.g., Compound 1) can have unique properties that are not inherent in the compound (e.g., Compound 1) itself.

Additionally, it is not routine practice to make a specific polymorph. Indeed, in some cases it can be unpredictable and/or unreliable to arrive at a specific polymorph and the process for producing them can fail to generate them consistently or reliably. See *Polymorphism in Pharmaceutical Solids*, 2nd Ed., Drugs and the Pharmaceutical Sciences (2009), Informa Healthcare USA, Inc., New York, N.Y., Chapter 3, page 52, Introduction and Chapter 4, page 77, first full paragraph and page 87, first full paragraph.

The present invention provides ways to arrive at a specific polymorph (i.e., Form II of Compound 1) consistently and reliably. In some preferred embodiments, Form II is generated by seeding the final recrystallization from methanol with an appropriate amount of a seed crystal of Form II. Also, in some preferred embodiments, the recrystallization proceeds with a slow cooling ramp to ensure the formation of morphic Form II of compound 1. In some preferred embodiments, the combination of seeding with morphic Form II and a slow cool-down procedure can reliably and predictably ensure the formation of morphic form II from the final methanol recrystallization.

In some embodiments, the compound of Formula II or III (e.g., Compound 1) can be in amorphous form.

In one or more aspects, the present invention provides morphic Form II of phosphonic acid, [[(S)-2-(4-amino-2-oxo-1(2H)-pyrimidinyl)-1-(hydroxymethyl) ethoxy]methyl] mono[3-(hexadecyloxy)propyl] ester (Compound 1).

Additional features and advantages of the current technology such as improved yield of the process and a reduction in time for synthesizing Compound 1 will also be apparent to a skilled artisan.

Unless otherwise defined, all technical and scientific terms used herein have the same meaning as commonly understood by one of ordinary skill in the art to which this invention belongs. In the case of conflict, the present specification, including definitions, will control. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In addition, the materials, methods, and examples are illustrative only and are not intended to be limiting.

BRIEF DESCRIPTION OF THE FIGURES

Other features and advantages of the invention will be apparent from the following detailed description and claims.

DETAILED DESCRIPTION OF THE INVENTION

Figure 1:
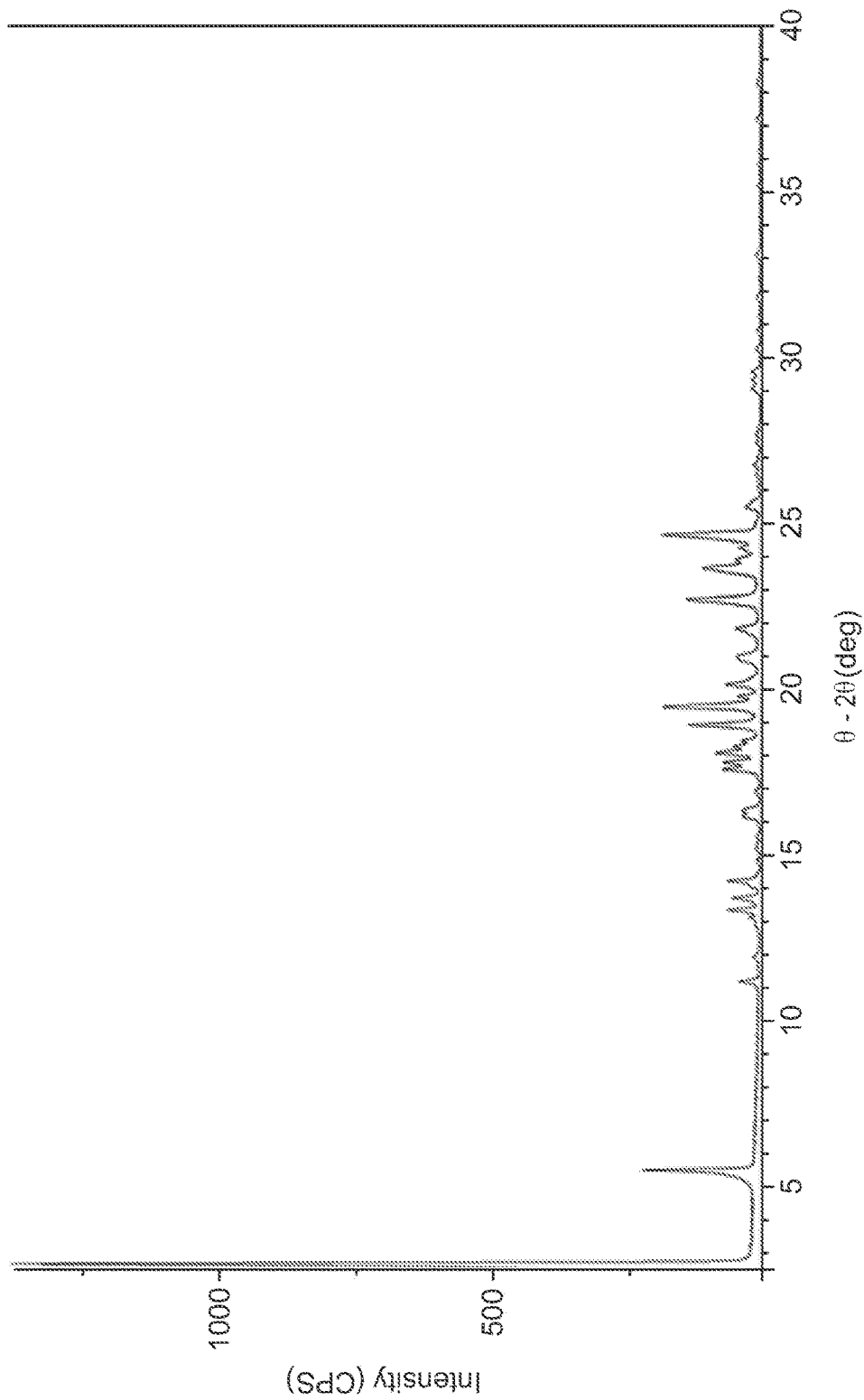
FIG. 1 XRPD scatter for a sample of Compound 1, Form II (sample 1).

The solid form (e.g., crystal state) of a compound may be important when the compound is used for pharmaceutical purposes. Compared with an amorphous solid, the solid physical properties of a crystalline compound may change from one solid form to another, which may impact its suitability for pharmaceutical use. In addition, different solid forms of a crystalline compound may incorporate different types and/or different amounts of impurities. Different solid forms of a compound may also have different chemical stability upon exposure to heat, light and/or moisture (e.g., atmospheric moisture) over a period of time, or different rates of dissolution. There remains a need for solid crystalline forms of phosphonic acid, [[(S)-2-(4-amino-2-oxo-1 (2H)-pyrimidinyl)-1-(hydroxymethyl) ethoxy]methyl]mono [3-(hexadecyloxy)propyl] ester ("Compound 1") that are not hygroscopic, and that exhibit improved chemical stability for use in drug substance and drug product development.

The ability of a substance to exist in more than one crystal form is defined as polymorphism; the different crystal forms of a particular substance are referred to as "polymorphs" of one another. In general, polymorphism is affected by the ability of a molecule of a substance (or its salt or hydrate) to change its conformation or to form different intermolecular or intra-molecular interactions (e.g., different hydrogen bond configurations), which is reflected in different atomic arrangements in the crystal lattices of different polymorphs. In contrast, the overall external form of a substance is known as "morphology," which refers to the external shape of the crystal and the planes present, without reference to the internal structure. A particular crystalline polymorph can display different morphology based on different conditions, such as, for example, growth rate, stirring, and the presence of impurities.

The different polymorphs of a substance may possess different energies of the crystal lattice and, thus, in solid state they can show different physical properties such as form, density, melting point, color, stability, solubility, dissolution rate, etc., which can, in turn, effect the stability, dissolution rate and/or bioavailability of a given polymorph and its suitability for use as a pharmaceutical and in pharmaceutical compositions. See, e.g., *Polymorphism in Pharmaceutical Solids,* 2nd Ed., Drugs and the Pharmaceutical Sciences (2009), Informa Healthcare USA, Inc., New York, N.Y., Chapter 3, page 52, Introduction and Chapter 4, page 77, first full paragraph and page 87, first full paragraph and Caira M. R., *Crystalline Polymorphism of Organic Compounds.*

U.S. Pat. No. 8,569,321 discloses crystalline physical form of Compound 1, which is designated as Form A. The present invention includes new polymorphic form of Compound 1, which is a stable polymorph, and method for preparation thereof.

Compound 1 has been produced at about 100 kg scale utilizing a rapid cooling crystallization process from methanol. The process of production of Form II without seeding involves quick cool-down methanol recrystallization, which results in smaller particle size compared to the particle size of Form II when the process includes seeding and slow cool-down steps.

The present disclosure relates to (i) characterization of selected Compound 1 morphic forms to evaluate solid form and particle differences among the morphic forms, (ii) solid form screening focused on the process solvents to evaluate the propensity of Compound 1 to produce different crystal forms, and (iii) an improved crystallization process which is more controlled and reproducible.

The present disclosure provides methods of synthesis for substituted phosphonic acid esters. In certain aspects, the invention provides methods for the preparation of compounds having the structure of Formula I:

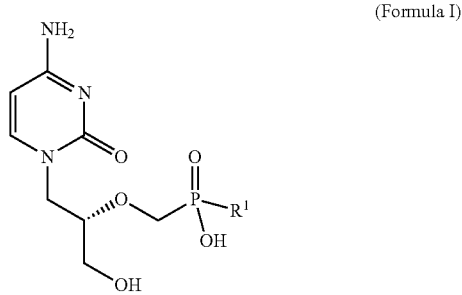

(Formula I)

wherein:

$R^1$ is unsubstituted or substituted $C_1$-$C_6$ alkoxy-, or unsubstituted or substituted $C_1$-$C_{30}$ alkoxy-$C_1$-$C_6$-alkoxy-; or an enantiomer, diastereomer, racemate or a mixture thereof.

In another embodiment, $R^1$ is $C_{10}$-$C_{30}$ alkoxy-$C_2$-$C_4$-alkoxy-.

In another embodiment, $R^1$ is hexadecyloxypropyloxy-.

Provided herein are novel crystalline forms of Compound 1.

In one embodiment, the present disclosure provides methods for the preparation of compounds having the structure of Formula II:

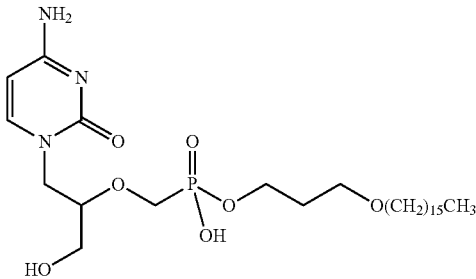

(Compound 1, Formula II)

or enantiomer, diastereomer, racemate or a mixture thereof, or a pharmaceutically acceptable salts thereof.

In one embodiment, the present disclosure provides methods for the preparation of compounds having the structure of Formula III:

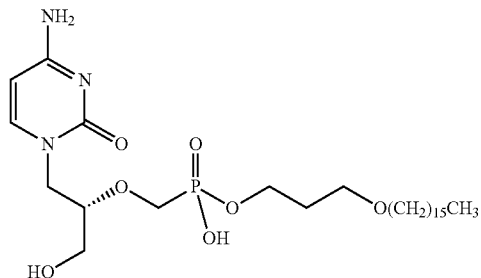

(Compound 1, Formula III)

or a pharmaceutically acceptable salt thereof.

Morphic Forms I, II, & H

Described herein are polymorphic Forms I, II and H of Compound 1 (also referred to herein respectively as "Polymorph I", "Polymorph II" and "Polymorph H").

The Form II of Compound 1 can be produced in a highly crystalline form, which is useful in the preparation of pharmaceutical formulations, and will improve general handling, manipulation, and storage of the drug compound. In an embodiment, the crystalline form of the Form II of a compound having Formula II or III is in a form referred to as "Polymorph II," "morphic Form II" or "Form II." ("Polymorph," "morphic Form," or "Form" is used interchangeably throughout the present disclosure.) As described herein, Polymorph II or Form II exhibits physical properties that can be exploited in order to obtain new pharmacological properties, and that may be utilized in drug substance and drug product development.

Polymorph II (or "morphic Form II" or "Form II") has a number of advantageous physical properties related to its free acid form, and related to other polymorphs. Form II has low hygroscopicity compared to other polymorphs (e.g., Form I and/or Form H) of the compound of Formula II or III. Form II has low hygroscopicity compared to another polymorph form of Compound 1 (e.g., Form I and/or Form H). For consistency with drug formulation (e.g., tableting), it is generally required that the polymorphic form of the active pharmaceutical ingredient (API) compound be minimally hygroscopic. Drug forms that are highly hygroscopic may also be unstable, as the drug form's dissolution rate (and other physico-chemical properties) may change as it is stored in settings with varying humidity. Also, hygroscopicity can impact large-scale handling and manufacturing of a compound, as it can be difficult to determine the true weight of a hygroscopic active agent when preparing a pharmaceutical composition comprising that agent. For example, in large scale tableting or other medicinal formulating preparations, highly hygroscopic compounds can result in batch manufacturing inconsistency creating clinical and/or prescribing difficulties. Form II may have low hygroscopicity compared to other polymorphs (e.g., Form I and/or Form H) of the compound of Formula II or III. As such, morphic Form II is stored over appreciable periods or conditions (e.g., low relative humidity conditions), without substantial or any detrimental formulating changes.

In one embodiment, the present disclosure provides a morphic Form II of Compound 1. The present disclosure provides a morphic Form II which is anhydrous.

In some embodiments, Compound 1 is substantially free of impurities. In some embodiments, the purity of Compound 1 or a pharmaceutically acceptable salt thereof is equal to or greater than 92% (e.g., ≥92%, ≥93%, ≥94%, ≥95%, ≥96%, ≥97%, ≥98%, ≥99%, or ≥99.5%). In yet other embodiments, Compound 1 or a pharmaceutically acceptable salt thereof has a purity of equal to or greater than 91% (e.g., ≥91%, ≥92%, ≥93%, ≥94%, ≥95%, ≥96%, ≥97%, ≥98%, >99%, or >99.5%). In one embodiment, the purity of Compound 1 or a pharmaceutically acceptable salt thereof is about 99%. In one embodiment, the Compound 1 polymorph is a hydrate. In another embodiment, the Compound 1 polymorph is not a hydrate. In yet another embodiment, the compound is a solvate, e.g., a methanol solvate, an ethanol solvate, or an isopropanol solvate.

In some embodiments, the purity of the compound of Formula I, II, and/or III (or a pharmaceutically acceptable salt thereof) is equal to or greater than 92% (e.g., ≥92%, ≥93%, ≥94%, ≥95%, ≥96%, ≥97%, ≥98%, ≥99%, or ≥99.5%). In other embodiments, the compound is in Form II or a pharmaceutically acceptable salt thereof. In yet other embodiments, Compound 1 is Form II and has a purity of equal to or greater than 91% (e.g., ≥91%, ≥92%, ≥93%, ≥94%, ≥95%, ≥96%, ≥97%, ≥98%, >99%, or >99.5%). In one embodiment, the purity of the compound of Formula I, II, and/or III (or a pharmaceutically acceptable salt thereof) is about 99%. In one embodiment, the compound of Formula I, II, or III (or a pharmaceutically acceptable salt thereof) is obtained from recrystallizing a crude compound from a suitable recrystallizing solvent described herein.

The present disclosure provides synthesizing Compound 1 or a pharmaceutically acceptable salt thereof by varying the temperature and methanol:water ratio. The present disclosure provides synthesizing Form II of the compound of Formula II or III (or a pharmaceutically acceptable salt thereof) by varying the temperature and methanol:water ratio. In alternative temperature and methanol:water ratios, hydrate form (e.g., Form H) or a mixture of hydrate form (e.g., Form H) and an anhydrate form (e.g., Form II) is formed.

In some embodiments, an anhydrous form (e.g., Form II) of the compound of Formula II and/or III (or a pharmaceutically acceptable salt thereof) is obtained during crystallization process by setting up slurries in different methanol-water concentrations. In one embodiment, from sub-ambient slurries (i.e., slurries prepared in the temperature of the surroundings), methanol:water ratio of about 98:2 or 99:1 recover anhydrous morphic form (e.g., Form II). In contrast, in another embodiment, methanol:water ratio of about 97:3 or greater recovers hydrate morphic Form (e.g., Form H) either in mixture with Form II or as a pure form of Form H. The present disclosure provides that water concentration of equal to or no more than between about 1 and 3% is required to synthesize an anhydrous Form (e.g., Form II) of the compound of Formula II or III (or a pharmaceutically acceptable salt thereof). The water content of such embodiments vary depending on the water content in the methanol, and is more than about 1 to 3% for synthesizing an anhydrous Form (e.g., Form II) of the compound of Formula II or III (or a pharmaceutically acceptable salt thereof).

In another embodiment, from slurries at room-temperature, an anhydrous morphic form (e.g., Form II) of the compound of Formula II or III (or a pharmaceutically acceptable salt thereof) is obtained in the presence of equal to or less than 5% (e.g., ≤5-4.9%, ≤4.9-4.8%, ≤4.8-4.7%, ≤4.7-4.6%, ≤4.6-4.5%, ≤4.5-4.4%, ≤4.4-4.3%, ≤4.3-4.2%, ≤4.2-4.1%, 4.1-4.0%, ≤4.0-3.0%, or ≤3.0-2.0%) water in the slurry. In one embodiment, from slurries at room-temperature, the critical water concentration to obtain an anhydrous morphic form (e.g., Form II) of the compound of Formula II or III (or a pharmaceutically acceptable salt thereof) is equal to or less than 5%.

In yet another embodiment, from slurries at a temperature higher than the room temperature (e.g., equal to or more than 30° C.), an anhydrous morphic form (e.g., Form II) of the compound of Formula II or III is obtained in the presence of equal to or less than 10% (e.g., ≤10-9%, ≤9-8%, ≤8-7%, ≤7-6%, ≤6-5%, ≤5-4%, ≤4-3%, or ≤3-2%) water in the slurry. In one embodiment, from slurries at about 45° C., the critical water concentration to obtain an anhydrous morphic form (e.g., Form II) of the compound of Formula II or III (or a pharmaceutically acceptable salt thereof) is equal to or less than 10%.

In some embodiments, a composition comprising the morphic Form II of the compound of Formula II or III (or a pharmaceutically acceptable salt thereof) is substantially free of Form I and/or Form H. For example, a composition comprising the morphic Form II of the present disclosure comprises equal to or less than 10% Form I and/or Form H. In some embodiments, the Form II composition comprises equal to or less than 9%, equal to or less than 8%, equal to or less than 7%, equal to or less than 6%, equal to or less than 5%, equal to or less than 4%, equal to or less than 3%, equal to or less than 2%, equal to or less than 1%, equal to or less than 0.9%, equal to or less than 0.8%, equal to or less than 0.7%, equal to or less than 0.6%, equal to or less than 0.5%, equal to or less than 0.4%, equal to or less than 0.3%, equal to or less than 0.2%, equal to or less than 0.1%, equal to or less than 0.05%, equal to or less than 0.01%, or equal to or less than 0.001% Form I and/or Form H.

In some embodiments, a composition comprising morphic Form II of the present disclosure converts to a hydrate Form (e.g., Form H) if stored under relative humidity (RH) of 40% or more. In some embodiments, a composition comprising morphic Form II of the present disclosure partially converts to morphic Form H if stored under relative humidity of equal to or more than 40% for several days. In some embodiments, a composition comprising the morphic Form II partially converts to a hydrate form (e.g., Form H) after exposure to about 43% relative humidity (RH) for about 12 days. A complete conversion of a composition comprising the morphic Form II of the present disclosure occurs at about equal to or more than 80% RH, about equal to or more than 81% RH, about equal to or more than 82% RH, about equal to or more than 83% RH, about equal to or more than 84% RH, about equal to or more than 85% RH, about equal to or more than 86% RH, about equal to or more than 87% RH, about equal to or more than 88% RH, about equal to or more than 89% RH over between 5-20 days (e.g., 5 days, 6 days, 7 days, 8 days, 9 days, 10 days, 11 days, 12 days, 13 days, 14 days, 15 days, 16 days, 17 days, 18 days, 19 days, 20 days).

The present disclosure provides that exposure of Form II to different RH stressing conditions from about 43 to about 85% RH for about 12 days results in minor conversion from Form II to Form H. In one embodiment, at about 85%, RH complete conversion of Form II to Form H occurs. See Table 1. The present disclosure provides that exposure of Form II to higher humidity is sufficient for conversion to the hydrate form.

TABLE 1

Conversion of Form II to Form H

| Solvent[a] | Temp (° C.) | Observation | Results |
|---|---|---|---|
| Methanol:water (99:1) | ~2-8 | Opaque aggregates and fines with no distinct morphology | Form II |
| Methanol:water (97:3) | ~2-8 | Opaque aggregates and fines with no distinct morphology | Form H |
| Methanol:water (95:5) | ~2-8 | Opaque aggregates and fines with no distinct morphology | Form H |
| Methanol:water (93:7) | ~2-8 | Opaque aggregates and fines with no distinct morphology | Form H |
| Methanol:water (97:3) | RT | Opaque aggregates and fines with no distinct morphology | Form II + Minor Form H |
| Methanol:water (95:5) | RT | Opaque aggregates and fines with no distinct morphology | Form H |
| Methanol:water (93:7) | RT | Opaque aggregates and fines with no distinct morphology | Form H |
| Methanol:water (90:10) | RT | Opaque aggregates and fines with no distinct morphology | Form H |
| Methanol:water (95:5) | ~44-45 | Opaque aggregates and fines with no distinct morphology | Form II + Minor Form H |
| Methanol:water (90:10) | ~44-45 | Opaque aggregates and fines with no distinct morphology | Form H |
| Methanol:water (85:15) | ~44-45 | Opaque aggregates and fines with no distinct morphology | Form H |
| Methanol:water (80:20) | ~44-45 | Opaque aggregates and fines with no distinct morphology | Form H |

[a]Slurry experiments were prepared with Form II (Compound 1 (Compound 1)) and seeded with a small amount of Form H. Samples were left to stir for 7-9 days.

Solubility

The present disclosure provides morphic Form II with low solubility in methanol. The solubility may be estimated based on the total volume of solvent needed to provide complete dissolution. The actual solubility may be greater than the value calculated due to the incremental addition of solvent and kinetics of dissolution of the material. The solubility is expressed as "less than" if dissolution did not occur during the experiment, or "more than" if dissolution occurred after the addition of the first aliquot.

TABLE 2

Solubility Definitions

| Term | Definition |
|---|---|
| Low solubility | <1 mg/mL |
| Limited solubility | 1-20 mg/mL |
| Intermediate solubility | 20-100 mg/mL |
| Good solubility | 100-200 mg/mL |
| High solubility | >200 mg/mL |

In some embodiments, a composition comprising the morphic Form II of the present disclosure is equal to or less than about 5 mg/mL soluble (e.g., ≤5-4 mg/mL, ≤4-3 mg/mL, ≤3-2 mg/mL, ≤2-1 mg/mL, or ≤1-0.01 mg/mL) in 1:1 methanol:water ratio at room temperature. In one embodiment, a composition comprising the morphic Form II of the present disclosure is less than about 3 mg/mL soluble in 1:1 methanol:water ratio at room temperature. In some embodiments, a composition comprising the morphic Form II of the present disclosure is equal to or less than about 15 mg/mL soluble (e.g., ≤15-14 mg/mL, ≤14-13 mg/mL, ≤13-12 mg/mL, ≤12-11 mg/mL, ≤11-10 mg/mL, ≤10-9 mg/mL, ≤9-8 mg/mL, ≤8-7 mg/mL, 7-6 mg/mL, or 6-5 mg/mL) in 1:1 methanol:water ratio at a temperature higher than room temperature (e.g., equal to or more than 30° C.). In one embodiment, a composition comprising the morphic Form II of the present disclosure is less than about 14 mg/mL soluble at about 63° C.

TABLE 3

Estimated Solubility of Form II

| Solvent | Temperature (° C.) | Solubility (mg/mL)[a] |
|---|---|---|
| Methanol:Water 1:1 | RT | <3 |
|  | ~63 | <14 |

[a]Solubility was estimated based on the total solvent used to give a solution; actual solubility may be greater of because of the volume of the solvent portions utilized or a slow rate of dissolution. Solubility is rounded to the nearest mg/mL.

TABLE 4

Methanol Solubility and Metastable Zone (MSZ)* Data of Form II

| Concentration[a] (mg/mL) | Clear Point (° C.) | Cloud Point 1[b] (° C.) | Cloud Point 2[c] (° C.) |
|---|---|---|---|
| 20.3 | 53.6 | 37.6 | 38.2 |
| 29.4 | 56.2 | 45.1 | 44.6 |
| 38.9 | 58.1 | 45.1 | 51.1 |
| 50.5 | 60.2 | 51.0 | 56.6 |
| 64.3 | 60.5 | 48.5 | 58.8 |
| 80.4 | 61.2 | 49.7 | 57.9 |
| 95.6 | 61.9 | 58.1 | 59.9 |
| 166.6 | 63.1 | 58.1 | 61.1 |

[a]Non-GMP experiment run in Crystal16 ™ was used as starting material.
[b]Determined from 0.5° C./min cooling rate.
[c]Determined from 0.03 C./min cooling rate.
*If the solution mentioned previously is further cooled, a new solid phase is formed by nucleation at a specific point, which define the metastable zone.

Particle Size of Polymorphic Compound 1

In another embodiment, particle size analysis and Scanning Electron Microscopy (SEM) images provide particle characteristics and variations of characteristics for crystals formed under different crystallization conditions.

The present disclosure provides an internal structure of Form II of the compound having Formula II or III (or a pharmaceutically acceptable salt thereof) such that the crystal unit cell dimension and packing are different from internal structures of Form I and Form H. The present disclosure also provides a single crystalline form (e.g., Form II) of the Formula of II or III (or a pharmaceutically acceptable salt thereof). Form II of the present disclosure is characterized by XRPD indexing, unique DSC characteristics, distinct particle size and form, and lower solubility in methanol.

In one embodiment, Form II forms large agglomerates along with smaller plate-shaped particles. The SEM shows that the Form I of the present disclosure have the largest agglomerates (>500 µm) and the surfaces appeared significantly smoother compared to the other two lots. In one embodiment, the particles do not contain any cemented agglomerates and are composed of larger, thin, plate-shaped particles. The crystal particles obtained have a bi-modal distribution with a mode of small particles at about 6-10 µm and a larger mode at about 60-160 µm. In one embodiment, the sample has a single mode at about 90 µm with a tail of finer particles. In another embodiment the sample has a large d90 (particle diameter at which 90% of the sample is smaller than), consistent with observations from the SEM images.

The present disclosure provides particle sizes of the starting material for crystallization; methanol recrystallized material; and comilled material from an about 45 kg recrystallization batch. The starting material has agglomerates (about 100 μm) composed of smaller plates. The methanol recrystallized forms of the present disclosure has larger primary particles, some agglomeration without cementation and a single particle size mode. The comilled sample is similar to the methanol recrystallized batch but shows a slightly smaller particle distribution suggesting only minor particle attrition occurred during the milling step.

TABLE 5

Particle size distribution of sample 1, 3 and 4 of Compound 1 Form II

| Sample no. | d10 (μm)$^a$ | d50 (μm)$^b$ | d90 (μm)$^c$ | file | Record | Page |
|---|---|---|---|---|---|---|
| Sample 1 | 19.297 | 81.603 | 168.698 | 613675 | 1 | 10, 13 |
| Sample 4 | 17.410 | 85.440 | 199.029 | 613739 | 2 | 10, 14 |
| Sample 3 | 19.896 | 101.748 | 274.113 | 613674 | 1 | 10, 15 |

$^a$10% of the total volume of particles is comprised of particles no larger than the indicated size in μm.
$^b$50% of the total volume of particles is comprised of particles no larger than the indicated size in μm.
$^c$90% of the total volume of particles is comprised of particles no larger than the indicated size in μm.

Some embodiments provide particles and agglomerates of different sizes and forms. The particle and agglomerate sizes and forms vary depending on the percentage of seeding. In one embodiment, particles and agglomerates synthesized by a crystallization process seeded with 0.5% of Compound 1 is distinct from the particles and agglomerates synthesized by a crystallization process seeded with 3% of Compound 1. Compare FIGS. 22 and 23. Particle size analysis of these embodiments provide that, due to the larger number of particles/surface area available for crystal growth, the 3% seeded sample has smaller d10 (particle diameter at which 10% of the sample is smaller than), d50 (particle diameter at which 50% of the sample is smaller than), and d90 (particle diameter at which 90% of the sample is smaller than) values compared to the 0.5% seeded sample. The samples crystallized using the hydrate e.g., Form H, as the starting material or which contained excess water during the crystallization, appear to generate samples with a lower degree of agglomeration. The higher water content changes the solubility or induction time and avoids the secondary nucleation and agglomeration.

X-Ray Diffraction

In certain embodiments, Forms I, II, and H of the compound having Formula II or III are identifiable on the basis of their respective characteristic peaks in an X-ray powder diffraction analysis. X-ray powder diffraction pattern, also referred to as XRPD pattern, is a scientific technique involving the scattering of x-rays by crystal atoms, producing diffraction pattern that yields information about the structure of the crystal. Internal structure of crystals is accessible by x-ray diffraction analysis. Polymorphs have different crystal forms based on their different structures, and physical and chemical properties.

Metastable zone width (MSZW) is a critical parameter in the crystallization process as it reveals the nucleation behavior of the system. MSZW is a nucleation kinetic-limited parameter that is highly dependent on process condition. Many factors may influence the value of MSZW, e.g., rate of cooling, agitation, the presence of foreign particles and impurities. MSZW decreases as stirrer speed increases; MSZW widens at N>400 rpm; and MSZW widens as cooling rate rises. In one embodiment, large differences in the metastable zone are observed for both Form II and Form I between the rapid cooling rate of about 0.5° C./min and a very slow cooling rate of about 0.03° C./min. In another embodiment, narrow metastable cooling rates are observed at higher concentrations (e.g., about 100 mg/mL).

The present disclosure provides morphic Form II of compound having Formula II or III (or a pharmaceutically acceptable salt thereof) with a MSZW that results in lower solubility in methanol compared to polymorphs Form I and/or Form H. Lower solubility of Form II in methanol compared to Form I of the present disclosure is consistent with Form II being the more stable form than Form I.

The crystallization of the present disclosure may include "seeding" in order to achieve a desired final product size. Seeding also provides the ability to obtain preferable polymorph form, obtain desired crystal morphology, and obtain polymorphs or pseudo-polymorphs. In some embodiments of the present disclosure, crystallization process involves seeding with Form I, II, or H of compound having Formula II or III (or a pharmaceutically acceptable salt thereof). The present disclosure provides Form II seeding during the crystallization process.

An embodiment of the present disclosure provides a morphic crystalline form (e.g., Form II) with an X-ray diffraction pattern including prominent peaks at about 2.81 and about 5.63 degrees 2Θ. In one embodiment a composition comprising the morphic Form II of the compound having Formula II or III is characterized by an X-ray diffraction pattern substantially similar to that set forth in FIG. 1 or FIG. 20, indexing substantially similar to that set forth in FIG. 2, and DSC Thermogram substantially similar to that set forth in FIG. 4.

Figure 6:
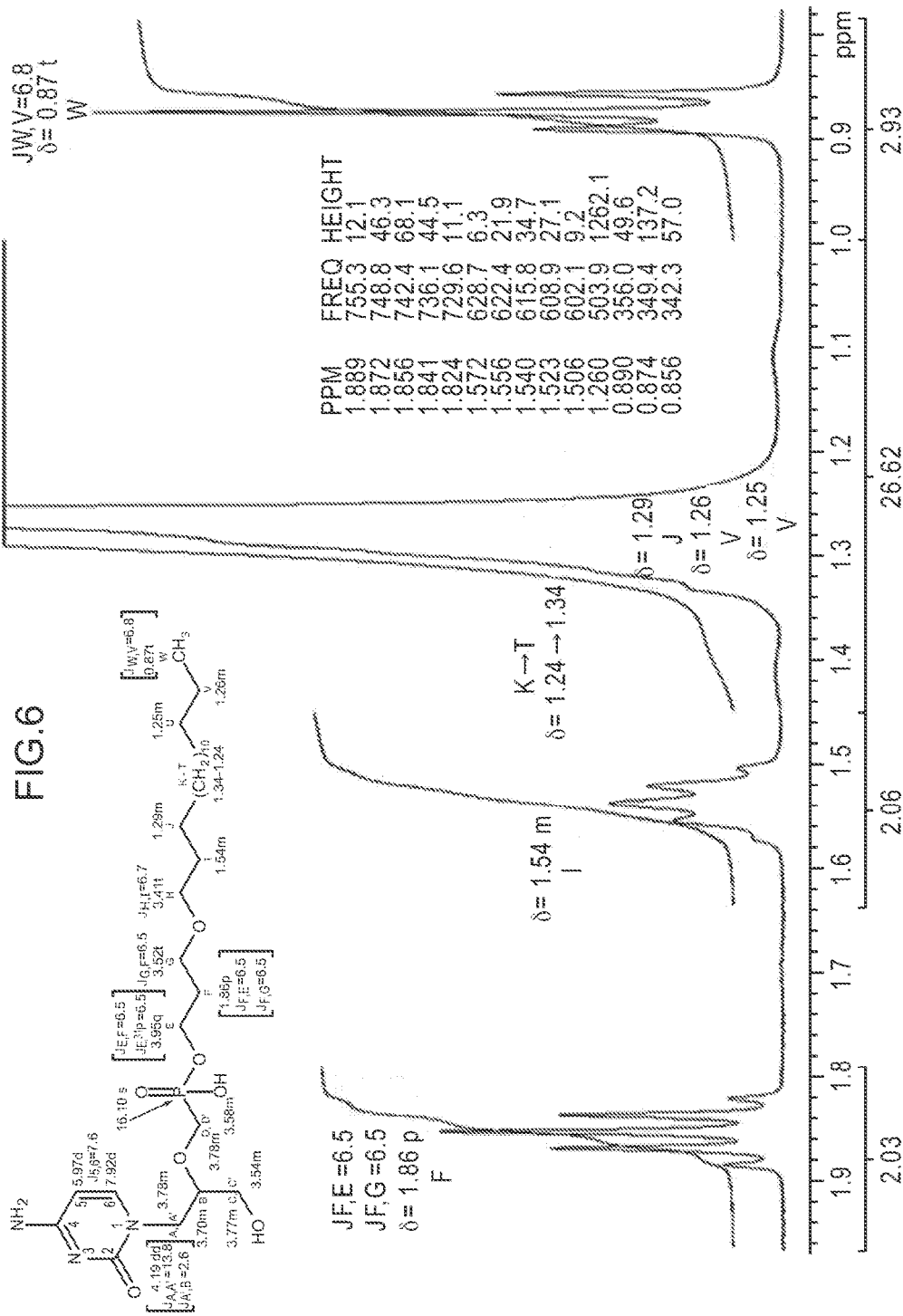
FIG. 6 shows $^1$H NMR spectrum of Compound 1, Form II (sample 1).
Figure 7:
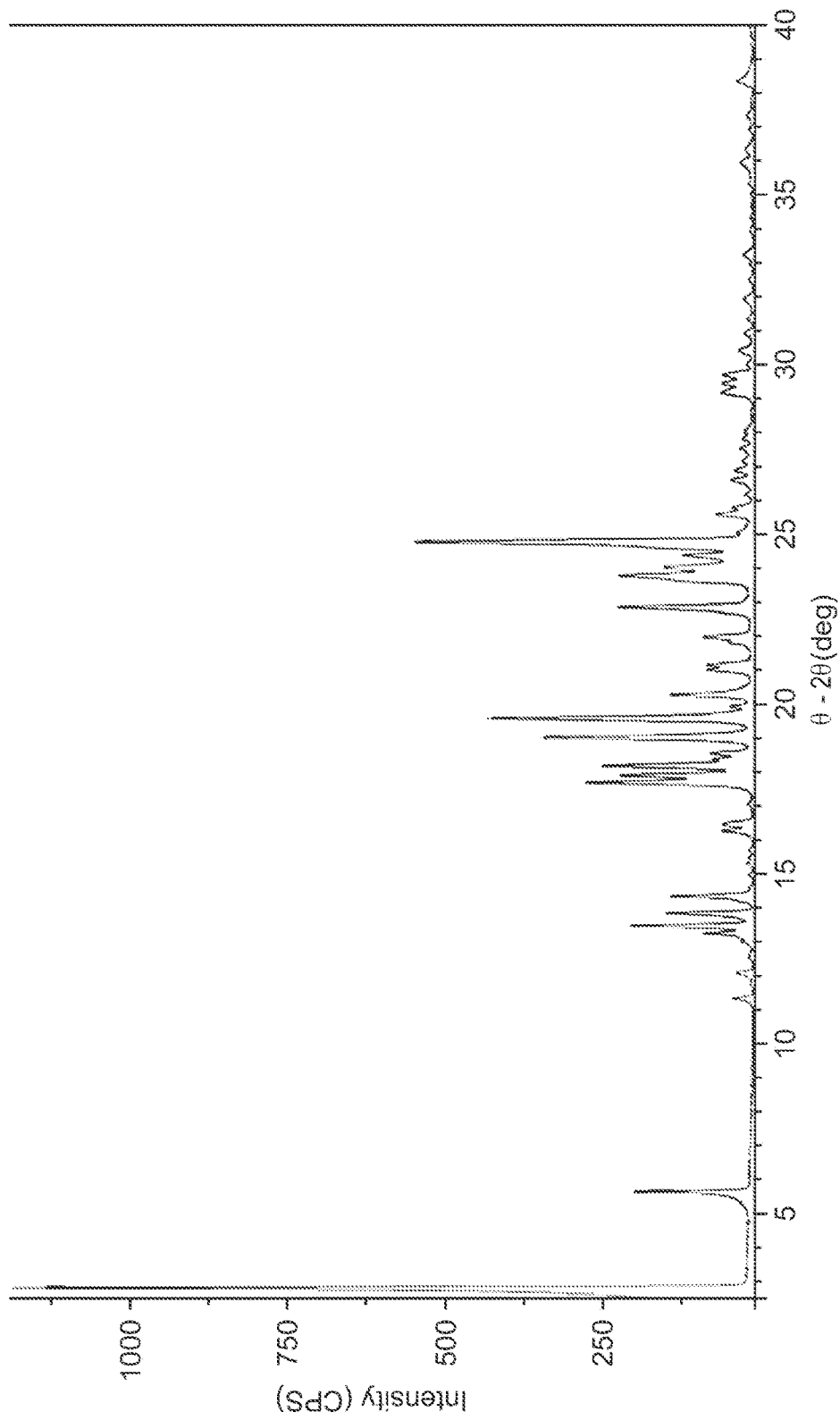
FIG. 7 shows XRPD scatter for a sample of Compound 1, Form II (sample 2).
Figure 8:
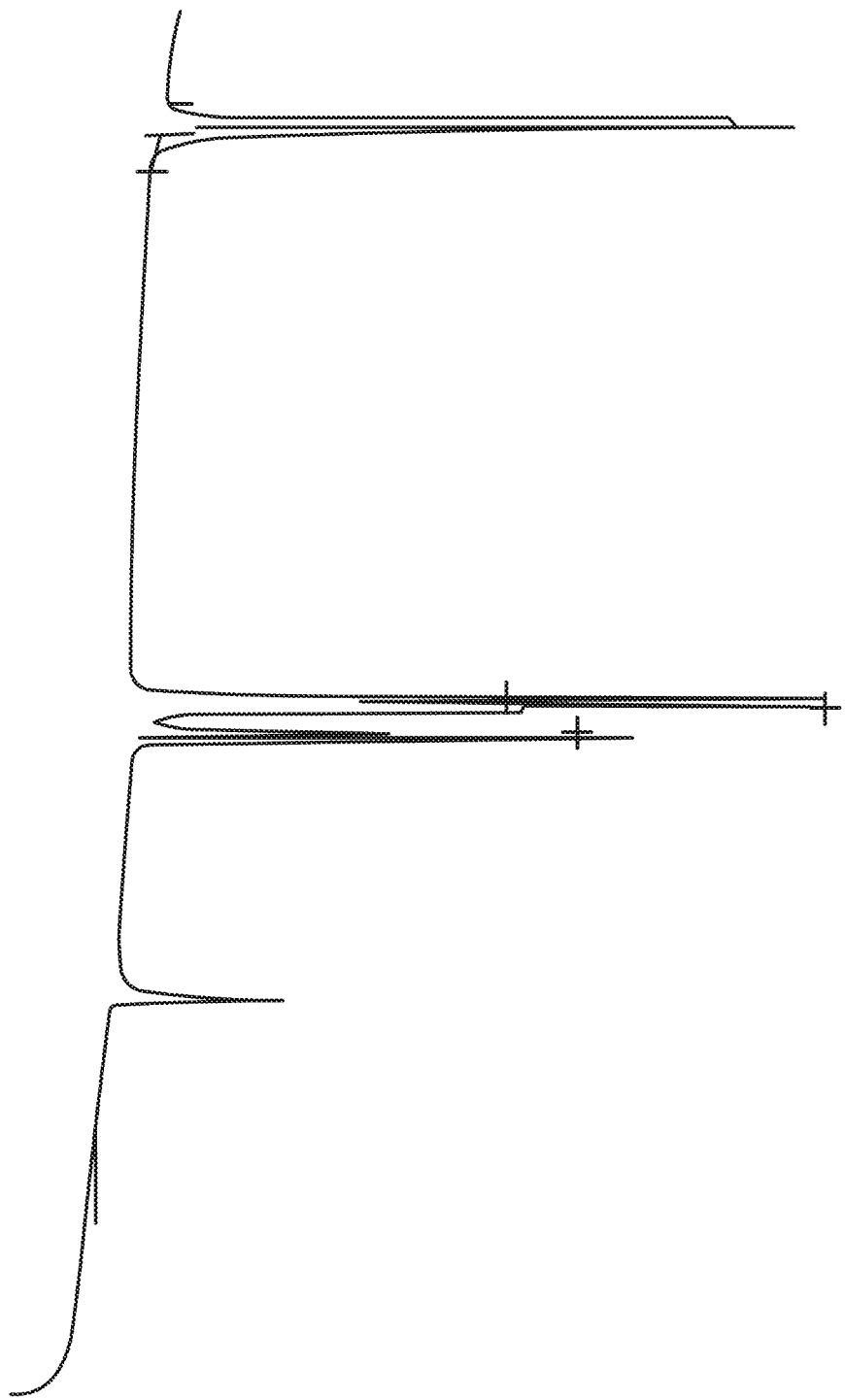
FIG. 8 shows DSC thermogram of Compound 1, Form II (sample 2).
Figure 9:
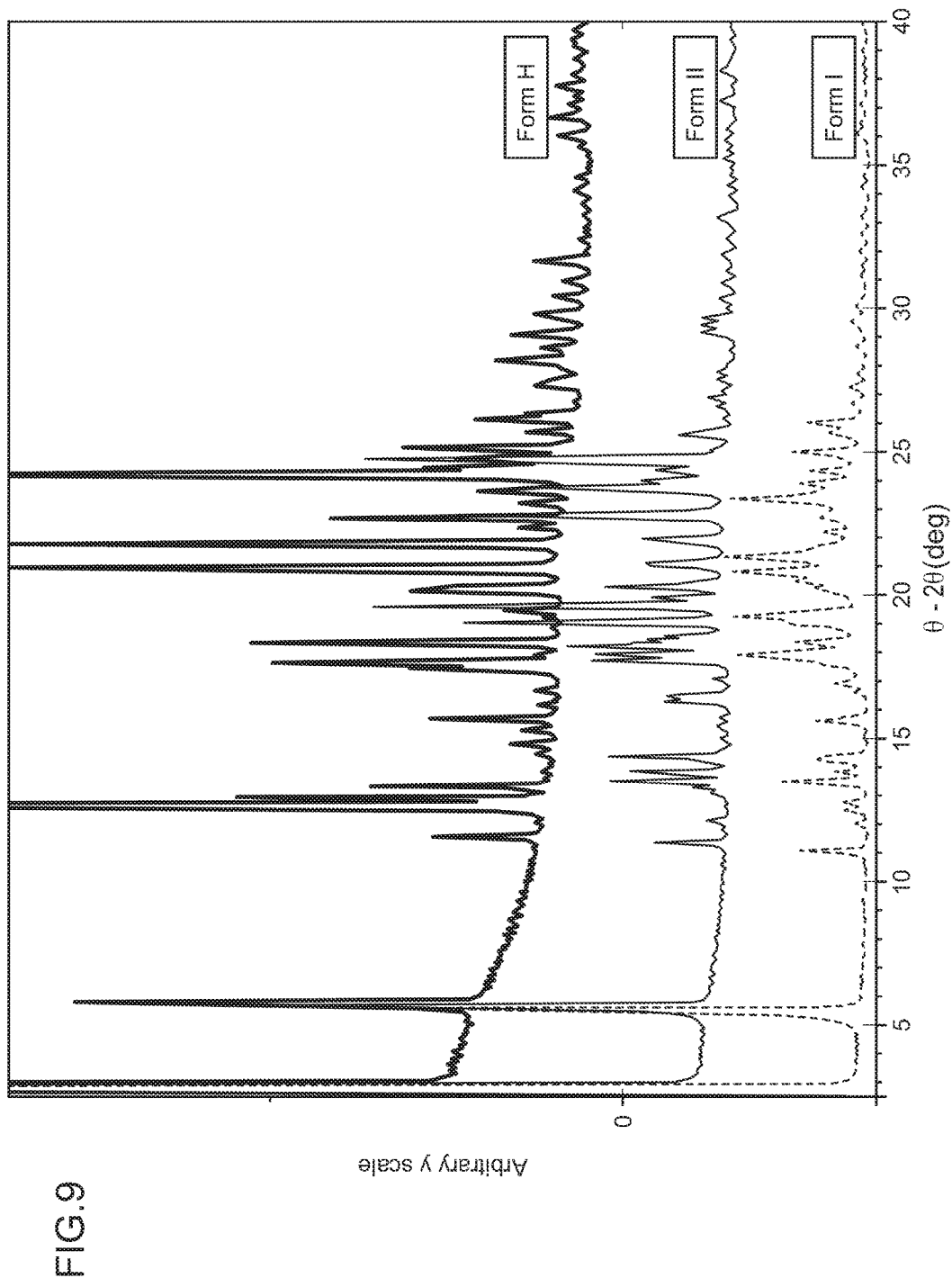
FIG. 9 shows comparison of XRPD patterns of Compound 1, Form I, II (sample 1), and H.
Figure 10:
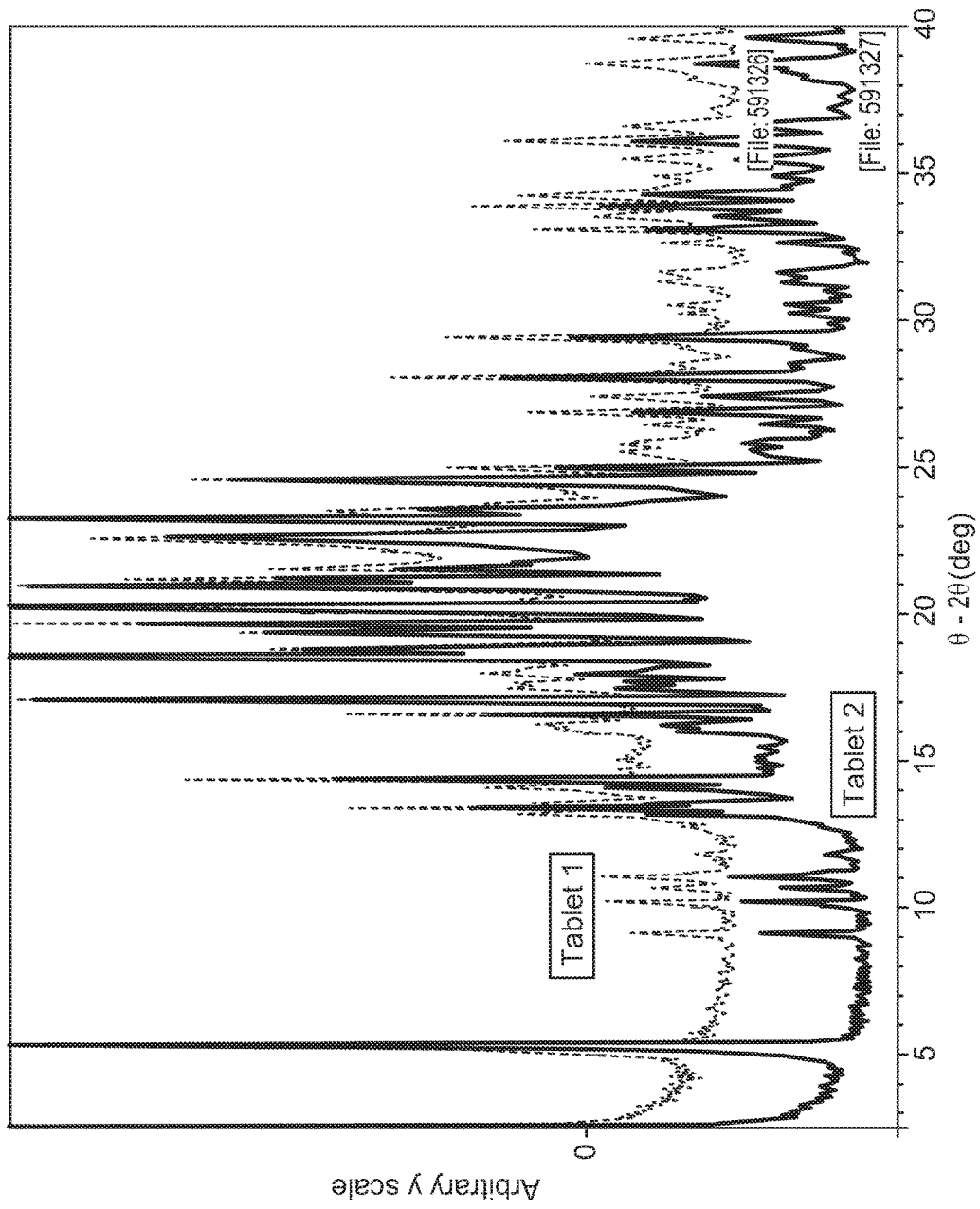
FIG. 10 shows XRPD overlay of Compound 1 drug product samples (Tablet 1 (upper plot) and Tablet 2 (lower plot)).
Figure 11:
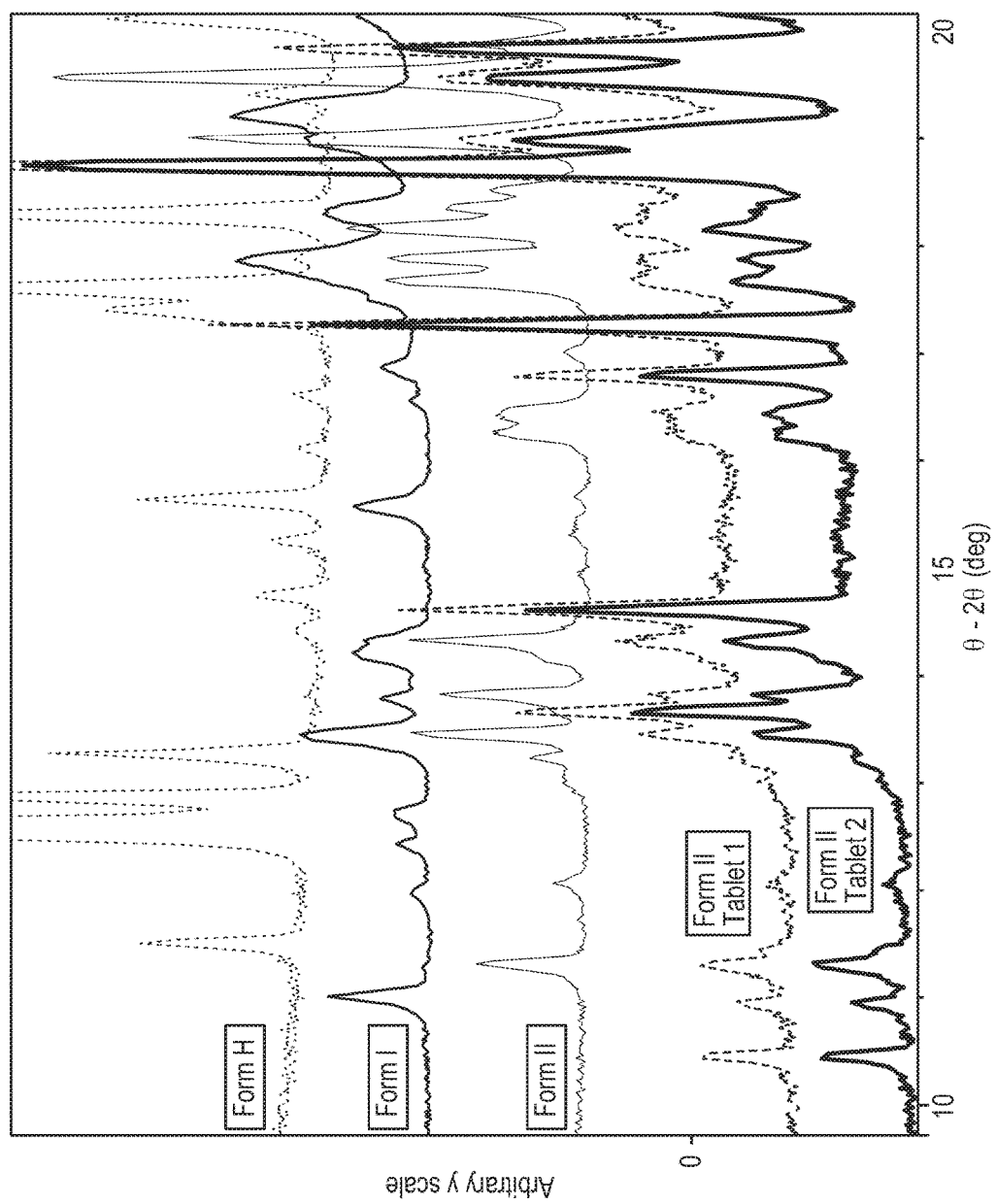
FIG. 11 shows XRPD overlay of Compound 1 drug product samples with Form II, Form I (Tablet 1), and Form H.
Figure 12:
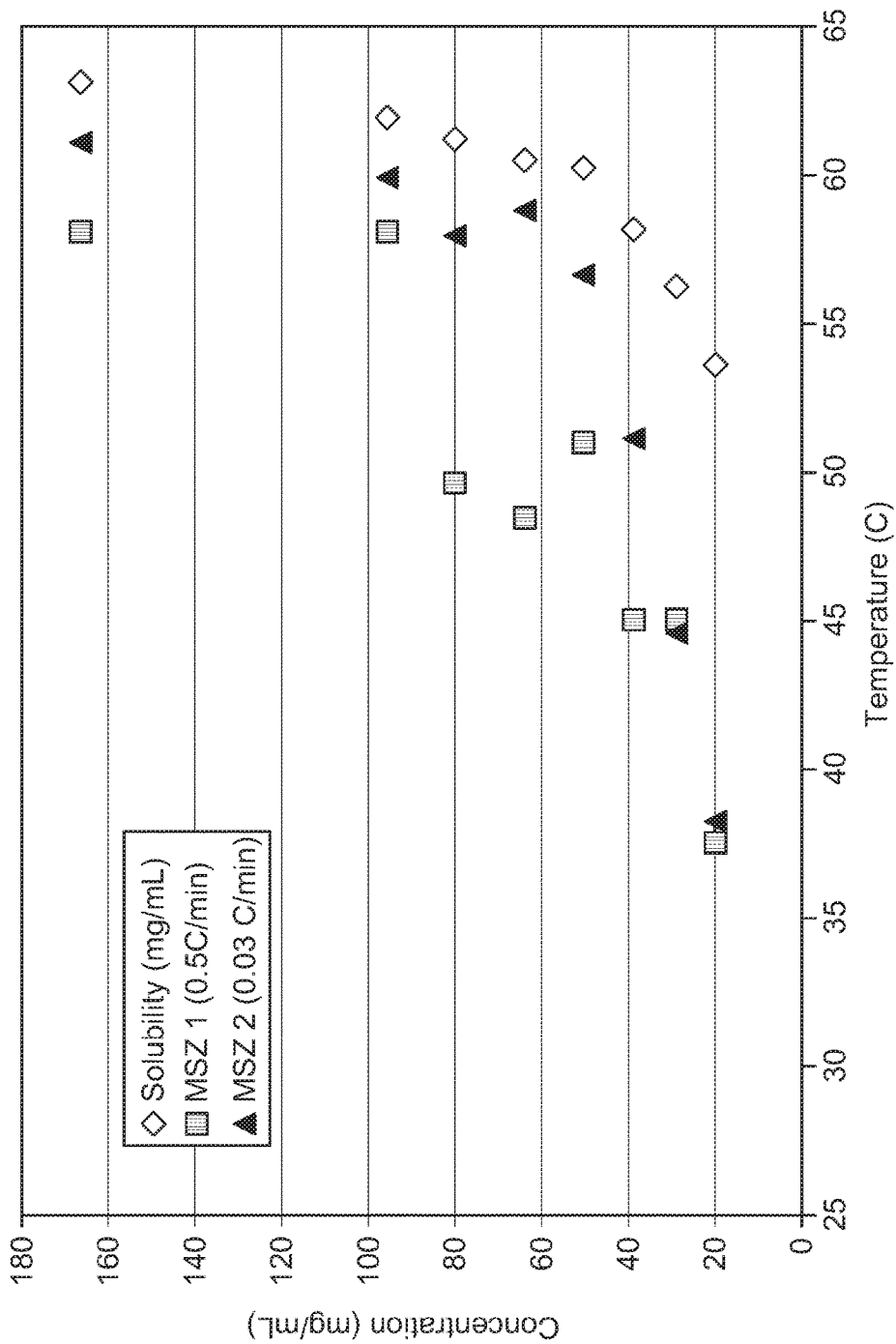
FIG. 12 shows solubility curve and MSZ of Compound 1, Form II (sample 1) in methanol.

The present disclosure provides recrystallization of a crystalline form (e.g., Form II) of the compound having Formula II or III (Table 5). In one embodiment of the present disclosure, primarily a single phase of crystalline Form II is provided, as evident from the XRPD pattern. In one embodiment, $^1$H NMR spectroscopy of the sample provides Formula II or III as the chemical structure of the isolated crystalline Form II (FIG. 6).

Figure 2:
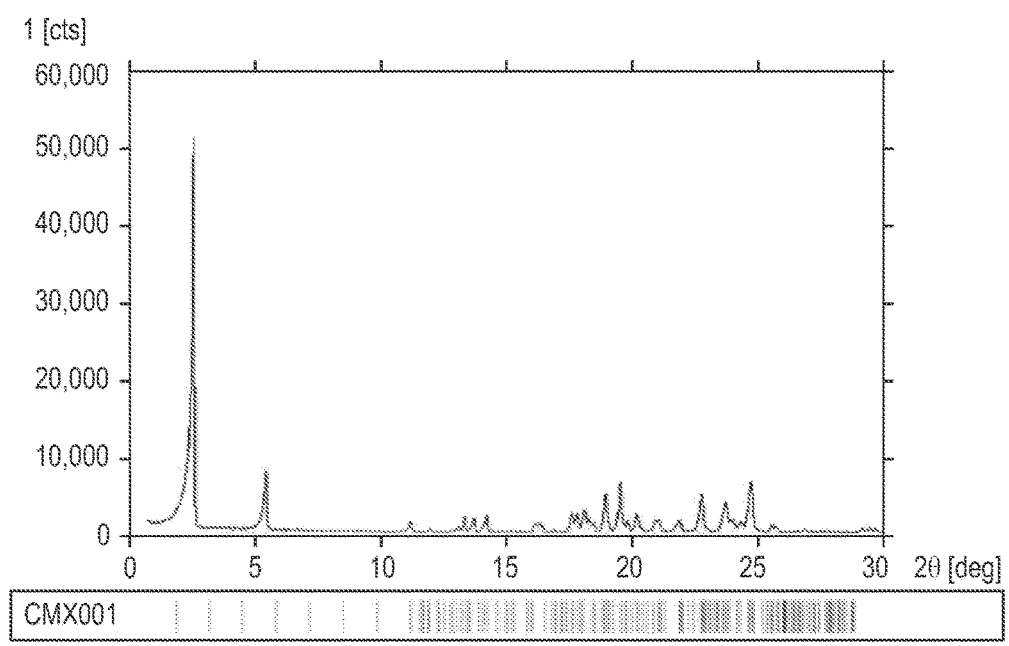
FIG. 2 shows indexing results of Compound 1 Form II for XRPD collected with Cu-Kα radiation (sample 1).
Figure 4:
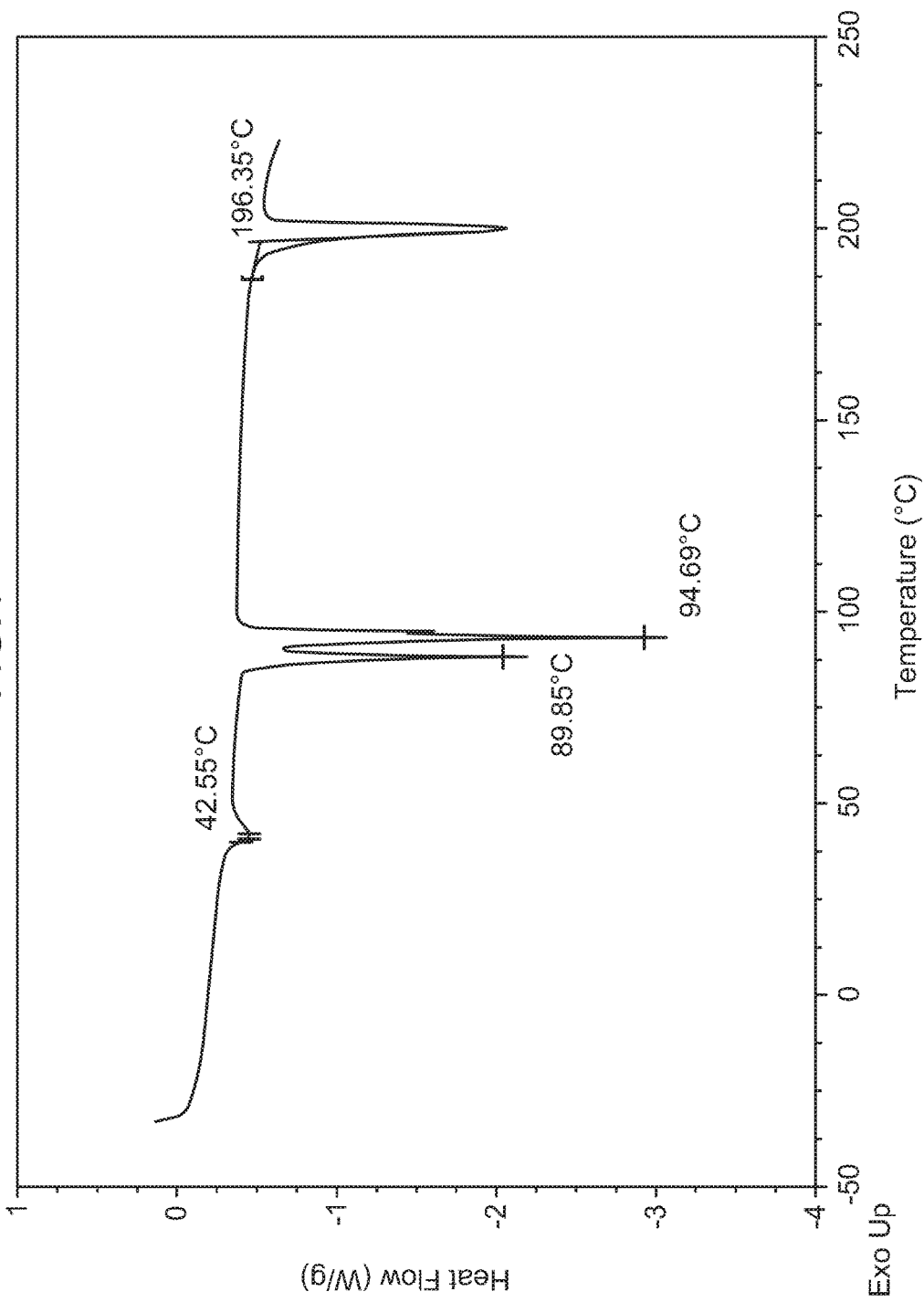
FIG. 4 shows DSC thermogram of Compound 1, Form II (sample 1).
Figure 5:
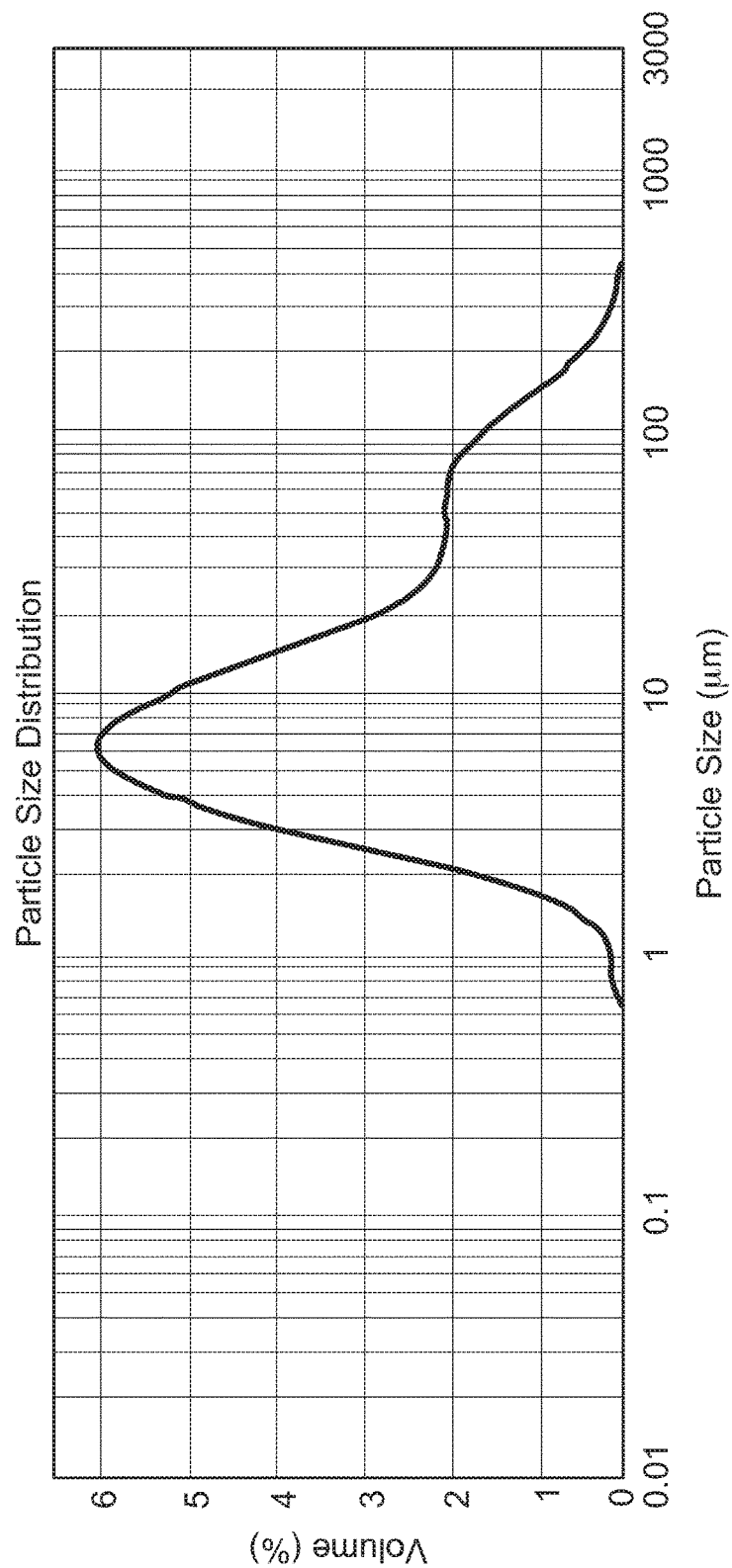
FIG. 5 shows particle size distribution of Compound 1, Form II, with volume weighted mean as 25.663.
Figure 20:
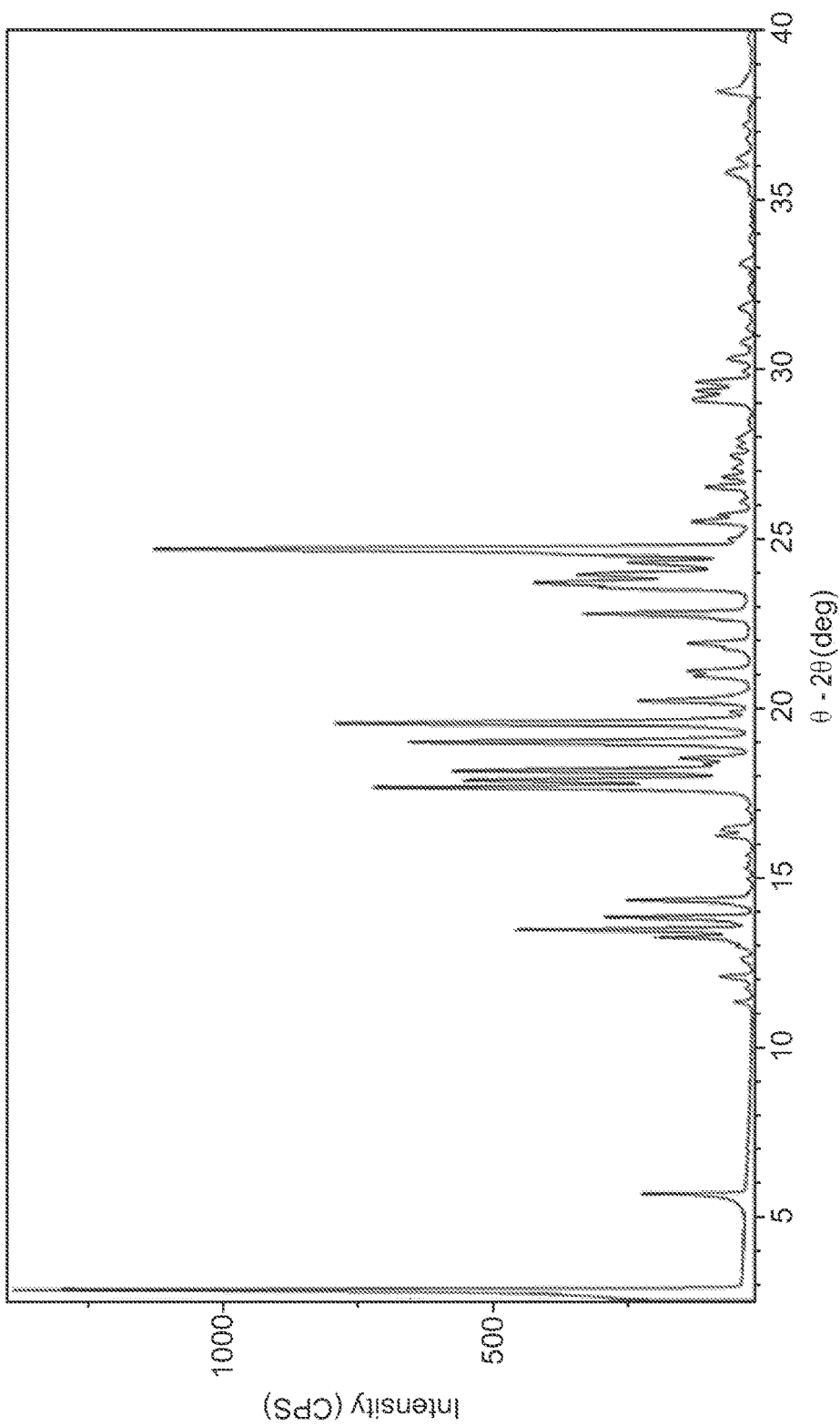
FIG. 20 shows XRPD scatter for a sample of Compound 1, Form II (sample 3).

In certain embodiments, Form II exhibits an X-ray powder diffraction pattern having from two (2) to seven (7) characteristic peaks expressed in degrees 2θ at 2.81, 5.63, 19.00, 19.57, 22.76, and 24.70±0.2, or having an X-ray diffraction pattern substantially similar to that set forth in FIG. 1 or FIG. 20, indexing substantially similar to that set forth in FIG. 2, and DSC Thermogram substantially similar to that set forth in FIG. 4. In one embodiment, the XRPD peaks of Form II are substantially similar to that set forth in Table 6.

TABLE 6

Observed and Prominent Peaks for Form II

| | d space (Å) | Intensity (%) |
|---|---|---|
| Observed Peaks °2θ | | |
| 2.81 ± 0.20 | 31.451 ± 2.410 | 100 |
| 5.63 ± 0.20 | 15.688 ± 0.577 | 16 |
| 11.30 ± 0.20 | 7.832 ± 0.141 | 3 |
| 12.05 ± 0.20 | 7.345 ± 0.124 | 2 |

TABLE 6-continued

Observed and Prominent Peaks for Form II

| | d space (Å) | Intensity (%) |
|---|---|---|
| 13.22 ± 0.20 | 6.697 ± 0.102 | 2 |
| 13.45 ± 0.20 | 6.581 ± 0.099 | 5 |
| 13.81 ± 0.20 | 6.415 ± 0.094 | 4 |
| 14.32 ± 0.20 | 6.184 ± 0.087 | 5 |
| 14.92 ± 0.20 | 5.936 ± 0.080 | 1 |
| 15.64 ± 0.20 | 5.665 ± 0.073 | 1 |
| 16.25 ± 0.20 | 5.456 ± 0.068 | 3 |
| 16.41 ± 0.20 | 5.401 ± 0.066 | 3 |
| 17.00 ± 0.20 | 5.217 ± 0.062 | 1 |
| 17.67 ± 0.20 | 5.021 ± 0.057 | 6 |
| 17.87 ± 0.20 | 4.965 ± 0.056 | 5 |
| 18.15 ± 0.20 | 4.888 ± 0.054 | 6 |
| 18.35 ± 0.20 | 4.835 ± 0.053 | 4 |
| 18.50 ± 0.20 | 4.796 ± 0.052 | 3 |
| 19.00 ± 0.20 | 4.670 ± 0.049 | 10 |
| 19.57 ± 0.20 | 4.536 ± 0.046 | 13 |
| 19.85 ± 0.20 | 4.472 ± 0.045 | 4 |
| 20.22 ± 0.20 | 4.391 ± 0.043 | 5 |
| 20.96 ± 0.20 | 4.239 ± 0.040 | 4 |
| 21.06 ± 0.20 | 4.219 ± 0.040 | 4 |
| 21.89 ± 0.20 | 4.060 ± 0.037 | 4 |
| 22.76 ± 0.20 | 3.907 ± 0.034 | 10 |
| 23.70 ± 0.20 | 3.755 ± 0.032 | 8 |
| 23.95 ± 0.20 | 3.716 ± 0.031 | 4 |
| 24.32 ± 0.20 | 3.660 ± 0.030 | 3 |
| 24.70 ± 0.20 | 3.604 ± 0.029 | 14 |
| 25.54 ± 0.20 | 3.488 ± 0.027 | 3 |
| 26.12 ± 0.20 | 3.411 ± 0.026 | 1 |
| 26.52 ± 0.20 | 3.361 ± 0.025 | 1 |
| 26.81 ± 0.20 | 3.326 ± 0.025 | 1 |
| 27.07 ± 0.20 | 3.294 ± 0.024 | 1 |
| 27.48 ± 0.20 | 3.246 ± 0.023 | 1 |
| 27.71 ± 0.20 | 3.220 ± 0.023 | 1 |
| 29.11 ± 0.20 | 3.067 ± 0.021 | 2 |
| 29.36 ± 0.20 | 3.042 ± 0.020 | 2 |
| 29.61 ± 0.20 | 3.017 ± 0.020 | 2 |
| Prominent Peaks | | |
| 2.81 ± 0.20 | 31.451 ± 2.410 | 100 |
| 5.63 ± 0.20 | 15.688 ± 0.577 | 16 |

The skilled artisan recognizes that some variation is associated with 2-theta (2θ) measurements. Typically, 2θ values may vary from ±0.1 to ±0.2. The skilled artisan appreciates that such variation in values are greatest with low 2θ values, and least with high 2θ values. The skilled artisan recognizes that different instruments may provide substantially the same XRPD pattern, even though the 2θ values vary somewhat. Moreover, the skilled artisan appreciates that the same instrument may provide substantially the same XRPD pattern for the same or different samples even though the XRPD of the respectively collected XRPD patterns vary slightly in the 2θ values. Such slight variation can be caused, for example, by sample preparation techniques, different instruments used, instrument drift, and other experimental factors.

Diffraction peak lists may also be reported using $d_{hkl}$ (observed peak positions °2θ may be converted into $d_{hkl}$ values using Bragg's Law: $d_{hkl}=\lambda/2 \sin \theta$; Miller indices (hkl) of the diffraction peaks are determined from the published reference pattern, and when a reference pattern identifying (hkl) is unavailable, then "indexing" of the pattern is needed to determine the (hkl)) and relative intensity rather than 2θ and absolute intensity. The peak position as 2θ depends on instrumental characteristics such as wavelength. The peak position as $d_{hkl}$ is an intrinsic, instrument-independent material property. The absolute intensity, i.e., the number of X-rays observed in a given peak, can vary due to instrumental and experimental parameters. To calculate relative intensity, absolute intensity of every peak is divided by the absolute intensity of the most intense peak, and then converted to a percentage. The most intense peak of a phase is therefore called the "100% peak." Peak areas are a reliable measure of intensity.

The skilled artisan also appreciates that XRPD patterns of the same sample (taken on the same or different instruments) may exhibit variations in peak intensity at the different 2θ values. The skilled artisan also appreciates that XRPD patterns of different samples of the same polymorph (taken on the same or different instruments) may also exhibit variations in peak intensity at the different 2θ values. XRPD patterns can be substantially the same pattern even though they have corresponding 2θ signals that vary in their peak intensities.

In one embodiment, Form II exhibits an X-ray powder diffraction pattern having two or more (e.g., three or more, four or more, five or more, six or more, seven or more, eight or more, nine or more, or ten or more) characteristic peaks expressed in degrees 2θ (±0.2) at 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61 or having an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and DSC Thermogram substantially similar to that set forth in FIG. 4.

In another embodiment, Form II exhibits an X-ray powder diffraction pattern having three or more characteristic peaks expressed in degrees 2θ (±0.2) at 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61 or having an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and DSC Thermogram substantially similar to that set forth in FIG. 4.

In another embodiment, Form II exhibits an X-ray powder diffraction pattern having four or more characteristic peaks expressed in degrees 2θ (±0.2) at 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61 or having an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and DSC Thermogram substantially similar to that set forth in FIG. 4.

In another embodiment, Form II exhibits an X-ray powder diffraction pattern having characteristic peaks expressed in degrees 2θ (±0.2) at 2.81, 5.63, 19.00, 19.57, 22.76, and 24.70, or having an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and DSC Thermogram substantially similar to that set forth in FIG. 4, FIG. 15, FIG. 16, or FIGS. 22-24.

Figure 13:
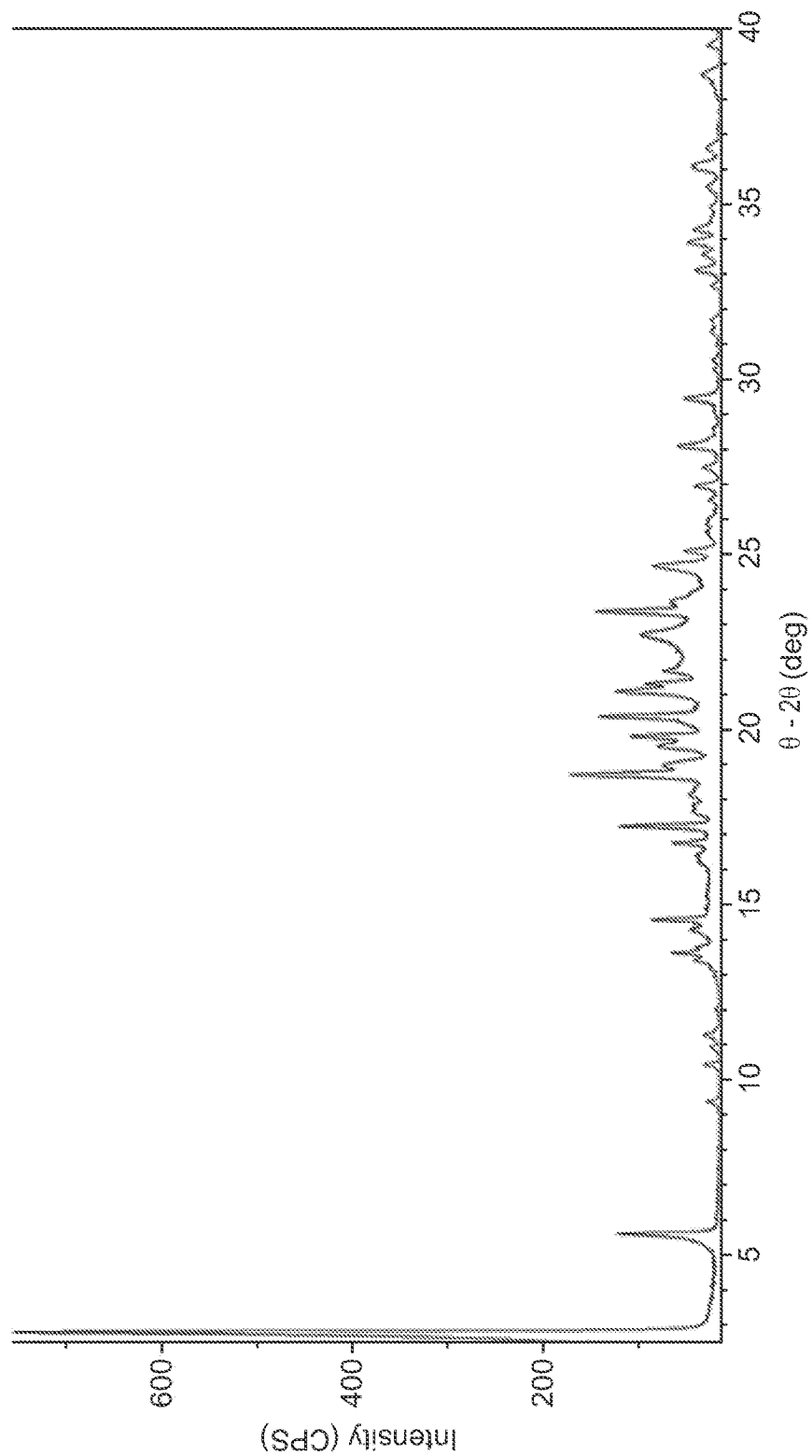
FIG. 13 shows XRPD of Form II, Tablet 1.
Figure 14:
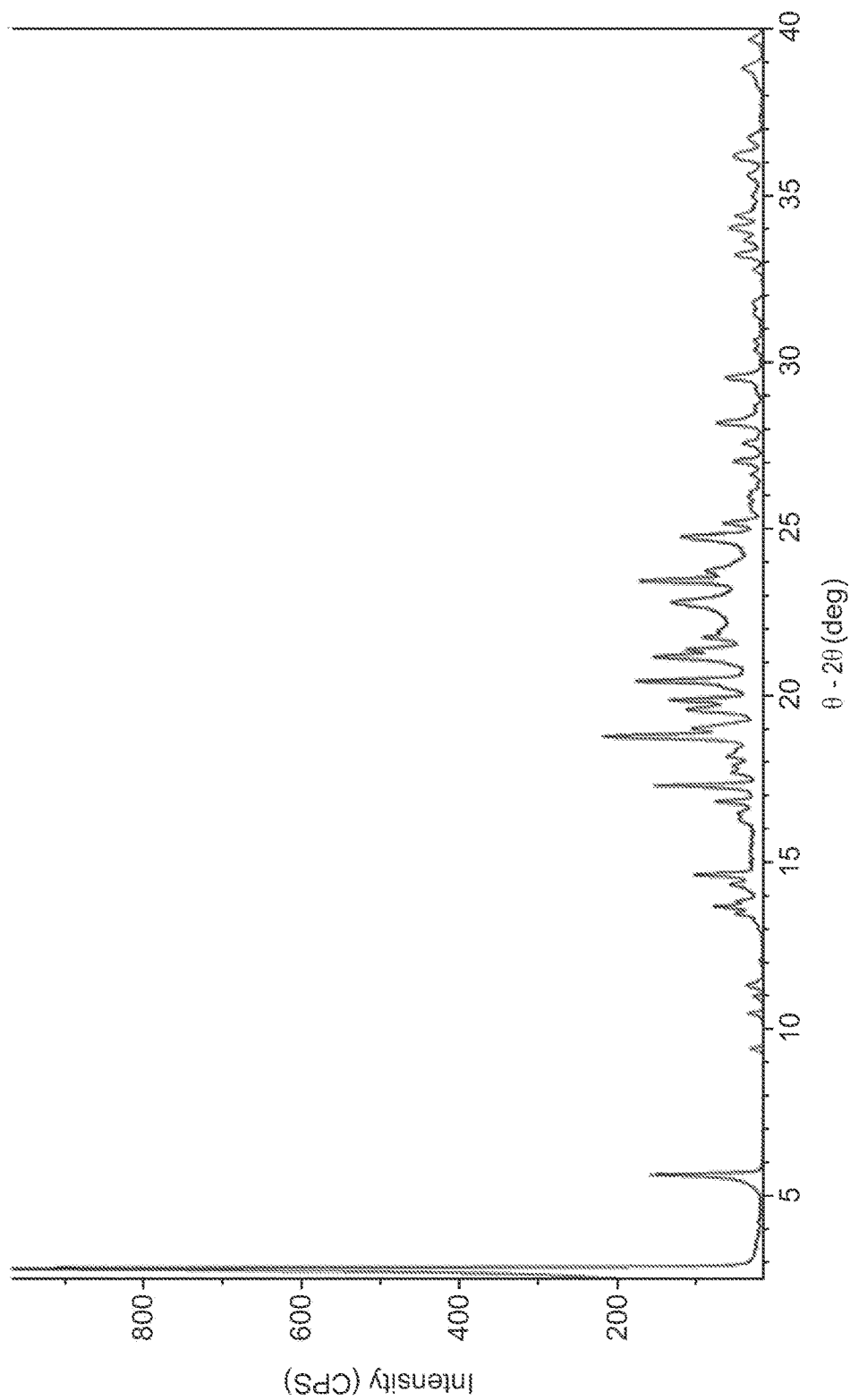
FIG. 14 shows XRPD of Form II, Tablet 2.
Figure 15:
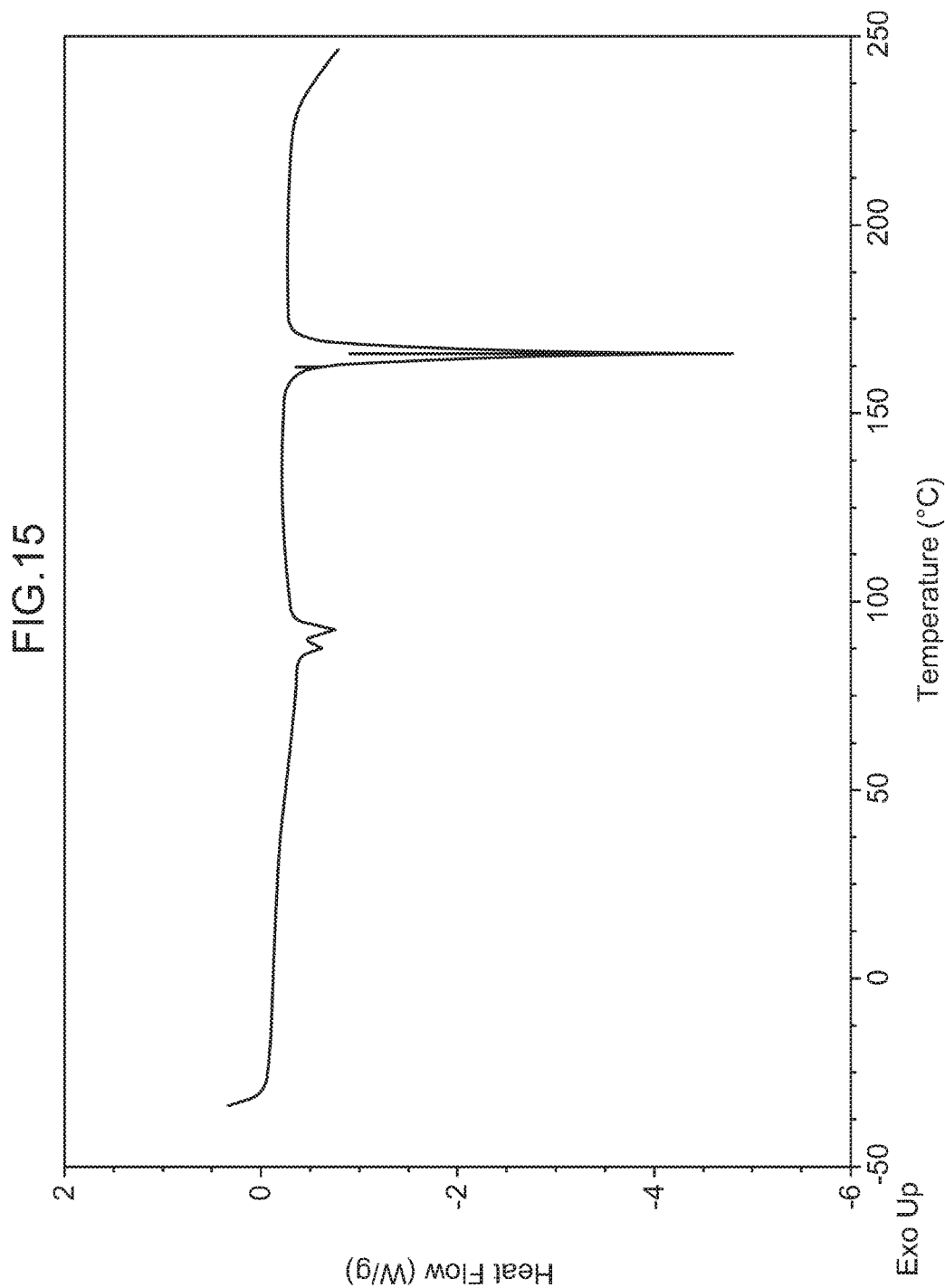
FIG. 15 shows DSC thermogram of Form II, Tablet 1. Endotherms are shown at about 90, 93, and 165° C.
Figure 16:
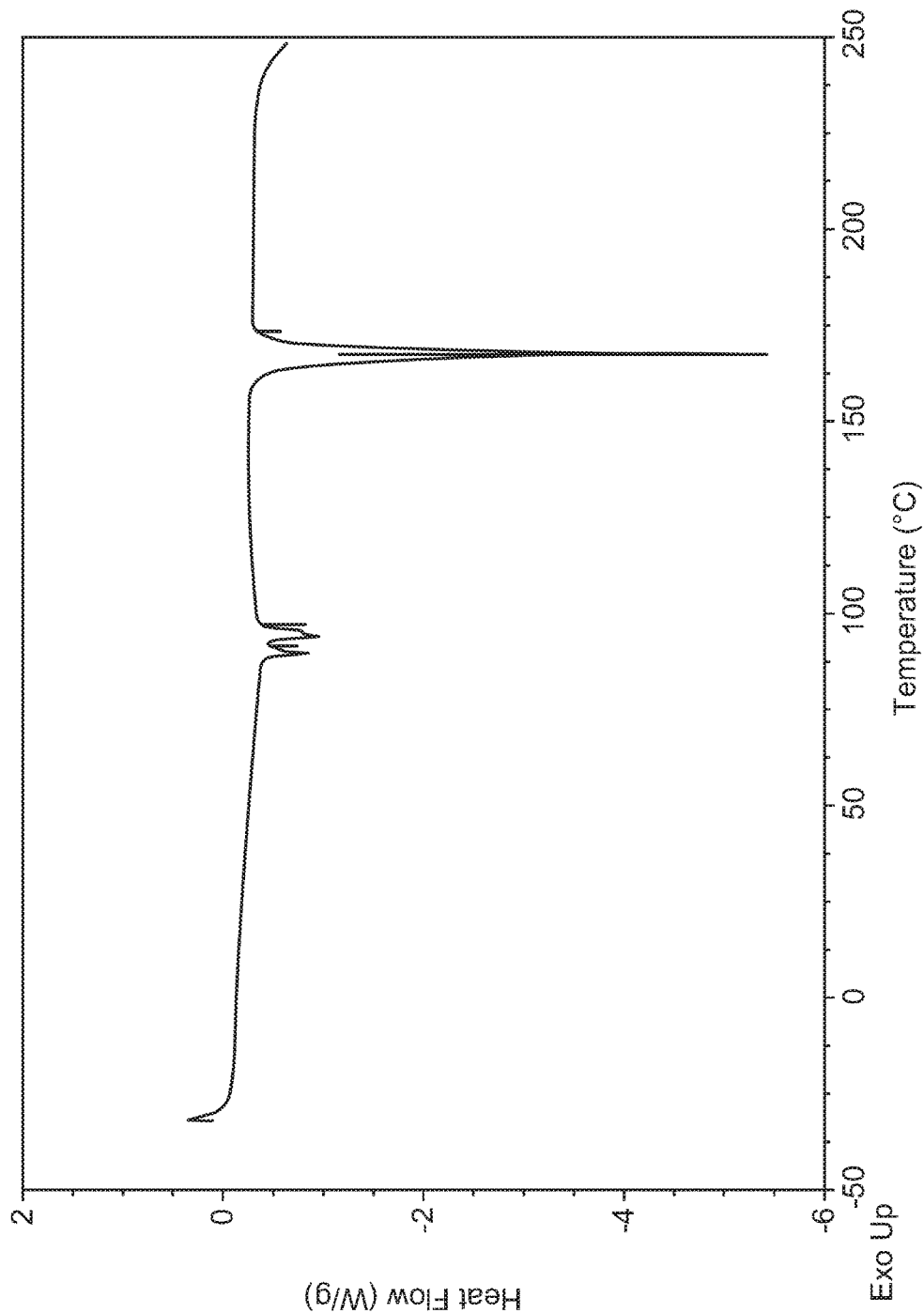
FIG. 16 shows DSC thermogram of Form II, Tablet 2. Endotherms are shown at about 89, 94, and 165° C.

In a particular embodiment, Form II exhibits an X-ray powder diffraction pattern having at least eight characteristic peaks expressed in degrees 2θ (±0.2), selected from the group consisting of at 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61 or having an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and DSC Thermogram substantially similar to that set forth in FIG. 4, FIG. 15, or FIG. 16.

In another particular embodiment, Form II exhibits an X-ray powder diffraction pattern having at least nine characteristic peaks expressed in degrees 2θ (±0.2), selected from the group consisting of at 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61 or having an X-ray diffraction pattern substantially similar to that set forth in FIG. 1, FIG. 7, FIG. 13, FIG. 14, FIG. 20, FIG. 21, or FIG. 25, indexing substantially similar to that set forth in FIG. 2, and DSC Thermogram substantially similar to that set forth in FIG. 4, FIG. 15, FIG. 16, or FIGS. 22-24.

In one or more embodiments, a composition comprising a compound of Form II lacks the XRPD peaks characteristic of Form H (e.g., at about 12.6° 2Θ) and/or Form I (e.g., at about 15.6° 2Θ).

XRPD Indexing

XRPD patterns are indexed using X-Pert High Score Plus (v.2.2.1). Indexing and structure refinement computational studies were performed. Agreement between the allowed peak positions and the observed peaks indicates a consistent unit cell determination. Successful indexing of a pattern indicates that the sample was composed primarily of a single crystalline phase. Space groups consistent with the assigned extinction symbol, unit cell parameters, and derived quantities are tabulated in the respective figures providing the indexing solution for each form. To confirm the tentative indexing solution, the molecular packing motifs within the crystallographic unit cells are determined.

XRPD Peak Identification

Under most circumstances, peaks within the range of up to about 30° 2Θ are selected. Rounding algorithms are used to round each peak to the nearest 0.1° or 0.01° 2Θ, depending upon the instrument used to collect the data and/or the inherent peak resolution. For d-space listings, the wavelength is used to calculate d-spacing was 1.541874 Å, a weighted average of the Cu—K$_{\alpha1}$ and Cu—K$_{\alpha2}$ wavelengths.

Variability associated with d-spacing estimates is calculated from the USP recommendation, at each d-spacing, and provided in the respective data tables. Per USP guidelines, variable hydrates and solvates may display peak variances greater than 0.2° 2Θ and therefore peak variances of 0.2° 2Θ were not applicable to these materials. For samples with only one XRPD pattern and no other means to evaluate whether the sample provides a good approximation of the powder average, peak tables contain data identified only as "Prominent Peaks." These peaks are a subset of the entire observed peak list. Prominent peaks were selected from observed peaks by identifying preferably non-overlapping, low-angle peaks, with strong intensity.

Differential Scanning Calorimetry (DSC) Thermogram

Form II may also be identified based on DSC, indexing, SEM, and/or particle size distribution. In some embodiments of the present disclosure, Form II is identifiable on the basis of a characteristic peak observed in a differential scanning calorimetry thermogram. Differential scanning calorimetry, or DSC, is a thermoanalytical technique in which the difference in the amount of heat required to increase the temperature of a sample and reference is measured as a function of temperature. In one embodiment, Form II exhibits a differential scanning calorimetry thermogram showing a characteristic minor endotherm at about 43° C. (peak max) followed by overlapping major endotherms at about 90 and about 95° C. (peak max). A final endotherm was observed with an onset at about 196° C. In another embodiment, Form II exhibits a differential scanning calorimetry thermogram substantially in accordance with FIG. 4.

In another embodiment of the invention, provided herein is Form II characterized as a solid form of Compound 1, such that the solid form undergoes a weight increase of less than 1.5% upon increasing relative humidity from 5.0% to 95.0%.

In one embodiment, Form II crystalline form of Formula II or III is prepared from a methanol crystallization using a slower cooling profile and no stirring. The DSC thermogram of Form II prepared using a slower cooling profile and no stirring has a minor endotherm at about 41° C., overlapping endotherms at about 90 and about 95° C. (peak max), and a final endotherm with an onset at about 200° C.

The present disclosure also provides a hydrate morphic Form H obtained from a method including water during crystallization. The hydrate morphic Form H has a DSC characteristics of having a minor endotherm around 41° C. (peak max), major endotherm at about 70° C. and about 103° C. (peak max) and a final endotherm at about 193° C. The TGA of the hydrate morphic Form H is about 0.93% weight loss from about 25° C. to about 100° C.

Scanning Electron Microscopy (SEM)

The present disclosure provides analysis of the crystals synthesized by the disclosed method by SEM. Samples for SEM are prepared by placing a small amount on a carbon adhesive tab supported on an aluminum mount. Each sample is then sputter coated with Au/Pd using a Cressington 108auto Sputter Coater at approximately 20 mA and 0.13 mbar (Ar). Each sample is observed under high vacuum using a beam voltage of 5.0 kV.

In some embodiments, SEM is performed using a FEI Quanta 200 scanning electron microscope equipped with an Everhart Thornley (ET) detector. Images are collected and analyzed using xTm (v. 2.01) and XT Docu (v. 3.2) software, respectively. The magnification is verified using a NIST-traceable standard. The sample is prepared for analysis by placing a small amount on a carbon adhesive tab supported on an aluminum mount. The sample is then sputter coated twice with Au/Pd using a Cressington 108auto Sputter Coater at approximately 20 mA and 0.13 mbar (Ar) for 75 seconds (FIGS. 26-32).

TABLE 7

Characteristics of morphic Form II

| | |
|---|---|
| XRPD | Crystalline; designated Form II |
| Indexing | Primitive Monoclinic<br>a = 7.537 Å, b = 6.729 Å, c = 62.555 Å, α = 90°, β = 90.54°, γ = 90° |
| DSC | Minor endo max. at ~43° C.;<br>overlapping endo at ~90° C. and ~95° C. (max). Endo onset at ~196° C. |
| SEM | Large agglomerates<br>(Agglomerates of plates and tablets (FIGS. 26-29)) |

TABLE 7-continued

Characteristics of morphic Form II

| XRPD | Crystalline; designated Form II |
|---|---|
| PSA (Sample 3) | d10 = 19.896 μm; d50 = 101.745 μm; d90 = 274.113 μm; bimodal distribution |
| $^1$H NMR | Consistent with Compound 1 structure; possibly contains residual acetone (wash solvent) (FIGS. 6-9) |

Purity

In certain embodiments, a sample of Form II contains impurities. Non-limiting examples of impurities include amorphous forms, other polymorph forms (e.g., H, I, and III), or residual organic and inorganic molecules such as related impurities (e.g., intermediates used to make Form II or fragments thereof), solvents, water or salts. In one embodiment, a sample of Form II is substantially free from impurities, meaning that no significant amount of impurities is present. In another embodiment, a sample of Form II contains less than 10% by weight total impurities. In another embodiment, a sample of Form II contains less than 5% by weight total impurities. In another embodiment, a sample of Form II contains less than 1% by weight total impurities. In yet another embodiment, a sample of Form II contains less than 0.1% by weight total impurities.

The present disclosure provides that an anhydrous form (e.g. Form II) is produced without forming a hydrate form (e.g., Form H) during the crystallization process, by determining the critical water concentration below which the anhydrous form is the stable form. The critical water concentration is determined by varying the methanol-water concentrations in the slurries.

In one embodiment, in sub-ambient slurries, at 99:1 methanol:water, Form II was recovered. In another embodiment, at concentrations of 97:3 methanol:water and greater, Form H was recovered from the slurries. These embodiments provide that the critical water concentration for forming Form II is between 1 and 3% water. In some embodiments, water in the initial methanol solvent is not accounted for, which results in slightly higher final water concentration than 1 and 3%. In additional embodiments, experiments, by varying the methanol-water concentrations in the slurries, is carried out at room temperature or at about 45° C. In one embodiment, the critical water concentration is less than 5% at room temperature and less than 10% at about 45° C. Mixtures of Form II and Form H are observed to convert to either Form II or Form H in methanol depending on the exact water content. The present disclosure provides that during crystallization of Form II, critical water activity remains very low up to about 45° C. and that water content in the final methanol recrystallization is a critical process parameter to control to avoid operating in conditions which favors formation of Form H.

In certain embodiments, a sample of Form II is a crystalline solid substantially free of amorphous compound of Formula II or III. As used herein, the term "substantially free of amorphous compound of Formula II or III" means that the compound contains no significant amount of amorphous compound of Formula II or III. In another embodiment, a sample of crystalline compound of Formula II or III comprises Form II substantially free of Form I and/or H. As used herein, the term "substantially free of Form I and/or H" means that a sample of crystalline compound of Formula II or III contains no significant amount of Form I and/or H. In certain embodiments, at least about 90% by weight of a sample is Form II, with only 10% being Form I and/or H and/or amorphous compound of Formula II or III. In certain embodiments, at least about 95% by weight of a sample is Form II, with only 5% being Form I and/or H and/or amorphous compound of Formula II or III. In still other embodiments of the invention, at least about 99% by weight of a sample is Form II, with only 1% by weight being Form I and/or H and/or amorphous compound of Formula II or III. In still other embodiments of the invention, at least about 99.5% by weight of a sample is Form II, with only 0.5% by weight being Form I and/or H and/or amorphous compound of Formula II or III. In still other embodiments of the invention, at least about 99.9% by weight of a sample is Form II, with only 0.1% by weight being Form I and/or H and/or amorphous compound of Formula II or III.

Form II may occur as any reasonable tautomer, or a mixture of reasonable tautomers. As used herein, "tautomer" refers to one of two or more structural isomers that exist in equilibrium and are readily converted from one isomeric form to another.

In some embodiments, the process of recrystallizing Compound 1 (e.g., Formula II or Formula III) results in a Compound 1 that is largely free of impurities. In some embodiments, Compound 1 is >95% pure, >96% pure, >97% pure, >98% pure, >99% pure, >99.5% pure, >99.9% pure, or >99.99% pure. The purity can be measured by a variety of different techniques known in the art such as high-performance liquid chromatography (HPLC). For instance, in some preferred embodiments, Compound 1 is recrystallized once from methanol and heptane, followed by three subsequent recrystallizations from methanol; Form II is only seeded during the third and final methanol recrystallization.

Figure 27:
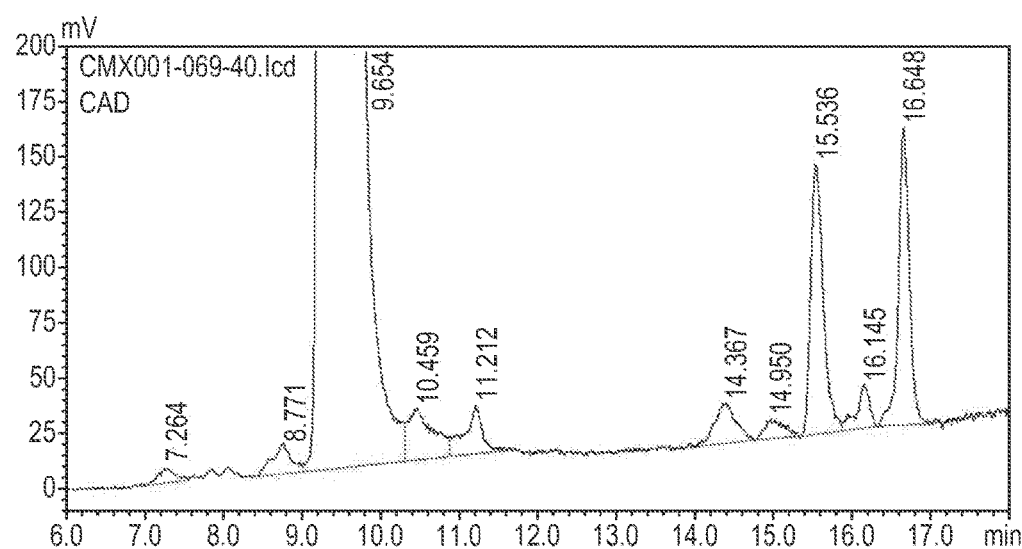
FIG. 27 shows a chromatogram of Compound 1 after two fast cool-down methanol recrystallizations. The chromatogram shows that Compound 1 is 98.5% pure.

The recrystallization protocol for Compound 1 (e.g., Compound 1 Form II) can impact the relative purity of the Compound 1. For instance, FIG. 27 shows a CAD (Charged Aerosol Detection) chromatogram of Compound 1 after two fast-cool-down methanol recrystallizations. For instance, the Compound 1 is 98.5% pure. As indicated in FIG. 27.

Figure 28:
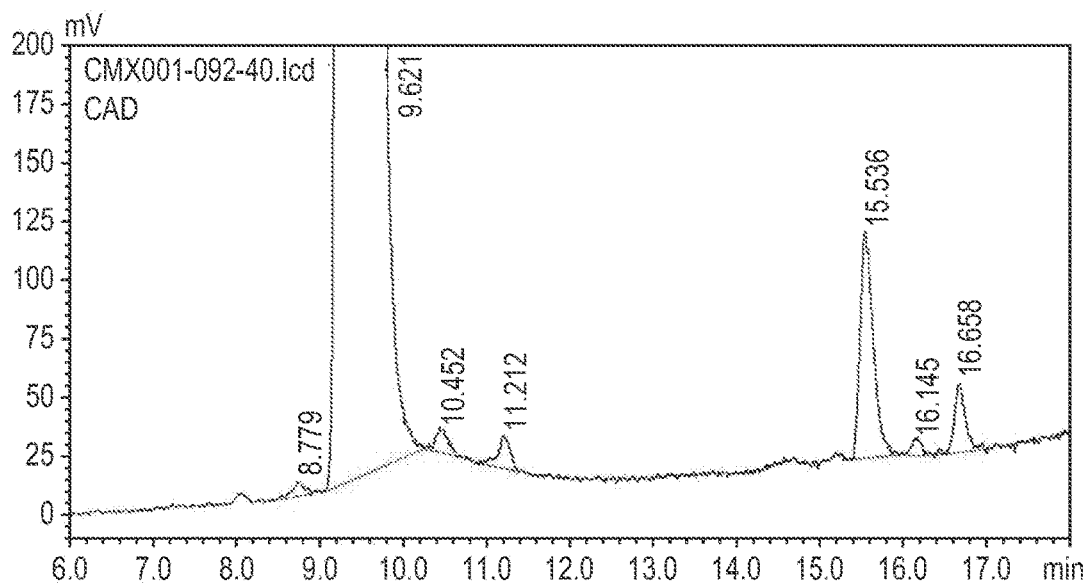
FIG. 28 shows a chromatogram of Compound 1, Form II after three slow-cool down methanol recrystallizations with form control. The chromatogram shows that Compound 1 is 99.5% pure.

FIG. 28 shows a CAD chromatogram of Compound 1 after three slow cool-down recrystallizations in methanol. As shown in FIG. 28, the Compound 1 is 99.5% pure.

Figure 29:
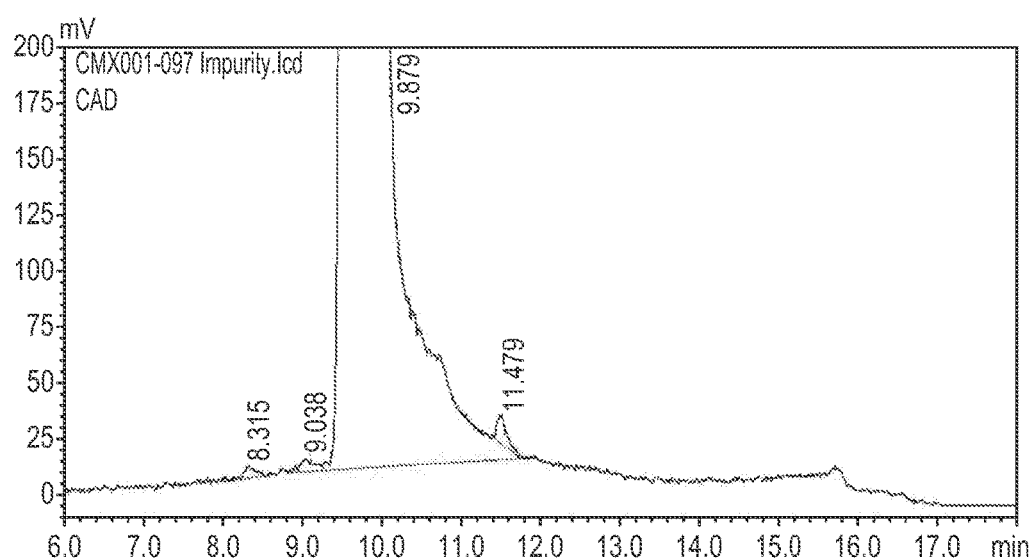
FIG. 29 shows a chromatogram of Compound 1, Form II after one heptane/methanol recrystallization followed by one methanol slow cool-down recrystallization for form control. The chromatogram shows that Compound 1 is 100% pure.

FIG. 29 shows a CAD chromatogram of Compound 1 after one recrystallization in heptane/methanol followed by one slow cool-down recrystallization in methanol. The compound is 100% pure as shown in FIG. 29.

Figure 30:
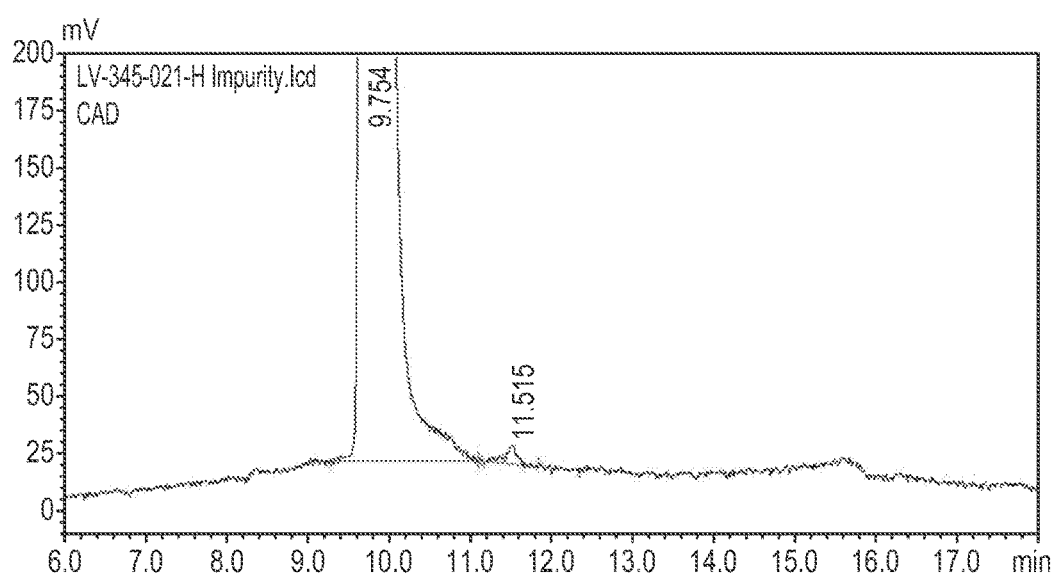
FIG. 30 shows a chromatogram of Compound 1, Form II after a heptane/methanol recrystallization followed by three methanol recrystallizations. The chromatogram shows that Compound 1 is 100% pure.

FIG. 30 shows a CAD chromatogram of Compound 1 after a preferred embodiment comprising one recrystallization from heptane/methanol followed by three recrystallizations from methanol. As shown in FIG. 30, the purity of Compound 1 is 100%. This recrystallization process is explained in more detail in Example 3 and is a preferred purification protocol.

Accordingly, in some preferred embodiments, the process of purifying the Compound 1 comprises five distinct recrystallization procedures: three methanol recrystallizations without seeding, one n-heptane/methanol recrystallization, and one methanol recrystallization with seeding. In some embodiments, the first three methanol recrystallizations remove impurities such as residual amounts of the following compounds (i.e., Compounds A and B):

Compound A

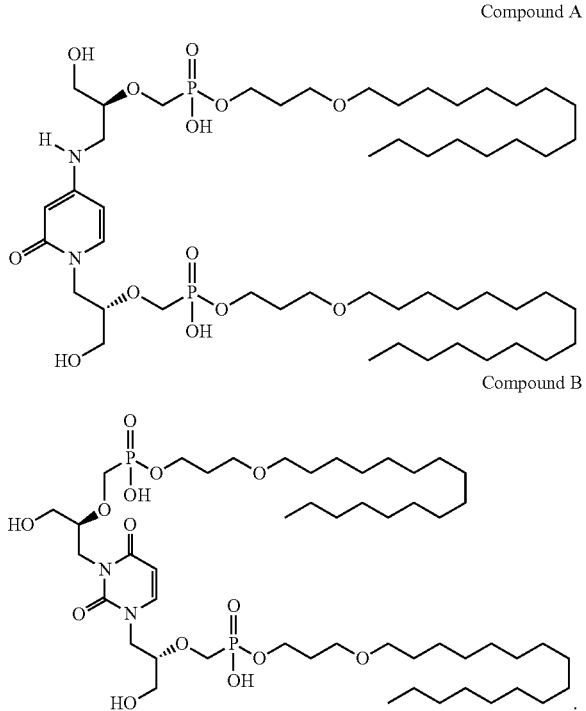

Compound B

In some embodiments, the above compounds can be substantially difficult to remove from the compositions comprising Compound 1 by other means (e.g., chromatography). Accordingly, in some embodiments, it is advantageous to perform at least one recrystallization from methanol as a first recrystallization procedure in order to remove the above impurities.

The recrystallization using n-heptane and methanol removes the impurities detectable by CAD and shown in FIGS. 27 and 28. In some embodiments, the CAD-detectable impurities can be, for instance, the following compounds (i.e., Compounds C and D):

Compound C

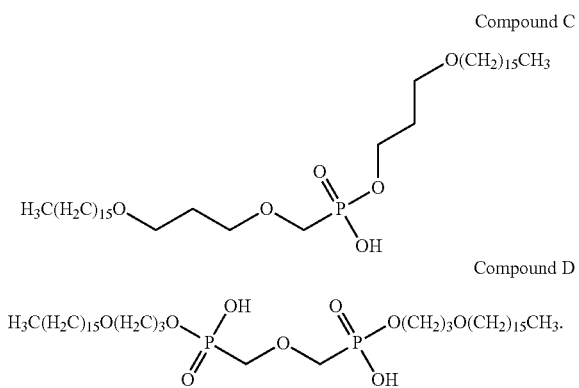

Compound D

Accordingly, in some embodiments in the absence of performing the above recrystallizations, the compounds shown above will be present in the composition comprising Compound 1. The above compounds in any combination can be present in low quantities (e.g., <2% by weight, or <1% by weight).

In some embodiments, the present invention includes a composition comprising Form II and various other morphic forms. The other morphic forms can include Form I and Form H. In some embodiments, the composition includes >90% Form II. In some embodiments, the composition includes >95% Form II. In some embodiments, the composition includes >99% Form II. Alternatively, in some embodiments, the composition includes <10% of Form I and/or Form H. In some embodiments, the composition includes <5% of Form I and/or Form H. In some embodiments, the composition includes <1% of Form I and/or Form H.

In some embodiments, the present invention includes a composition comprising Compound 1 and other impurities. In some embodiments, the impurities are selected from Compounds A-D. In some embodiments, the present invention includes a composition comprising >90% Compound 1. In some embodiments, the present invention includes a composition comprising >95% Compound 1. In some embodiments, the present invention includes a composition comprising >99% Compound 1. In some embodiments, the present invention includes a composition comprising <10% impurities selected from Compounds A-D. In some embodiments, the present invention includes a composition comprising <5% impurities selected from Compounds A-D. In some embodiments, the present invention includes a composition comprising <1% impurities selected from Compounds A-D.

Co-Crystals

The present disclosure provides co-crystals of Form II of Formula II or III. The co-crystals of the present disclosure may be a pharmaceutically acceptable salt of Formula II or III, a solvate (a crystal structure incorporating either stoichiometric or non-stoichiometric amounts of a solvent), hydrate (a crystal structure incorporating either stoichiometric or non-stoichiometric amounts of water), clathrate (molecules of one substance are completely enclosed with the crystal structure of another), and/or molecular complex (a unique crystal structure incorporating stoichiometric amounts of more than one molecule).

Co-crystal may be formed with citric acid, fumaric acid, gentisic acid, hippuric acid, maleic acid, L-mandelic acid, orotic acid, oxalic acid, saccharin, succinic acid, L-tartaric acid, toluenesulfonic acid, ammonia, L-arginine, calcium hydroxide, diethylamine, diethylaminoethanol, ethylenediamine, 1H imidazole, L-lysine, 2-hydroxyethylmorpholine, N-methyl-glucamine, potassium methanolate, zinc tert-butoxide. The salt/co-crystal screening included the evaporation from four solvents followed by the phase equilibration in four further solvents.

Method of Synthesis Morphic Form II

The present invention provides methods for the synthesis of the compounds of Formulae I, II, and/or II. The present invention also provides detailed methods for the synthesis of various disclosed compounds of the present invention according to the following schemes and as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or derivative thereof.

Scheme 1 (Steps 1, 2A and 2B): Synthesis of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1).

In one embodiment, the present disclosure provides a method of producing morphic Form II of the compound of formula II or formula III, or a pharmaceutically acceptable salt thereof. The method provides a purification process including recrystallizing a preparation of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1) from methanol.

The present disclosure provides a method for synthesizing a morphic Form II of Compound 1, including the steps 1 and 2.

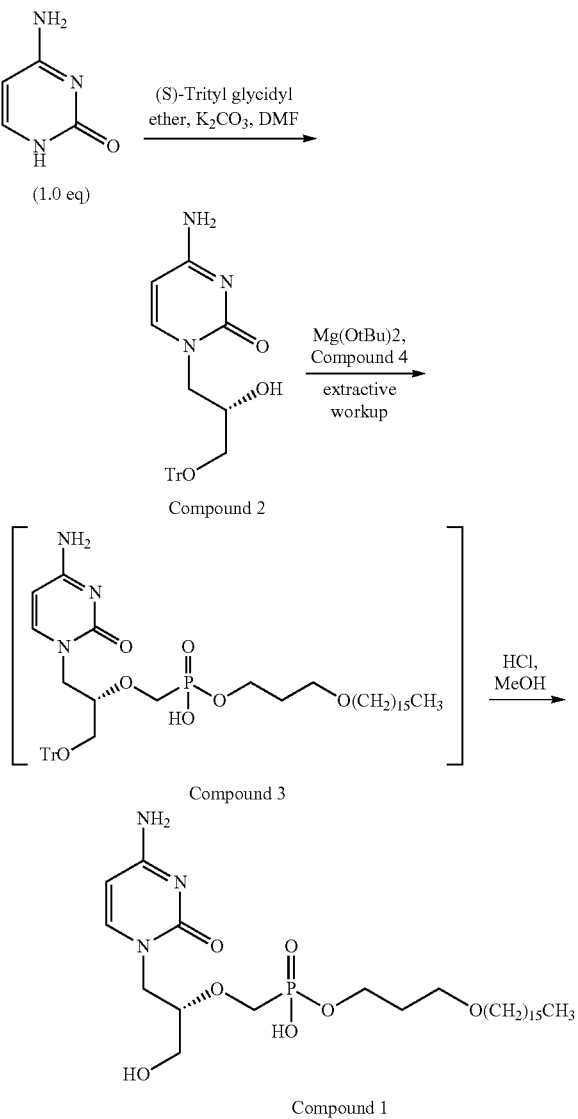

Scheme 1

Compound 2

Compound 3

Compound 1

Step 1: Synthesis of (S)—N$^1$-[(2-hydroxy-3-triphenylmethoxy)propyl] cytosine (Compound 2)

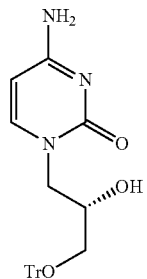

(S)—N$^1$-[(2-hydroxy-3-triphenylmethoxy)propyl] cytosine (Compound 2) is synthesized by contacting cytosine with (S)-trityl glycidyl ether (syn. (S)-GLYCIDYL TRITYL ETHER; Trityl-(s)-glycidyl ether; (S)-TRITYL GLYCIDYL ETHER; (S)-(−)-TRITYL GLYCIDYL ETHER; (S)-(−)-GLYCIDYL TRITYL ETHER; Triphenylmethyl glycidyl ether; (S)-2-((trityloxy)methyl)oxirane; (S)-(−)-Glycidyl Trityl Esther; (S)-GLYCIDYL TRIPHENYLMETHYL ETHER; (S)-2-(TRIPHENYLMETHOXYMETHYL)OXIRANE) in the presence of a suitable base such as a metal carbonate (e.g., potassium carbonate) in a suitable organic solvent (e.g., N, N-dimethylformamide (DMF) or tert-amyl alcohol) in a suitable reaction temperature (e.g., about 85 to about 95° C. or about 60 to about 120° C.) until completion of reaction for between about 4 to 14 hours, e.g., about 8 to 10 hours. In one embodiment, the reaction can be heated at a temperature between about 85 to about 95° C. for about 9 hours.

The heated reaction mixture is then cooled. In one embodiment, the heated reaction mixture is cooled to, e.g., about 50-75° C. or about 66-70° C., and quenched with a substituted benzene derivative, e.g., a mono-substituted benzene derivative such as toluene. The resulting slurry is further cooled to a temperature, e.g., between below or close to 0° C., e.g., to about −10 to 5° C. The cooled slurry is then filtered, washed with a substituted benzene derivative, e.g., a mono-substituted benzene derivative such as toluene. The solids obtained after washing in a substituted benzene derivative, e.g., a mono-substituted benzene derivative such as toluene, is then made into a slurry at a suitable temperature, e.g., about 15-25° C., before the slurry is filtered. The cooled slurry is then washed with an organic solvent such as a ketone, e.g., acetone (propanone).

The solid is then purified by trituration in water/acetone at a suitable ratio (e.g., 90.0 kg/54.0 kg) at a suitable temperature, e.g., about 17-22° C., filtered, and washed with an organic solvent such as a ketone, e.g., acetone (propanone) (e.g., about 36.0 kg). The embodiments provide that the filter cake obtained after the filtration step is then suspended in an organic solvent such as a ketone, e.g., acetone (propanone) (e.g., about 178.9 kg) and heated, e.g., at approximately 35-45° C. for more than 1 hour, e.g., equal to or more than about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 hours, and then filtered, and washed with an organic solvent such as a ketone, e.g., acetone (propanone) (e.g., about 36.0 kg). The washes and triturations are repeated as needed to remove residues and/or impurities, e.g., residual cytosine and/or process-related impurities. The cake is dried in vacuo at equal to or less than about 40° C. for several hours, e.g., 12 hours, to yield about 45.0 kg (about 65.0%) of Compound 2. In some embodiments, purity of the yield is more than about 99% (as determined by HPLC (AUC)). In one embodiment, $^1$H-NMR of the product is consistent with the standard structure of Compound 2.

Steps 2A and 2B: Synthesis of Phosphonic Acid, [[(S)-2-(4-amino-2-oxo-1(2H)-pyrimidinyl)-1-(hydroxymethyl) ethoxy]methyl]mono[3-(hexadecyloxy)propyl] ester (Compound 1), Having the Formula

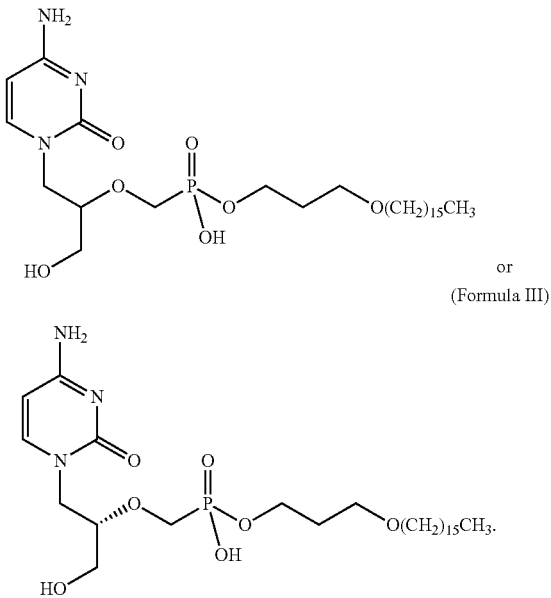

(Formula II)

or (Formula III)

The Formula II or III compound is prepared by contacting Compound 2 with Compound 4 in the presence of a suitable base such as a metal alkoxide (e.g., magnesium di-tert-butoxide, sodium tert-butoxide, lithium tert-butoxide, sodium tert-amyl alkoxide, potassium tert-butoxide, sodium methoxide), metal hydride (e.g., sodium hydride, potassium hydride), or metal amide (e.g., lithium bis(trimethylsilyl) amide) in a suitable organic solvent (e.g., N, N-dimethylformamide, N, N-dimethylacetamide, dimethylsulfoxide, 1-methyl-2-pyrrolidinone) at a suitable reaction temperature (e.g., 50 to 110° C.) until completion of reaction, which is about 0.25 to five hours, e.g., about two to four hours. The crude reaction mixture is subjected to an aqueous work-up. The crude product is extracted with a suitable organic solvent (e.g., ethyl acetate, isopropyl acetate, dichloromethane, etc.) and the organic solvent is concentrated to give crude Compound 3. The concentrate containing Compound 3 is diluted in methanol and reconcentrated to remove residual organic solvent (e.g., ethyl acetate, isopropyl acetate, dichloromethane, etc.). The crude Compound 3 is contacted with a suitable deprotecting agent (e.g., hydrogen chloride, acetyl chloride) in an organic solvent (e.g., methanol) until completion of reaction, for one or more hours, e.g., one to six hours. In one embodiment, Compound 3 is contacted with a suitable deprotecting agent (e.g., hydrogen chloride, acetyl chloride) in an organic solvent (e.g., methanol) until completion of reaction for two to three hours. The crude Compound 1 is recrystallized using a suitable solvent system (e.g., methanol/acetone/water, ethanol, methanol).

In one embodiment a mixture of (S)—N$^1$-[(2-hydroxy-3-triphenylmethoxy)propyl]cytosine (Compound 2), P-[[[4-methylphenyl)sulfonyl]oxy]methyl]-, mono[3-(hexadecyloxy)propyl]ester (Compound 4), magnesium tert-butoxide, and a polar (hydrophilic) aprotic solvent, e.g., dimethylformamide (DMF), is heated at a suitable temperature, e.g., between about 75-85° C. for more than 1 hour, e.g., equal to or more than about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0 hours. Other polar aprotic solvent such as tetrahydrofuran, ethyl acetate, acetone, acetonitrile, or dimethyl sulfoxide is also used in the mixture.

The mixture solution is then cooled to a suitable temperature, e.g., about 25-35° C., before adding an organic solvent, e.g., an ester such as isopropyl acetate (1-Methylethyl acetate). The solution is then further cooled to a suitable temperature, e.g., about 15-25° C. before washing sequentially with an acid solution, e.g., HCl solution, and a salt solution, e.g., NaCl solution.

The organic solvent e.g., an ester such as isopropyl acetate (1-Methylethyl acetate) is removed by vacuum distilling the organic phase to form a concentrate. The concentrate is then diluted with an alcohol (e.g., methanol) to further remove isopropyl acetate and to re-concentrate and form a mixture containing phosphonic acid, [[(S)-2-(4-amino-2-oxo-1(2H)-pyrimidinyl)-1-(hydroxymethyl)-2-(triphenylmethoxy) ethyl]methyl]mono[3-(hexadecyloxy)propyl]ester (Compound 3). The temperature is maintained between about −5 and 15° C. by the addition of HCl gas at a desired rate. The reaction is maintained below about 10-20° C. for more than 1 hour, e.g., about 2 hours, before it is filtered to remove solid impurities. The filtrate is then diluted with water and pH is then adjusted to about 2.3-2.7 with NaOH. The solids are filtered and washed with water before a slurry is prepared in an organic solvent such as a ketone, e.g., acetone (propanone) at about 35-45° C. for about 1 hour. The slurry is then filtered and washed with an organic solvent such as a ketone, e.g., acetone (propanone). The organic solvent such as a ketone, e.g., acetone (propanone) washed crude product is then dried at equal to or less than about 40° C. for several hours, e.g., about 12 hours and heated at about 60-70° C. in alcohol (e.g., methanol). The dried crude product is then polish filtered, cooled to about 58-62° C., stirred for one hour, cooled to first about 48-52° C. for about six hours, then to about 17-23° C. for two hours, filtered, and then washed with alcohol (e.g., methanol). The washing, drying, polish filtering, cooling, and the final filtering and washing steps may be repeated one or more times to dissolve solids in alcohol (e.g., methanol) before the sample is cooled to, e.g., about 59-61° C. The cooled product is then stirred for several minutes, e.g., about 20 minutes. To this solution a seed stock of phosphonic acid, [[(S)-2-(4-amino-2-oxo-1 (2H)-pyrimidinyl)-1-(hydroxymethyl) ethoxy]methyl]mono [3-(hexadecyloxy)propyl] ester (e.g. seed stock of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 8.0%, about 9.0%, about 10.0%, about 0.1-0.2%, about 0.2-0.3%, about 0.3-0.4%, about 0.4-0.5%, about 0.5-0.6%, about 0.6-0.7%, about 0.7-0.8%, about 0.8-0.9%, about 0.9-1.0%, about 1.0-2.0%, about 2.0-3.0%, about 3.0-4.0%, about 4.0-5.0%, about 5.0-6.0%, about 6.0-7.0%, about 7.0-8.0%, about 8.0-9.0%, about 9.0-10.0%, about 7.0-8.0%, about 8.0-9.0%, or about 9.0-10.0% of Form I, Form II, or Form H) is added and then stirred for more than 1 hour, e.g., about 2 hours, and then the solution is cooled to about 47° C.-53° C. by stirring for about several hours, e.g., 8 hours, and then stirred for about more than one hour, e.g., about 2 hours. The seed is added at a temperature between about 50° C.-65° C. (e.g., 56° C.-61° C.). The stirred solution is then further cooled to about 17-23° C. over at least about 1 hour, e.g., about 6 hours or more, and further stirred for about 2 hours; filtered and washed with methanol; dried at about equal to or less than 40° C. for about 24 hours. The method of the present disclosure thereby provides synthesis of morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester (Compound 1).

Figure 3:
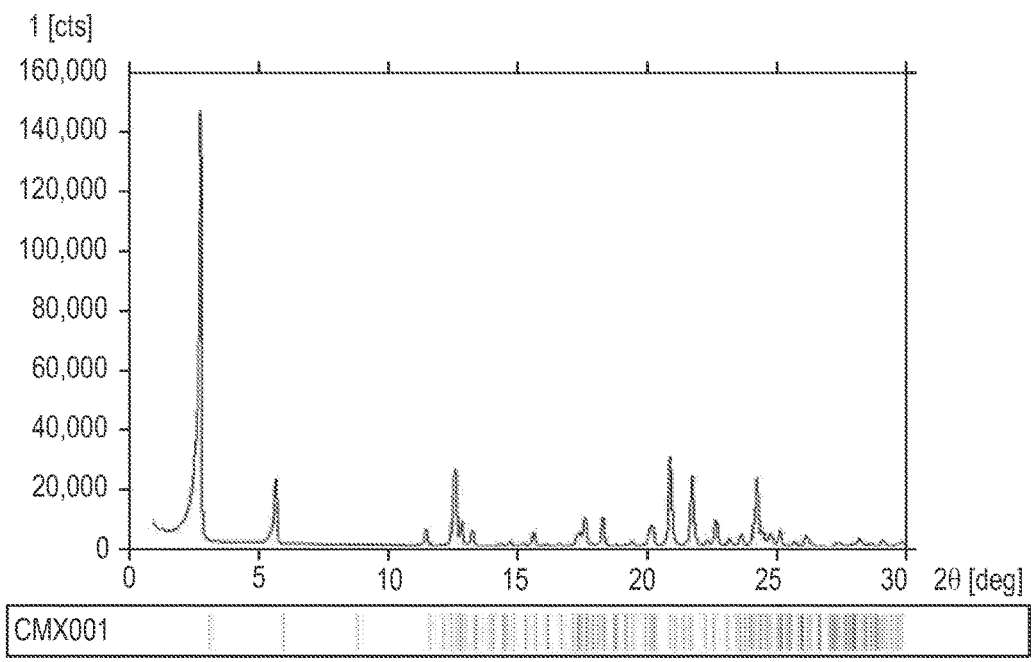
FIG. 3 shows indexing results of Compound 1 Form H for XRPD collected with Cu-Kα radiation.

In some embodiments, a composition of morphic Form II can include the corresponding hydrate (i.e., Form H). In some embodiments, a composition of Form II has trace amounts (e.g., <1.5%, <1%, <0.5%, <0.4%, <0.3%, <0.2%, <0.1%, or 0.01% of Form H (e.g., the composition is substantially free of Form H). For instance, the XRPD pattern of Compound 1 shown in FIG. 20 exhibits sharp peaks indicating the sample is composed of crystalline material. The pattern is similar to sample 1 of Form II in terms of peak positions (see e.g., FIG. 1), suggesting the sample is composed of Form II. However, the peak at ~12.6° 2Θ may be due to the presence of a small amount of Compound 1, Form H (see e.g., FIG. 3).

Figure 22:
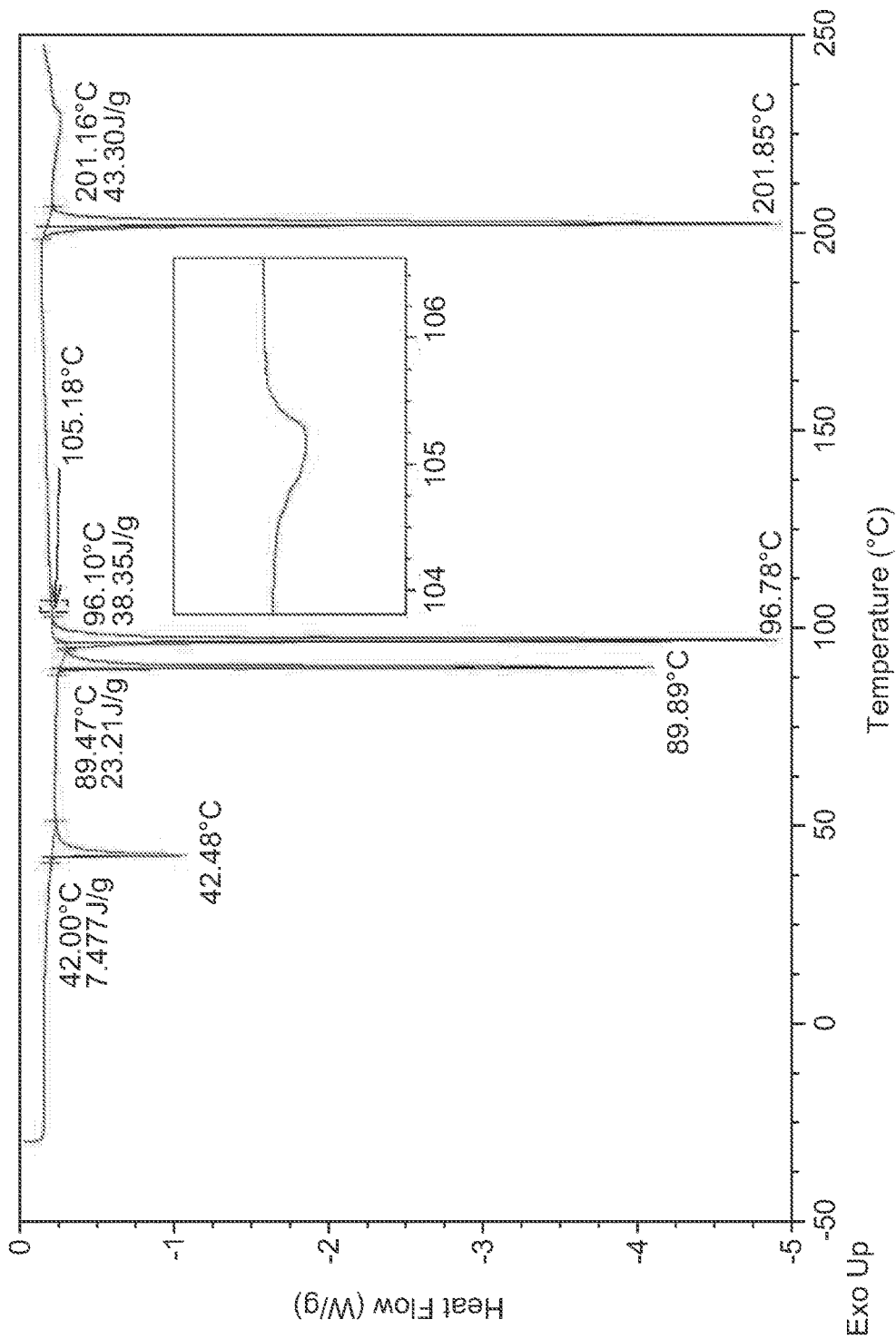
FIG. 22 shows DSC thermogram of Compound 1, Form II (sample 3).
Figure 23:
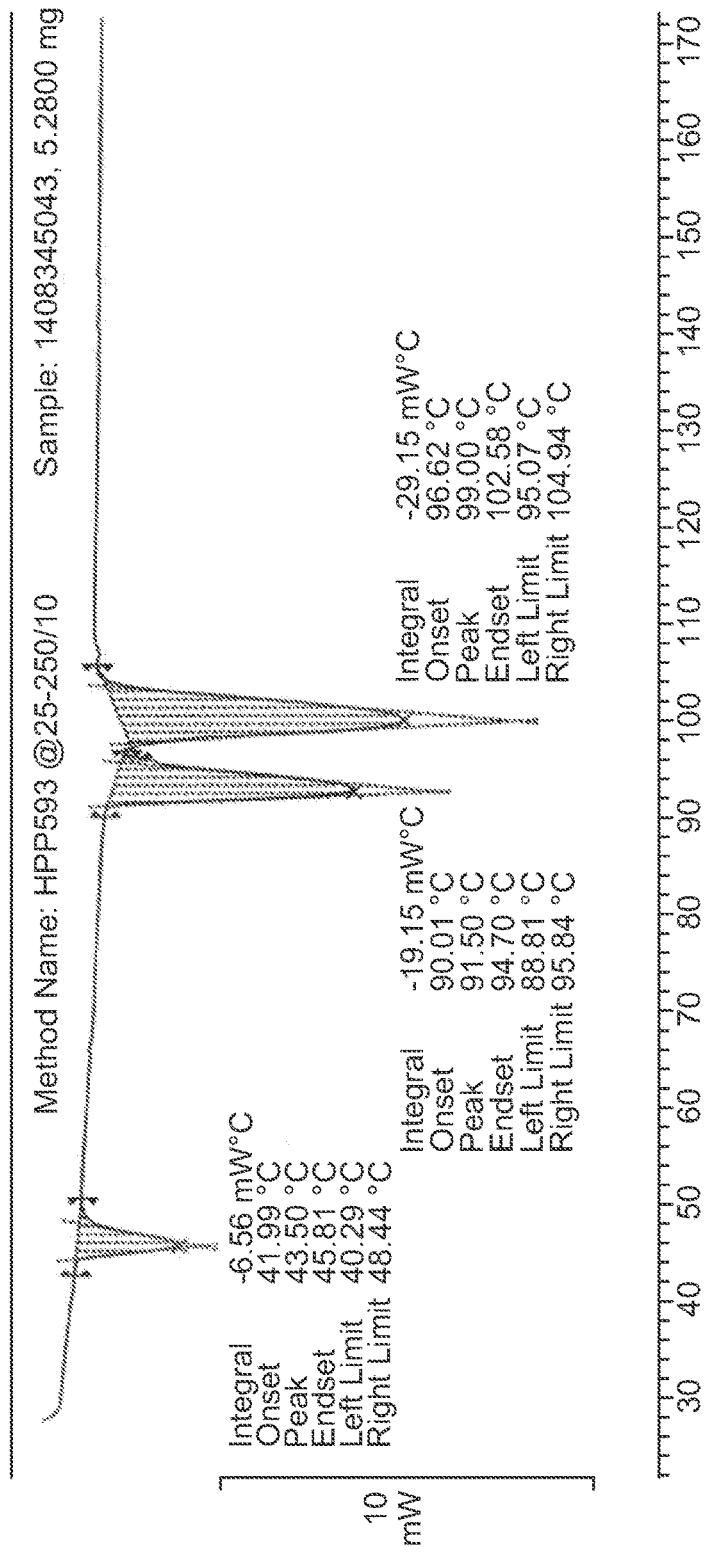
FIG. 23 shows a close-up DSC thermogram of Compound 1, Form II (sample 3).
Figure 24:
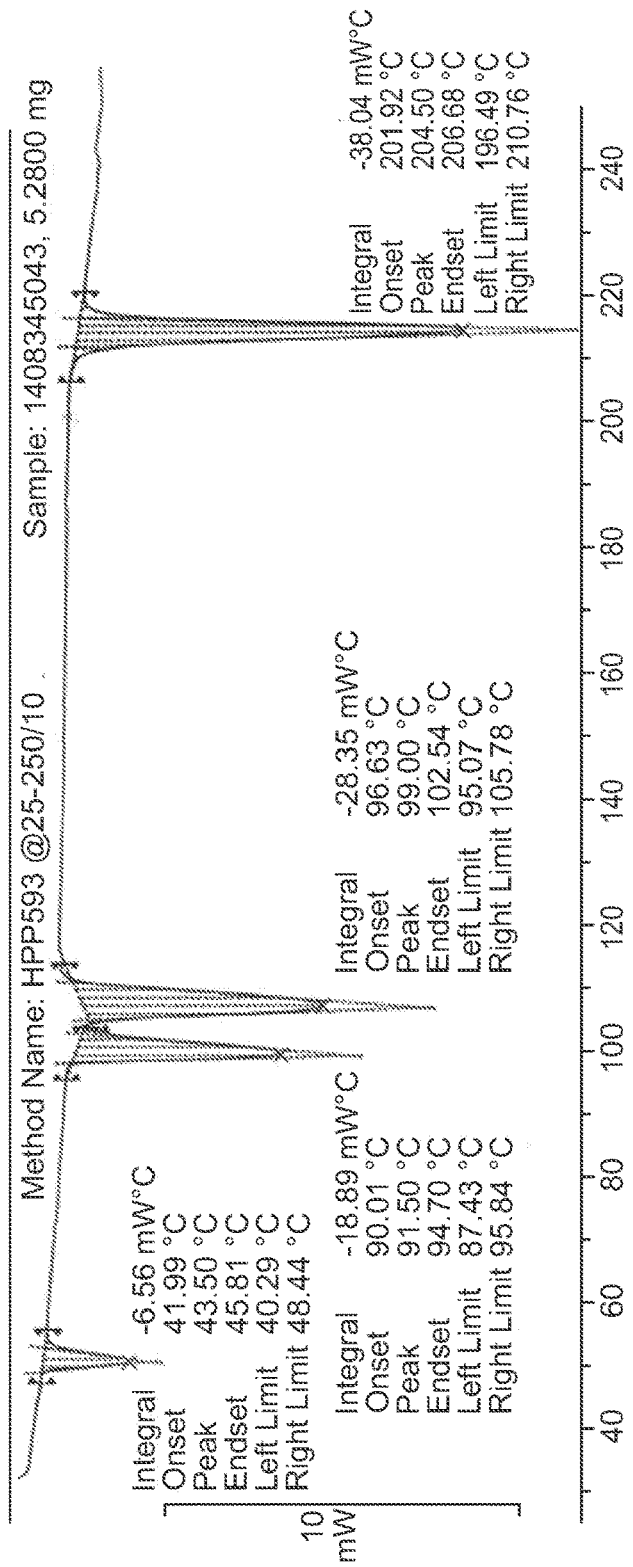
FIG. 24 shows another DSC thermogram of Compound 1, Form II (sample 3).

In some embodiments (for instance, sample 3), The DSC thermogram of Form II can display a small endotherm with a maximum at ~42° C. (onset ~42° C.), overlapping endotherms with maxima at ~90° C. and ~97 (onsets ~89 and 96° C., respectively), and an endotherm at ~202° C. (onset ~201° C.) (see e.g., FIG. 22-24). The thermogram is similar to sample 1 of Compound 1, Form II (FIG. 4). However, a minor endotherm is observed at 105° C. in the scan of sample 3, Form II (FIGS. 22-24). This may be due to the presence of a minor amount of Form H.

For instance, sample 3 of Compound 1, Form II has the following DSC profile: small, sharp endotherm: maximum ~42° C. (onset ~42° C.); Overlapping sharp endotherms: maxima ~90° C. (onset ~89° C.); maxima ~97° C. (onset ~96° C.); Minor endotherm: ~105° C.; Sharp endotherm: maximum ~202° C. (onset ~201° C.). This profile is consistent with Form II plus an additional trace amount of a minor endotherm ~105° C. which can be due to the presence of a trace amount of Form H.

The present disclosure provides more than about 99% wt/wt pure morphic Form II of a compound having Formula II or III, or a pharmaceutically acceptable salt thereof. In some embodiments, a composition comprising the morphic Form II of a compound having Formula II or III, or a pharmaceutically acceptable salt thereof is equal to or more than about 99% wt/wt, about 98% wt/wt, about 97% wt/wt, about 96% wt/wt, about 95% wt/wt, about 94% wt/wt, about 93% wt/wt, about 92% wt/wt or about 91% wt/wt, pure. In some embodiments, the present disclosure provides a non-hydrate morphic Form II of a compound having Formula II or III, or a pharmaceutically acceptable salt thereof. In some embodiments, a composition comprising the morphic Form II of the present disclosure is equal to or less than about 5 mg/mL, about 4 mg/mL, about 3 mg/mL, about 2 mg/mL, or about 1 mg/mL soluble in 1:1 methanol:water ratio at room temperature and less than about 20 mg/mL, about 19 mg/mL, about 18 mg/mL, about 17 mg/mL, about 16 mg/mL, about 15 mg/mL, about 14 mg/mL, about 13 mg/mL, about 12 mg/mL, about 11 mg/mL, or about 10 mg/mL soluble at a temperature higher than the room temperature, e.g., at about 63° C. In some embodiments, a composition comprising the morphic Form II of the present disclosure is characterized by an X-ray diffraction pattern including prominent peaks at about 2.81 and about 5.63 degrees 2Θ. In one embodiment, a composition comprising the morphic Form II synthesized and/or crystallized by the disclosed method is characterized by an X-ray diffraction pattern substantially similar to that set forth in FIG. 1. In yet another embodiment, a composition comprising the morphic Form II synthesized and/or crystallized by the disclosed method is characterized by an X-ray diffraction pattern substantially similar to that set forth in FIG. 13 or 17. The present disclosure also provide that morphic Form II synthesized and/or crystallized by the disclosed method shows a minor endotherm at about 41-43° C. (peak max) followed by overlapping major endotherms at about 90 and about 95° C. (peak max) in a DSC thermogram. In one embodiment, the final endotherm of morphic Form II synthesized and/or crystallized by the disclosed method has an onset at about 196° C. in a DSC thermogram.

The present disclosure provides a method for synthesizing crystalline morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester, by seeding with about 0.1-10% (e.g., about 0.1-0.2%, about 0.2-0.3%, about 0.3-0.4%, about 0.4-0.5%, about 0.5-0.6%, about 0.6-0.7%, about 0.7-0.8%, about 0.8-0.9%, about 0.9-1.0%, about 1.0-2.0%, about 2.0-3.0%, about 3.0-4.0%, about 4.0-5.0%, about 5.0-6.0%, about 6.0-7.0%, about 7.0-8.0%, about 8.0-9.0%, or about 9.0-10.0%) of seed of the phosphonic acid. Some embodiments provide seeding the crystallization process with about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5% about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.0-about 8.0%, about 8.0-about 9.0%, or about 9.0%-about 10% of seed of the phosphonic acid. In additional embodiments the crystalline morphic form is formed with slow or medium stirring or agitation during the crystallization process. In one embodiment, the rate of stirring affects the type of morphic form produced. In another embodiment, the rate of stirring does not affect the type of morphic form produced. The embodiments provide morphic Form II crystallization by a process comprising methanol. The embodiments further provide crystallization process for forming morphic Form II by seeding with Form II or Form I of the phosphonic acid.

In some embodiments, Form II of Compound 1 is substantially free of impurities. The present disclosure provides, a morphic Form II of a compound having Formula II or III having a purity of equal to or greater than 91% is used to treat viral infection (e.g., a dsDNA viral infection) in a subject wherein said infection is resistant to valganciclovir hydrochloride (or ganciclovir) or wherein said subject exhibits side effects to valganciclovir hydrochloride (or ganciclovir). Alternatively or additionally, the compound of Formula II or III having a purity of equal to or greater than 91% wt/wt or being in Form II, e.g., having less than or equal to 9% wt/wt of other morphic forms or an amorphous form, is used to treat cytomegalovirus (CMV) subsequent to treatment with ganciclovir, for example, wherein the CMV infection is emergent. The patient may be a bone marrow stem cell transplant patient, especially where there is a risk (real or perceived) for bone marrow toxicity from ganciclovir in the patient.

In another embodiment, the subject is a mammal. In another embodiment, the subject is a human.

In another embodiment, a compound of Formula II or III having a purity of equal to or greater than 91% or being in Form II is administered orally, for example, at a dosage of about 0.01 mg/kg to about 10 mg/kg or more, e.g., up to about 100 mg/kg. In another embodiment, said compound of Formula II or III having a purity of equal to or greater than 91% wt/wt or being in Form II, e.g., having less than or equal to 9% wt/wt of other morphic forms or an amorphous form, is administered to said subject at a dosage of about 0.01 mg/kg, about 0.05 mg/kg, about 0.1 mg/kg, about 0.5 mg/kg, about 1.0 mg/kg, about 1.5 mg/kg, about 2.0 mg/kg, about 2.5 mg/kg, about 3.0 mg/kg, about 3.5 mg/kg, about 4.0 mg/kg, about 4.5 mg/kg, about 5.0 mg/kg, about 5.5 mg/kg, about 6.0 mg/kg, about 6.5 mg/kg, about 7.0 mg/kg, about 7.5 mg/kg, about 8.0 mg/kg, about 8.5 mg/kg, about 9.0 mg/kg, about 9.5 mg/kg, or about 10 mg/kg or more or any range therein.

The present disclosure provides, morphic Form II of a compound of Formula II or III (or a pharmaceutically acceptable salt thereof) characterized by an X-ray diffraction pattern with two or more (e.g., three or more, four or more, five or more, six or more, seven or more, eight or more, nine or more, or ten or more) peaks expressed in degrees 2Θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61, or having an X-ray diffraction pattern substantially similar to that set forth in FIG. 1, FIG. 7, FIG. 13, FIG. 14, FIG. 20, FIG. 21, or FIG. 25, administered at a dose of about 100 mg twice a week or at a dose of about 200 mg once a week. In one embodiment, a composition comprising the morphic Form II having indexing substantially similar to that set forth in FIG. 2 and/or a DSC Thermogram substantially similar to that set forth in FIG. 4, FIG. 15, FIG. 16 or FIGS. 22-24 is administered at a dose of about 100 mg twice a week or at a dose of about 200 mg once a week.

The present disclosure provides, morphic Form II of a compound of Formula II or III (or a pharmaceutically acceptable salt thereof) characterized by an X-ray diffraction pattern with two or more (e.g., three or more, four or more, five or more, six or more, seven or more, eight or more, nine or more, or ten or more) peaks expressed in degrees 2Θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61, or having an X-ray diffraction pattern substantially similar to that set forth in FIG. 1, FIG. 7, FIG. 13, FIG. 14, FIG. 20, FIG. 21, or FIG. 25, administered at a dose of about 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg).

In some embodiments, a composition comprising the morphic Form II having indexing substantially similar to that set forth in FIG. 2 and/or a DSC Thermogram substantially similar to that set forth in FIG. 4, FIG. 15, FIG. 16 or FIGS. 22-24 is administered at a dose of about 1-4 mg/kg (e.g., about 1.0-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg).

The present disclosure also provides for the use of Compound 1 or Compound 1 in Form II, having a purity of equal to or greater than 91% wt/wt, e.g., having less than or equal to 9% wt/wt of other morphic forms or an amorphous form, in the manufacture of a medicament for the therapeutic and/or prophylactic treatment of viral infection in a subject, e.g., an immunodeficient subject.

In another embodiment, the disclosure provides a method for the therapeutic and/or prophylactic treatment of viral infection in a subject, e.g., an immunodeficient subject, the method comprising administering a compound of Formula II or III having a purity of equal to or greater than 91% wt/wt or being in Form II, e.g., having less than or equal to 9% wt/wt of other morphic forms or an amorphous form, to the subject.

In another embodiment, the disclosure also provides an oral dosage form comprising a compound of Formula II or III having a purity of equal to or greater than about 91% wt/wt or being in Form II, e.g., having less than or equal to about 9% wt/wt of other morphic forms or an amorphous form, for the therapeutic and/or prophylactic treatment of viral infection in a subject, wherein said oral dosage form, upon administration to a human at a dosage of about 2 mg/kg of said compound, provides an $AUC_{0\text{-}inf}$ of said compound of about 2000 to about 4000 h*ng/mL, e.g., about 2500 to about 3000 h*ng/mL.

In another embodiment, the disclosure also provides an oral dosage form comprising a compound of Formula II or III having a purity of equal to or greater than about 91% wt/wt or being in Form II, e.g., having less than or equal to about 9% wt/wt of other morphic forms or an amorphous form, for the therapeutic and/or prophylactic treatment of viral infection in a subject, wherein said oral dosage form, upon administration to a human at a dosage of about 1-2 mg/kg, about 2-3 mg/kg, about 3-4 mg/kg of said compound, provides a $C_{max}$ of said compound of about 100 to about 500 ng/mL, e.g., about 200 to about 400 h*ng/mL.

In another embodiment, the disclosure also provides an oral dosage form comprising a compound of Formula II or III having a purity of equal to or greater than about 91% wt/wt or being in Form II, e.g., having less than or equal to about 9% wt/wt of other morphic forms or an amorphous form, for the therapeutic and/or prophylactic treatment of viral infection in a subject, wherein said oral dosage form, upon administration to a human at a dosage of about 1-2 mg/kg, about 2-3 mg/kg, about 3-4 mg/kg of said compound of Formula II or III and metabolism of said compound of Formula II or III to cidofovir, provides a $C_{max}$ of said cidofovir that is less than about 30% of the $C_{max}$ of said compound of Formula II or III, e.g., less that about 20% of the $C_{max}$ of said compound of Formula II or III.

Recrystallization Protocols

In one or more embodiments, the present technology includes five district recrystallization steps to purify Compound 1. For instance, in some preferred embodiments, the following schedule is used for the sequential recrystallization:

| | |
|---|---|
| 1st Recrystallization | Dissolve in MeOH 60-70 C., stir 5 min. |
| | Cool to 60 C. and stir 1 h |
| | Cool to 50 C. over 6 h |
| | Cool to 20 C. over 2 h and stir 2 h |
| | Filter |
| 2nd Recrystallization | Dissolve in MeOH 60-70° C., stir 5 min. |
| | Cool to 60° C. and stir 1 h |
| | Cool to 50° C. over 6 h |
| | Cool to 20° C. over 2 h and stir 2 h |
| | Filter |
| 3rd Recrystallization | Dissolve in MeOH at 60-70° C., stir 20 min. |
| | Cool to 60° C., stir 20 min., add seed stock, stir 2 h |
| | Cool to 50° C. over 8 h and stir 2 h |
| | Cool to 20 over 6 h and stir 2 h |
| | Filter, dry ≤40 C., mill |
| 4th Recrystallization | Dissolve in MeOH 60-70° C., stir 20 min. |
| | Add n-heptane keeping above 50° C., stir 20 min. |
| | Cool to 40° C. over 6 h, stir 1 h |
| | Cool to 20° C. over 6 h, stir 2 h |
| | Filter |
| 5th Recrystallization | Dissolve in MeOH at 60-70° C., stir 20 min. |
| | Cool to 61° C., add seed stock, stir 2 h |
| | Cool to 50° C. over 8 h, stir 2 h |
| | Cool to 20° C. over 6 h, stir 2 h |
| | Filter, dry ≤40° C., mill |

In some embodiments, other recrystallization schedules can be used. For instance, in some embodiments, Compound 1 can be subject to a single methanol recrystallization before recrystallizing with n-heptane and methanol. This can then be followed by a final recrystallization with methanol including seeding with Form II. Alternative schedules for recrystallization and purification can be envisioned by one of skill in the art, and the following illustrative embodiments are not to be construed as limiting:

Recrystallization Embodiment A

| | |
|---|---|
| 1st Recrystallization | Dissolve in MeOH 60-70° C., stir 5 min. |
| | Cool to 60° C. and stir 1 h |
| | Cool to 50° C. over 6 h |
| | Cool to 20° C. over 2 h and stir 2 h |
| | Filter |
| 2nd Recrystallization | Dissolve in MeOH 60-70° C., stir 20 min. |
| | Add n-heptane keeping around 50 C., stir 20 min. |
| | Cool to 35° C. over 4 h, stir 1 h |
| | Cool to 20° C. over 6 h, stir 2 h |
| | Filter |
| 3rd Recrystallization | Dissolve in MeOH at 60-70° C., stir 20 min. |
| | Cool to 61° C., add seed stock, stir 2 h |
| | Cool to 50° C. over 8 h, stir 2 h |
| | Cool to 20° C. over 6 h, stir 2 h |
| | Filter, dry ≤40° C., mill |

Recrystallization Embodiment B

| | |
|---|---|
| 1st Recrystallization | Dissolve in MeOH 60-70° C., stir 20 min. |
| | Add n-heptane keeping above 50° C., stir 20 min. |
| | Cool to 4° C. over 6 h, stir 1 h |
| | Cool to 20° C. over 6 h, stir 2 h |
| | Filter |
| 2nd Recrystallization | Dissolve in MeOH at 60-70° C., stir 20 min. |
| | Cool to 60° C., stir 20 min., add seed stock, stir 2 h |
| | Cool to 50° C. over 8 h and stir 2 h |
| | Cool to 20° C. over 6 h and stir 2 h |
| | Filter, dry ≤40° C., mill |
| 3rd Recrystallization | Dissolve in MeOH at 60-70° C., stir 20 min. |
| | Cool to 61° C., add seed stock, stir 2 h |
| | Cool to 50° C. over 8 h, stir 2 h |
| | Cool to 20° C. over 6 h, stir 2 h |
| | Filter, dry ≤40° C., mill |

In some embodiments, alternative recrystallization protocols can be employed which will be apparent to one of skill in the art. One of skill in the art will recognize that different crystallizations can be more or less effective at removing different types of impurities.

TABLE 8

Crystallization Experiments of a Compound having Formula II or III in Methanol

| Conditions[a] | Observation | Method | Result |
|---|---|---|---|
| ~9 vols. Unseeded. ~91% yield. | Crystallizatin occurred at ~54-56° C.; Aggregates, irregular plates, B/E | XRPD | Form II |
| ~8.5 vols; Seed ~2% hand ground Compound 1 Form II at ~61° C. Dissolved. Seed with ~2% ground Compound 1 Form II at ~59° C. ~90% yield. | Opaque aggregates and small plates, B/E | XRPD SEM | Form II Very large agglomerates (>500 μm diameter); plates (up to ~50 μm)[b] |

TABLE 8-continued

Crystallization Experiments of a Compound having Formula II or III in Methanol

| Conditions[a] | Observation | Method | Result |
|---|---|---|---|
| ~10 vols. Seed ~0.5% hand ground Compound 1 Form II at ~58° C. Hold ~1 hour. ~94% yield. | Aggregates and plates, B/E | XRPD SEM | Form II Agglomerates (~500 μm diameter); plates (up to ~100 μm)[b] |
| | | PSA | d10 = 17.8 μm; d50 = 69.6 μm; d90 = 160.9 μm |
| ~10 vols. Seed ~3% hand ground Compound 1 Form II. Hold ~1 hour. ~91% yield. | Aggregates and plates, B/E | XRPD SEM | Form II Agglomerates (~200 μm diameter); plates (up to ~50 μm)[b] |
| | | PSA | d10 = 9.8 μm; d50 = 34.4 μm; d90 = 101.7 μm |
| ~8.5 vols. Unseeded. Hold ~4 h at ~58° C. (ppt). ~90% yield. | Aggregates and plates, B/E | XRPD | Form II |
| ~10 vols. Unseeded. Hold ~4 h at ~56° C. ~90% yield. | Aggregates and plates, B/E | XRPD | Form II |
| ~10 vols. Used Compound 1 Form H as starting material. Seed ~0.5% hand ground Compound 1. Hold ~1 h. ~85% yields. | Aggregates and plates, B/E | XRPD | Form II |
| ~10 vols. Used Compound 1 Form H as starting material. Unseeded. Hold ~4 h at ~56° C. ~86% yield. | Aggregates and plates, B/E | XRPD SEM | Form II Large plates (up to ~100 μm)[b] |
| ~10 vols in 97:3 Methanol:water. Unseeded. Hold ~4 h at ~56° C. ~92% yield. | Aggregates and plates, B/E | XRPD | Form II |
| ~10 vols in 93:7 Methanol:water. Unseeded. Hold ~4 h at ~56° C. ~94% yield. | Aggregates and small plates, B/E | XRPD SEM | Form II Plates (up to ~100 μm)[b] |
| ~10 vols. Slow agitation (~25 rpm). Unseeded. Hold ~4 h at ~57° C. ~94% yield. | Aggregates and small plates, B/E | XRPD SEM | Form II Agglomerates (~200 μm diameter) and plates (up to ~50 μm)[b] |
| ~10 vols. Slow agitation (~25 rpm). Unseeded. Hold at ~57° C. 3 h at slow agitation, 1 h at high agitation (~350 rpm). Slow agitation for remaining cool. Stir at ~15° C. at high agitation prior to isolation. ~95% yield. | Aggregates and plates, B/E | XRPD SEM | Form II Large agglomerates (~500 μm diameter) and plates (up to ~50 μm)[b] |

[a]Crystallizations were conducted under non-GMP conditions using EasyMax™. Temperatures, times, and rates were approximate. Crystallizations occurred in methanol unless otherwise specified. Ratios given are volumetric. All experiments used Compound 1 Form II sample as the starting material unless otherwise specified. Slow cooling (9-10 hours) was used in each of the crystallizations. Samples were dried in a vacuum oven between ~40° C. and ~48° C. for 7 hours-1 day unless otherwise specified. Scale was ~5 g.
[b]Observation based on SEM images.
[c]Significant loss of solvent was observed in reactor likely due to evaporation.

Pharmaceutical Compositions

In another aspect, provided herein is a pharmaceutical composition comprising polymorphs of the present invention (e.g., Polymorph Form II), and optionally a pharmaceutically acceptable carrier or diluent. Also provided herein is a pharmaceutical composition comprising polymorphs of the present invention (e.g., Polymorph or Form II) and a pharmaceutically acceptable carrier or diluent.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, about 0.1% to about 99.9%, about 0.2 to about 98%, about 0.3% to about 97%, about 0.4% to about 96%, or about 0.5 to about 95% of active ingredient in combination with a pharmaceutically acceptable carrier.

In one embodiment pharmaceutical composition containing about 0.5% to about 90% of active ingredient in combination with a pharmaceutically acceptable carrier is suitable for administration to mammals, e.g., humans. Some embodiments provide preparation of a pharmaceutical composition comprising about 0.1% to about 99.9%, about 0.2 to about 98%, about 0.3% to about 97%, about 0.4% to about 96%, or about 0.5 to about 95% of the compound of Formula II or III of the present invention for use in treating, preventing, or prophylaxis of viral infections or viral infection associated disorders. The present disclosure provides use of about 0.1% to about 99.9%, about 0.2 to about 98%, about 0.3% to about 97%, about 0.4% to about 96%, or about 0.5 to about 95% of the compound of Formula II or III for the manufacture of a medicament containing effective amounts of the compound for use in treating, preventing, or prophylaxis of viral infections and viral infection associated diseases.

In some embodiments, the pharmaceutical composition comprises an anhydrous morphic form (e.g., Form II) of the compound of Formula II or III (or a pharmaceutically acceptable salt thereof), which is substantially free of Form I and/or Form H. The pharmaceutical composition comprising morphic Form II of the present disclosure has equal to or less than about 10% Form I and/or Form H as impurities. In some embodiments, the pharmaceutical composition comprising Form II has equal to or less than about 9%, about 8%, about 7%, about 6%, about 5%, about 4%, about 3%, about 2%, about 1%, about 0.9%, about 0.8%, about 0.7%, about 0.6%, about 0.5%, about 0.4%, about 0.3%, about 0.2%, about 0.1%, about 0.05%, about 0.01%, or about 0.001% Form I and/or Form H as impurities.

The polymorphs described herein (e.g., Polymorph II) may be combined with a pharmaceutically acceptable carrier according to conventional pharmaceutical compounding techniques. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

Pharmaceutical compositions comprising the polymorphs of the present invention (e.g., Form II) may be formulated to have any concentration desired. In some embodiments, the composition is formulated such that it comprises at least a therapeutically effective amount. As used herein, "therapeutically effective amount" means that amount necessary to make a clinically observed improvement in the patient. In some embodiments, the composition is formulated such that it comprises an amount that would not cause one or more unwanted side effects.

Pharmaceutical compositions include those suitable for oral, sublingual, nasal rectal, vaginal, topical, buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, lozenge or tablet. In other embodiments, the pharmaceutical composition is in the form of a suspension.

The regimen of administration can affect what constitutes a pharmaceutically effective amount. A polymorph of the present invention (e.g., Form II), and compositions thereof, can be administered to the subject either prior to or after the onset of a disease. Further, several divided dosages, as well as staggered dosages can be administered daily or sequentially, or the dose can be continuously infused, or can be a bolus injection. Further, the dosages can be proportionally increased or decreased as indicated by the exigencies of the therapeutic or prophylactic situation. Further, the dosages may be co-administered in combination with other chemotherapeutic agents known by the skilled artisan.

A "pharmaceutical composition" is a formulation containing a compound of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient or carrier" means an excipient or carrier that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is viral infection.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

Pharmaceutical compositions comprising Form II of a compound having Formula II or III (or a pharmaceutically acceptable salt thereof) can be identified by comparison of the compositions' X-ray powder diffraction patterns to an X-ray powder diffraction pattern of Form II. It will be appreciated that pharmaceutical compositions comprising Form II of a compound having Formula II or III (or a pharmaceutically acceptable salt thereof) exhibit non-identical X-ray powder diffraction patterns that are substantially the same pattern as compared to FIG. 1. Observed slight differences in XRPD patterns may be attributed to the aforementioned factors, including the presence of other impurities in the sample.

The tablets were lightly ground using a mortar and pestle prior to analysis. The tablets show very similar XRPD patterns similar to FIG. 13 and/or FIG. 14, indicative of crystalline material with diffuse scatter potentially from one or more excipients.

Figure 17:
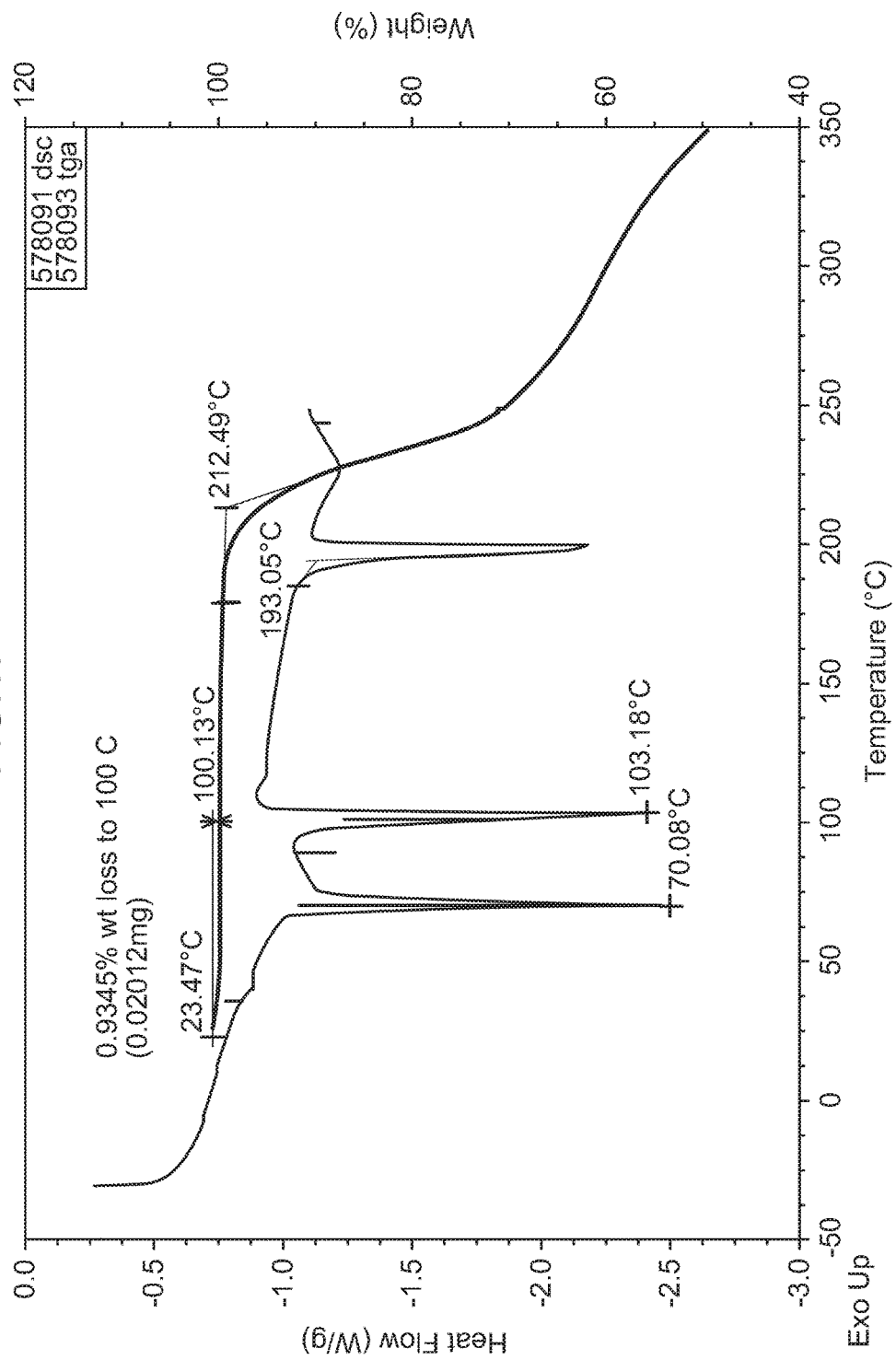
FIG. 17 shows thermal analysis of Form H (DSC Thermogram).

In one embodiment, Form II of a compound having Formula II or III (or a pharmaceutically acceptable salt thereof) exhibits an X-ray powder diffraction pattern having a characteristic peaks expressed in degrees 2-theta (±0.2) at 2.81, 5.63, 19.00, 19.57, 22.76, and 24.70, or having an X-ray diffraction pattern substantially similar to that set forth in FIG. 13 or 17, indexing substantially similar to that set forth in FIG. 2, and DSC Thermogram substantially similar to that set forth in FIG. 15 or 16.

In some embodiments, the DSC thermograms for two Form II tablet samples show overlapping minor endotherms at about 90° C. and about 95° C. (peak max) and a major endotherm with an onset at about 165° C. The tablet samples have a large endotherm at about 196° C. of the Form II crystalline form.

In one embodiment, hot stage microscopy does not show any significant observations prior to flow at about 189° C. other than some potential sublimation observed at about 98° C. In some embodiments, the Form II of the present embodiments has a potential thermotropic mesophase.

TABLE 9

Characterization of Form II Tablet 1

| Sample | Method | Analysis/Result | FIG. |
|---|---|---|---|
| Form II Tablet-1 | DSC | Minor overlapping endos at ~90° C. and ~95° C.; Major endo onset at ~165° C. | 18 |
| | XRPD | Crystalline with diffuse scatter; Peaks consistent with Form II observed | 16 |

[a]Sample was submitted as white tablet but was lightly hand ground in mortar and pestle for analysis

TABLE 10

Characterization of Form II Tablet 2

| Sample | Method | Analysis/Result | FIG. |
|---|---|---|---|
| Form II Tablet-2 | DSC | Minor overlapping endos at ~91° C. and ~95° C.; Major endo onset at ~165° C. | 19 |
| | XRPD | Crystalline with diffuse scatter; Peaks consistent with Form II observed | 17 |

[a]Sample was submitted as white tablet but was lightly hand ground in mortar and pestle for analysis In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Dosages can range from about 0.01 mg/kg to about 100 mg/kg. In preferred aspects, dosages can range from about 0.1 mg/kg to about 10 mg/kg. In an aspect, the dose will be in the range of about 1 mg to about 1 g; about 10 mg to about 500 mg; about 20 mg to about 400 mg; about 40 mg to about 400 mg; or about 50 mg to about 400 mg, in single, divided, or continuous doses (which dose may be adjusted for the patient's weight in kg, body surface area in $m^2$, and age in years). In certain embodiments, the amount per dosage form can be about 0.1 mg to about 1000 mg, e.g., about 0.1 mg, about 0.5 mg, about 1.0 mg, about 2.0 mg, about 3.0 mg, about 4.0 mg, about 5.0 mg, about 6.0 mg, about 7.0 mg, about 8.0 mg, about 9.0 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg or more. In one embodiment, the amount can be about 20 mg. In one embodiment, the amount can be about 50 mg.

Form II or Form H of Compound 1 or pharmaceutically acceptable salts thereof is formulated as a pharmaceutical composition or is used in the manufacture of a medicament for the treatment of a viral infection and/or viral infection associated disease and/or disorder. The composition and/or the medicament of Form II or Form H of Compound 1 or pharmaceutically acceptable salts thereof is formulated as a tablet or suspension. Tablets of Compound 1 Form II is formulated comprising pharmacologically acceptable buffers, excipients, carriers, including emulsifiers, enhancers (e.g., absorption enhancers), disintegrants (e.g., Polyvinylpolypyrrolidone (polyvinyl polypyrrolidone, PVPP, crospovidone, crospolividone or E1202), which is a highly cross-linked modification of polyvinylpyrrolidone (PVP)), and/or polymers disclosed in the present disclosure and well-known in the art.

In one embodiment, the present disclosure provides Tablet Formulation 1 of Compound 1 for use in prophylactic treatment or prevention viral infection and/or viral associated disease or disorder. The present disclosure provides Tablet Formulation 1 of Compound 1 for use in treating immunodeficient subjects, or pre- or post-organ and/or tissue transplantation subjects.

In another embodiment, the present disclosure provides Tablet Formulation 2 of Compound 1 for use in prophylactic treatment or prevention viral infection and/or viral associated disease and/or disorder. The present disclosure provides Tablet Formulation 2 of Compound 1 for use in treating immunodeficient subjects, or pre- or post-organ and/or tissue transplantation subjects.

In some embodiments, the present disclosure provides Tablet Formulation 1 of Compound 1 Form II for use in prophylactic treatment or prevention viral infection and/or viral associated disease and/or disorder. The present disclosure provides Tablet Formulation 1 of Compound 1 Form II for use in treating immunodeficient subjects, or pre- or post-organ and/or tissue transplantation subjects.

In some embodiments, the present disclosure provides Tablet Formulation 2 of Compound 1 Form II for use in prophylactic treatment or prevention viral infection and/or viral associated disease and/or disorder. The present disclosure provides Tablet Formulation 2 of Compound 1 Form II for use in treating immunodeficient subjects, or pre- or post-organ and/or tissue transplantation subjects.

Compositions of two Compound 1 formulations in tablet form of the current disclosure are listed in Table 11.

In one embodiment, the present disclosure provides suspension Formulation 3 of Compound 1 for use in prophylactic treatment or prevention viral infection and/or viral associated disease and/or disorder. The present disclosure provides suspension Formulation 3 of Compound 1 for use in treating immunodeficient subjects, or pre- or post-organ and/or tissue transplantation subjects.

In another embodiment, the present disclosure provides suspension Formulation 4 of Compound 1 for use in prophylactic treatment or prevention viral infection and/or viral associated disease and/or disorder. The present disclosure provides suspension Formulation 4 of Compound 1 for use in treating immunodeficient subjects, or pre- or post-organ and/or tissue transplantation subjects.

TABLE 11

100 mg Tablet formulations of Compound 1

| | Tablet Formulations | | | |
|---|---|---|---|---|
| | Formulation 1 | | Formulation 2 | |
| Ingredient | mg/tablet | % wt per tablet | mg/tablet | % wt per tablet |
| Compound 1 | 100.00 | 27.78 | 100.00 | 27.8 |
| Silicified Microcrystalline Cellulose (Prosolv 90), | 79.86 | 22.18 | 80.0 | 22.2 |
| Crospovidone (Polyplasdone XL-10) | 13.37 | 3.714 | 13.4 | 3.7 |
| Microcrystalline Cellulose and Mannitol (Avicel HFE 102) | 40.93 | 11.37 | —/— | —/— |
| Microcrystalline Cellulose (Avicel PHE102) | —/— | —/— | 41.0 | 11.4 |
| Mannitol (Pearlitol 100 SD) | 124.10 | 34.46 | 122.0 | 33.9 |
| Colloidal Silicon Dioxide (Cab-O-Sil) | —/— | —/— | 1.8 | 0.5 |
| Magnesium Stearate | 1.8 | 0.5000 | 1.8 | 0.5 |
| Total | 360 | 100% | 360 | 100% |

In some embodiments, the present disclosure provides suspension Formulation 3 or 4 of Compound 1 Form II for use in prophylactic treatment and/or prevention viral infection and/or viral associated disease and/or disorder. The present disclosure provides suspension Formulation 3 or 4 of Compound 1 Form II for use in treating immunodeficient subjects, or pre- or post-organ and/or tissue transplantation subjects.

Compositions of two Compound 1 formulations in suspension form of the current disclosure are listed in Table 12.

TABLE 12

Suspension Formulations of Compound 1

| | Suspension Formulations | | | |
|---|---|---|---|---|
| | Formulation 3 (in situ precipitation) | | Formulation 4 (direct wetting) | |
| Ingredient | g/L | % wt | g/L | % wt |
| Compound 1 | 10.00 | 0.907 | 100.00 | 1.00 |
| Sodium Phosphate, dibasic | 0.650 | 0.059 | —/— | —/— |
| Citric Acid, monohydrate | 1.500 | 0.136 | 0.585 | 0.06 |
| Sodium Citrate | —/— | —/— | 0.985 | 0.10 |
| Xantham Gum | 1.250 | 0.113 | 0.375 | 0.04 |

TABLE 12-continued

Suspension Formulations of Compound 1

| | Suspension Formulations | | | |
|---|---|---|---|---|
| | Formulation 3 (in situ precipitation) | | Formulation 4 (direct wetting) | |
| Ingredient | g/L | % wt | g/L | % wt |
| Methylparaben, sodium salt | 0.850 | 0.077 | 1.690 | 0.17 |
| Propylparaben, sodium salt | 0.085 | 0.0077 | 0.190 | 0.02 |
| Sucralose | 0.200 | 0.018 | 0.500 | 0.05 |
| Microcrystalline Cellulose and Carboxymethylcellulose Sodium (VivaPur MCG 591) | 15.00 | 1.360 | 15.625 | 1.56 |
| High Fructose Corn Syrup (55%) | 426.6 | 38.68 | 276.720 | 27.67 |
| Lemon Lime Flavor (WONF220J15) | 1.500 | 0.136 | 4.000 | 0.40 |
| Sodium Hydroxide, pellets | 0.700 | 0.0635 | | |
| Purified Water | 644.5 | 58.43 | 689.335 | 68.93 |
| Sodium Hydroxide/Hydrochloric Acid | qs | qs | qs | qs |
| Total | 360 | 100% | 360 | 100% |

The formulations of the present disclosure are used in treating end-organ damage related to viral infection, e.g. treating, preventing, and/or ameliorating BK virus infection associated end organ damage in a subject.

The formulations of the present disclosure are used in manufacturing a medicament in prophylactic treatment and/or prevention viral infection and/or viral associated disease and/or disorder.

In one embodiment, Form II of a compound of Formula II or III (or a pharmaceutically acceptable salt thereof) is administered at a dose of about 100 mg (tablet Formulation 1 or 2 described in Table 11, or suspension Formulation 3 or 4 described in Table 12) twice a week. In another embodiment, Form II of a compound of Formula II or III (or a pharmaceutically acceptable salt thereof) is administered at a dose of about 200 mg (tablet Formulation 1 or 2 described in Table 11, or suspension Formulation 3 or 4 described in Table 12) once a week.

In another embodiment, the invention provides compositions (e.g., pharmaceutical compositions) with desirable pharmacokinetic characteristics. For example, the compositions of the invention may provide a blood level of Form II of a compound of Formula II or III (or a pharmaceutically acceptable salt thereof), which, after metabolism to the therapeutically-active form (i.e., cidofovir), results in blood levels of the metabolite that do not induce toxicity (e.g., nephrotoxicity).

An effective amount of a pharmaceutical agent is that which provides an objectively identifiable improvement as noted by the clinician or other qualified observer. As used herein, the term "dosage effective manner" refers to amount of an active compound to produce the desired biological effect in a subject or cell.

In another embodiment, compound of Formula II, III, or another composition of the present invention can be administered to a subject as a single dose. In another embodiment, Formula II, III, or another composition of the present invention can be administered to a subject in multiple doses. Multiple doses can be administered regularly, for example, once every 12 hours, once a day, every 2 days, every 3 days, every 4 days, every 5 days, every 6 days, every 7 days, every 8 days, every 9 days, every 10 days, every 11 days, every 12 days, every 13 days, every 14 days or every 15 days. For example, doses can be administered twice per week. Moreover, each individual dose can be administered with the same or a different dosage.

For example, a subject can be administered with a first dose of about 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of Form II of a compound having Formula II or III (or a pharmaceutically acceptable salt thereof) followed by one or more additional doses at 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of Form II of Formula II or III (or a pharmaceutically acceptable salt thereof) in the same week or in the following week. For example, a subject can be administered with a first dose of about 3 mg/kg followed by one or more additional doses at about 1 mg/kg. For example, a subject can be administered with a first dose of about 2 mg/kg followed by one or more additional doses at about 3 mg/kg. For example, a subject can be administered with a first dose of 4 mg/kg followed by one or more additional doses at about 4 mg/kg.

Multiple doses can also be administered at variable time intervals. For example, the first 2, 3, 4, 5, 6, 7, or 8 or more doses can be administered at an interval of 6 days followed by additional doses administered at an interval of 7 days. For example, the first 2, 3, 4, 5, 6, 7, or 8 or more doses can be administered at an interval of 7 days followed by additional doses administered at an interval of 3 days.

In another embodiment, the invention provides an oral dosage form comprising Form II of a compound having Formula II or III (or a pharmaceutically acceptable salt thereof) having a purity of greater than 91% or being in Form II for the therapeutic and/or prophylactic treatment of viral infection in a subject, wherein said oral dosage form, upon administration to a human at a dosage of about 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of said compound, provides an $AUC_{0-inf}$ of said compound of about 2000 to about 4000 h*ng/mL, e.g., about 2500 to about 3000 h*ng/mL. In some embodiments, the $AUC_{0-inf}$ of said compound is about 2000, 2100, 2200, 2300, 2400, 2500, 2600, 2700, 2800, 2900, 3000, 3100, 3200, 3300, 3400, 3500, 3600, 3700, 3800, 3900, or 4000 h*ng/mL or any range therein. $AUC_{0-inf}$ can be determined by any of the well-known methods in the art and as described in the examples herein.

In another embodiment, the invention provides an oral dosage form comprising Form II of a compound of Formula II or III (or a pharmaceutically acceptable salt thereof) having a purity of equal to or greater than 91% or being in Form II for the therapeutic and/or prophylactic treatment of viral infection in a subject, wherein said oral dosage form, upon administration to a human at a dosage of about 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of said compound, provides a $C_{max}$ of said compound of about 100 to about 500 ng/mL, e.g., about 200 to about 400 ng/mL. In some embodiments, the $C_{max}$ of the compound is about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, or about 500 ng/mL or any range therein. $C_{max}$ can be determined by any of the well-known methods in the art and as described in the examples herein.

In another embodiment, the invention provides an oral dosage form comprising Form II of a compound having Formula II or III (or a pharmaceutically acceptable salt thereof) having a purity of greater than about 91% or being in Form II for the therapeutic and/or prophylactic treatment of viral infection in a subject, wherein said oral dosage form, upon administration to a human at a dosage of about 1-4 mg/kg (e.g., about 1-1.1 mg/kg, about 1.1-1.2 mg/kg, about 1.2-1.3 mg/kg, about 1.3-1.4 mg/kg, about 1.4-1.5 mg/kg, about 1.5-1.6 mg/kg, about 1.6-1.7 mg/kg, about 1.7-1.8 mg/kg, about 1.8-1.9 mg/kg, about 1.9-2.0 mg/kg, about 2.0-2.1 mg/kg, about 2.1-2.2 mg/kg, about 2.2-2.3 mg/kg, about 2.3-2.4 mg/kg, about 2.4-2.5 mg/kg, about 2.5-2.6 mg/kg, about 2.6-2.7 mg/kg, about 2.7-2.8 mg/kg, about 2.8-2.9 mg/kg, about 2.9-3.0 mg/kg, about 3.0-3.1 mg/kg, about 3.1-3.2 mg/kg, about 3.2-3.3 mg/kg, about 3.3-3.4 mg/kg, about 3.4-3.5 mg/kg, about 3.5-3.6 mg/kg, about 3.6-3.7 mg/kg, about 3.7-3.8 mg/kg, about 3.8-3.9 mg/kg, or about 3.9-4.0 mg/kg) of said compound having Formula II or III (or a pharmaceutically acceptable salt thereof) and metabolism of said compound of Formula II or III (or a pharmaceutically acceptable salt thereof) to cidofovir, provides a $C_{max}$ of said cidofovir that is less than about 30% of the $C_{max}$ of said compound having Formula II or III (or a pharmaceutically acceptable salt thereof), e.g., less that about 20% of the $C_{max}$ of said compound having Formula II or III (or a pharmaceutically acceptable salt thereof). In some embodiments, the $C_{max}$ of the metabolite (i.e., cidofovir) is less than about 50%, 45%, 40%, 35%, 30%, 25%, 20%, 15%, or 10% of the $C_{max}$ of Form II of a compound having Formula II or III (or a pharmaceutically acceptable salt thereof).

In another embodiment, the invention provides an oral dosage form comprising a Form II of a compound having Formula II or III (or a pharmaceutically acceptable salt thereof) having a purity of greater than 91% or being in Form II, wherein upon administration to a human at a dosage of about 2 mg/kg of said compound of Form II of a compound having Formula II or III (or a pharmaceutically acceptable salt thereof), provides an $AUC_{0-inf}$ of cidofovir of about 1000 to about 5000 h*ng/mL, e.g., about 1500 to about 4000 h*ng/mL. In some embodiments, the $AUC_{0-inf}$ of cidofovir is about 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 h*ng/mL or any range therein.

In another embodiment, the invention provides an oral dosage form comprising a Form II of a compound having Formula II or III (or a pharmaceutically acceptable salt thereof) having a purity of equal to or greater than 91% or being in Form II, wherein upon administration to a human at a dosage of about 2 mg/kg of said Form II of a compound having Formula II or III (or a pharmaceutically acceptable salt thereof), provides a $C_{max}$ of cidofovir of about 10 to about 100 ng/mL, e.g., about 20 to about 70 ng/mL. In some embodiments, the $C_{max}$ of Form II of a compound having Formula II or III (or a pharmaceutically acceptable salt thereof) is about 10, 20, 30, 40, 50, 60, 70, 80, 90, or 100 ng/mL or any range therein.

In certain embodiments, the oral dosage form provides more than one of the pharmacokinetic characteristics described above, e.g., the $AUC_{0-inf}$ or $C_{max}$ of Form II of a compound having Formula II or III (or a pharmaceutically acceptable salt thereof) or the metabolite (i.e., cidofovir) or the $C_{max}$ ratio of the metabolite (i.e., cidofovir) to the compound of formula (I), e.g., 2, 3, 4, or more of the pharmacokinetic characteristics in any combination.

The pharmacokinetic behavior of a composition will vary somewhat from subject to subject within a population. The numbers described above for the compositions of the invention are based on the average behavior in a population. The present invention is intended to encompass compositions that on average fall within the disclosed ranges, even though it is understood that certain subjects may fall outside of the ranges.

The pharmaceutical compositions can be included in a container, pack, or dispenser together with instructions for administration.

The compounds of the present invention are capable of further forming salts. All of these forms are also contemplated within the scope of the claimed invention.

Definitions

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate, or other esters.

The compounds, or pharmaceutically acceptable salts, esters or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in Remington: the Science and Practice of Pharmacy, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

It will be appreciated that the methods disclosed herein are suitable for both large-scale and small-scale preparations of the desired compounds. In preferred embodiments of the methods described herein, the phosphonate esters may be prepared on a large scale, for example on an industrial production scale rather than on an experimental/laboratory scale. For example, a batch-type process according to the methods of the disclosure allows the preparation of batches of at least 1 g, or at least 5 g, or at least 10 g, or at least 100 g, or at least 1 kg, or at least 100 kg of phosphonate ester product. Furthermore, the methods allow the preparation of a phosphonate ester product having a purity of at least 98%, or at least 98.5% as measured by HPLC. In preferred embodiments according to the disclosure, these products are obtained in a reaction sequence that does not involve purification by any form of chromatography (e.g., gas chromatography, HPLC, preparative LC, size exclusion chromatography, and the like).

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

As used herein, a "subject" is interchangeable with a "subject in need thereof", both of which refer to a subject having a disorder in which viral infection plays a part, or a subject having an increased risk of developing viral infection associated disease or disorder relative to the population at large. A "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human.

As used herein, "treating," "treatment" or "treat" describes the management and care of a patient for the purpose of combating a disease, condition, or disorder and includes the administration of a polymorph of the present invention (e.g., Polymorph II), to alleviate the symptoms or complications of a disease, condition or disorder, or to eliminate the disease, condition or disorder. The term "treat" can also include treatment of a cell in vitro or an animal model.

A polymorph of the present invention may also be used to prevent a relevant disease, condition or disorder, or used to identify suitable candidates for such purposes. As used herein, "preventing," "prevent," or "protecting against" describes reducing, ameliorating or eliminating the onset of the symptoms or complications of such disease, condition or disorder.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

As used herein "crystalline" means that the compound is crystallized into a specific crystal packing arrangement in three spatial dimensions or the compound having external face planes. Compounds in the crystalline state exhibit distinct sharp peaks in their X-ray diffraction patterns and typically exhibit well defined melting points. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate.

As used herein "amorphous" or "non-crystalline" means that the compound does not exhibit any substantial peaks in its X-ray diffraction pattern. Typically, non-crystalline materials do not exhibit well defined melting points.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

For the purposes of promoting an understanding of the embodiments described herein, reference made to preferred embodiments and specific language are used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. All percentages and ratios used herein, unless otherwise indicated, are by weight.

The term "about" is used herein to mean approximately, in the region of, roughly or around. When the term "about" is used in conjunction with a numerical range, it modifies that range by extending the boundaries above and below the numerical values set forth. In general, the term "about" is used herein to modify a numerical value above and below the stated value by a variance of 20%.

As used in the present disclosure, whether in a transitional phrase or in the body of a claim, the terms "comprise(s)" and "comprising" are to be interpreted as having an open-ended meaning. That is, the terms are to be interpreted synonymously with the phrases "having at least" or "including at least." When used in the context of a process the term "comprising" means that the process includes at least the recited steps, but may include additional steps. When used in the context of a molecule, compound, or composition, the term "comprising" means that the compound or composition includes at least the recited features or components, but may also include additional features or components.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1—General Preparation of Phosphonic Acid, [[(S)-2-(4-amino-2-oxo-1(2H)-pyrimidinyl)-1-(hydroxymethyl) ethoxy]methyl]mono[3-(hexadecyloxy)propyl] ester (Compound 1)

Step 1: Preparation of (S)—N1-[(2-hydroxy-3-triphenylmethoxy)propyl] cytosine (Compound 2)

A slurry of (S)-trityl glycidyl ether (56.4 kg, 178.22 mol), cytosine (18.0 kg, 162.02 mol), and potassium carbonate (2.20 kg, 16.20 mol) in dimethylformamide (73.2 kg) was heated to 85-95° C. After 9 hours the reaction mixture was cooled down to 66-70° C. and quenched with toluene (216.0 kg). The resulting slurry was further cooled down to −10 to 5° C. and filtered to collect a solid. This material was washed with toluene (38.9 kg), re-suspended in toluene (168.8 Kg) at 15-25° C., and once again filtered.

In order to further remove residual cytosine and process-related impurities a purification cycle was carried out, where the compound was washed with acetone (36.0 Kg), followed by trituration of the solid in water/acetone (90.0 kg/54.0 Kg) at 17-22° C., and ending with another acetone wash (36.0 Kg). This cycle was repeated several times to improve purity of the product but should be carried out at least once.

A suspension of the filter cake in acetone (178.9 Kg) at 35-45° C. was prepared. After 3 hours, the reaction mixture was filtered and the resulting solid was washed with acetone (36.0 Kg) to afford Compound 2 (45.0 kg, 65% yield), and dried in vacuo at ≤40° C. for 12 hours. Purity of the compound was determined via HPLC analysis (>99.0%). The compound was analyzed by NMR. NMR characterization was consistent with structure of Compound 2.

Step 2: Preparation of Phosphonic Acid [[(S)-2-(4-amino-2-oxo-1(2H)-pyrimidinyl)-1-(hydroxymethyl)-2-(triphenylmethoxy)ethyl]methyl]mono[3-(hexadecyloxy)propyl] ester (Compound 3)

A solution of Compound 2 (45.0 kg, 105.26 mol), P-[[[(4-methylphenyl)sulfonyl]oxy]methyl]-, mono[3-(hexadecyloxy)propyl]ester, sodium salt (Compound 4) (66.1 kg, 115.79 mol), magnesium tert-butoxide (18.9 kg, 110.53 mol) and dimethylformamide (135.0 kg) was heated at 75-85° C. for 3 hours. The reaction mixture was cooled down to 25-35° C. and isopropyl acetate (387 kg) was added. After completion of the addition the reaction mixture was further cooled down to 15-25° C. and extracted with HCl (aq.; 22.8 kg conc. HCl diluted with 290.8 kg water) and NaCl (aq.; 161.10 kg sodium chloride dissolved in 606.3 kg water). The resulting organic layer was vacuum distilled and the concentrate was chased two times with methanol to remove any residual isopropyl acetate to afford Compound 3, which was used in the next step without further purification.

Step 3: Synthesis of Phosphonic Acid, [[(S)-2-(4-amino-2-oxo-1(2H)-pyrimidinyl)-1-(hydroxymethyl) ethoxy]methyl]mono[3-(hexadecyloxy)propyl] ester (Compound 1)

Hydrogen chloride gas (11.7 kg, 320.9 mol) was charged to the reactor containing a cooled (−5-5° C.) solution of the crude Compound 3 concentrate in methanol (276.3 kg). The hydrogen chloride gas was introduced below the solvent line in the reaction vessel at a rate where the overall reaction temperature remained between −5-15° C. After completion of the addition, the reaction mixture was maintained at ≤15+/−5° C. for 2 hours before being filtered again. The filtrate was diluted with water (408.4 kg) and the pH of the reaction mixture was adjusted to pH=2.3-2.7 with NaOH (aq.; 29.4 kg of a 50% NaOH (aq.) solution was diluted with 337.6 kg water). The resulting solid was collected via filtration, washed with water (137.6 kg), and re-suspended in acetone (177.1 kg) at 35-45° C. for 1 hour. The solid was dried at 40° C. for 12 hours after a final filtration and acetone wash (2×91.7 kg).

The final step involved heating the crude product to 60-70° C. in methanol (320.8 kg) and then undergoing several slow cooling and filtration cycles as described below:

The solution was polish filtered and then cooled to 60+/−2° C. The reaction was maintained at 60+/−2° C. for about 2 hours. The solution was then cooled to 50+/−2° C. for about 6 hours, and then to 20+/−3° C. for about 2 hours.

The cooled solution was filtered to collect solids from the solution and then washed with methanol (91.7 kg).

The solid material was dissolved in methanol (320.8 kg) at 60-70° C. Once dissolved the reaction mixture was stirred at 60+/−1° C. for an additional 20 minutes before the addition of Compound 1 seed stock (390.0 g). After addition of the seed stock the reaction mixture was stirred for an additional 2 hours at 60° C. The reaction was slowly cooled to 50+/−3° C. over the next 8 hours while stirring. Once 50° C. was reached, the reaction temperature was maintained for an additional 2 hours. A final cooling cycle over 6 hours afforded the reaction mixture at 20+/−3° C., and stirred for an additional 2 hours. The reaction mixture was filtered to collect solids and the collected solids were washed with methanol, and dried at ≤40° C. for 24 hours to yield Compound 1 (41.1 g, 72.4% yield). Purity of the yield was determined by HPLC >99.0%. DSC and XRPD were carried out. The DSC and XRPD data was consistent with a composition comprising the morphic Form II.

Example 2—Pilot Crystallizations

About 5 g of Compound 1 was crystallized from methanol. Effects of different process parameters, including seeding amount (up to 3%), seed temperature (56° C. to 61° C.), process volume (8.5 to 10), starting material (Form II vs. Form H), excess water content (up to 93:7 methanol:water), and agitation rate were evaluated for the crystallization process. Form II was recovered from each of the crystallization attempts, including when the process was not seeded with Form II. Each of the crystallizations utilized a slow cooling process and extended slurry periods.

SEM images were collected on several of the crystallization samples. Most samples contained a combination of agglomerates and very thin plate-shaped particles. The agglomeration observed may be due to secondary nucleation and cementation of fine particles rather than growth on existing particles.

Minor differences were observed in the particles and agglomerates generated from the crystallizations with 0.5% seed and the 3% seed (FIGS. 22 and 23). Particle size analysis of these lots showed the 3% seeded sample had smaller d10, d50, and d90 values than the 0.5% as expected due to the larger number of particles/surface area available for crystal growth. The samples that were crystallized using the hydrate (Form H) as the starting material or contained excess water during the crystallization appeared to generate samples with a lower degree of agglomeration. The higher water content may have changed the solubility or induction time and avoided the secondary nucleation and agglomeration observed in other samples.

The samples prepared with slow agitation still showed significant agglomeration. A seeding step utilizing Form II is performed for control of form. Optimization of seeding step (size, amount, slurry time, etc.) along with cooling profile avoids the secondary nucleation which produces smaller particles, agglomeration, and formation of the undesired Form I. Inclusion of extended slurry times aids in conversion of any Form I that produces to the more stable Form II. Reduction of water content to minimal levels avoids conditions that favors the formation of the hydrate.

Example 3: Methods of Synthesis of Compound 1 Form II e.g., Commercial Synthesis

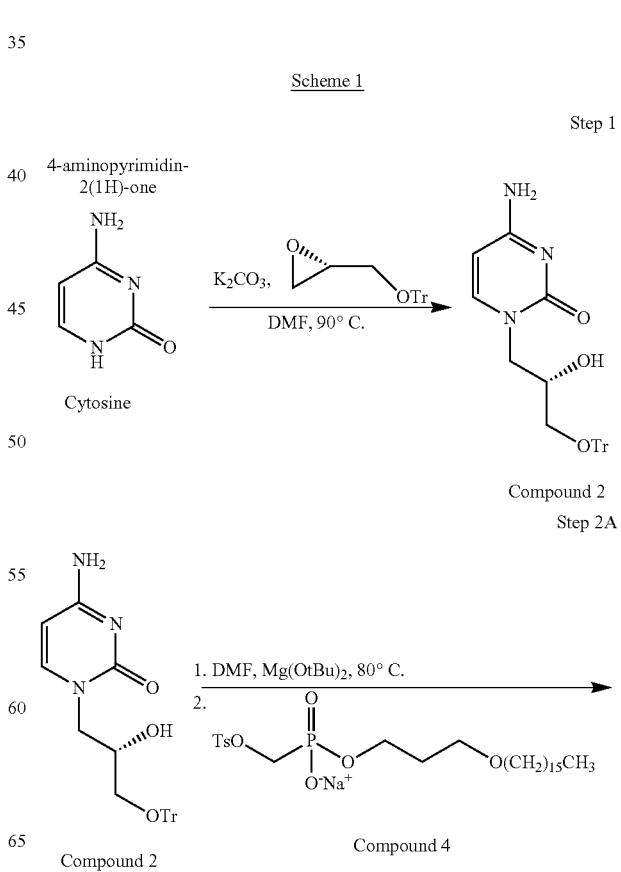

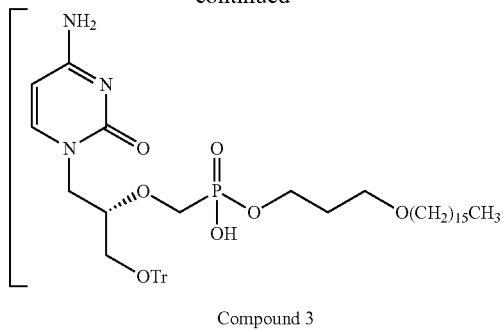

Compound 3

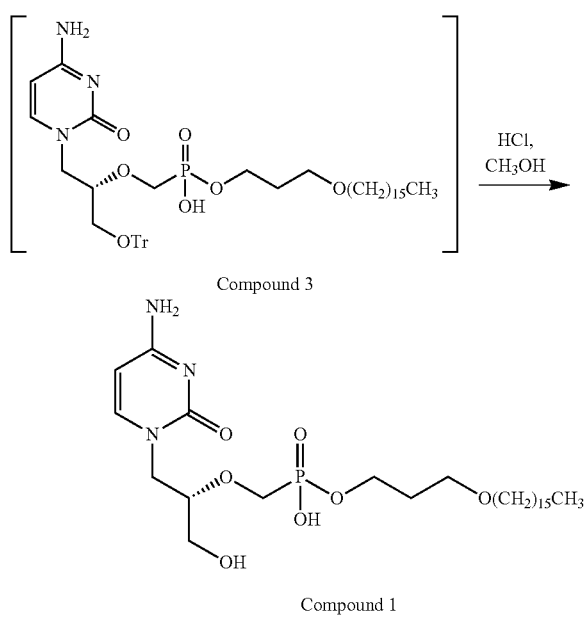

Compound 3

Compound 1

Step 1: Synthesis of (S)-4-Amino-1-(2-hydroxy-3-(trityloxy)propyl)pyrimidin-2(1H)-one (Compound 2)

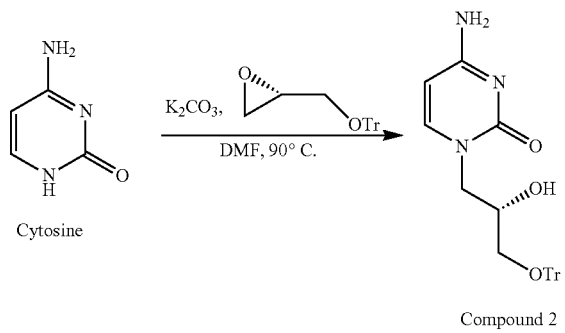

Representative Material Ratios

| | | |
|---|---|---|
| 4-Aminopyrimidin-2(1H)-one (Cytosine) | 50.4 kg (453.7 mol) | 18.0 kg (162.0 mol) |
| (S)-Trityl glycidyl ether | 158.9 kg (502.2 mol) | 56.4 kg (178.2 mol) |
| Potassium Carbonate | 6.6 kg (47.8 mol) | 2.2 kg (16.2 mol) |

| | | |
|---|---|---|
| N,N-dimethylformamide | 203.3 kg | 73.2 kg |
| Toluene | 706.4 kg | 423.7 kg |
| Acetone | 958.7 kg | 340.9 kg |
| Water | 40.1 gal | 90.0 kg |
| Yield | 126.1 kg to 145.5 kg | 45.0 to 52.0 kg |

Under a nitrogen atmosphere at ambient temperature a reactor was charged with cytosine, potassium carbonate, (S)-trityl glycidyl ether, and anhydrous N,N-dimethylformamide. The reaction mixture was heated and maintained at 85 to 95° C. until reaction was complete and then cooled to 60 to 70° C. The reaction mixture was quenched with toluene then cooled to 0° C. and filtered. The wet solids were washed with toluene, acetone, acetone/water and then acetone. The solids were slurried in acetone at approximately 40° C. then filtered, washed with acetone, and dried under vacuum at approximately 40° C. until the product contained less than 0.5% solvent. Typical yield was approximately 65 to 75% of theoretical based on Cytosine.

The process for the preparation of Compound 2 contained five in-process checks to ensure consistent quality of the intermediate: 1. confirm that the reaction is complete by measuring the level of cytosine (≤5%; AUC, HPLC); 2. Measuring the remaining cytosine in the isolated and purified Compound 2 (level of cytosine ≤1%; HPLC, AUC); 3. Measuring the residual solvent in Compound 2 to ensure that it is ≤0.5%; loss on drying; 4. Confirming that there is ≤0.10% bis-trityl glycidyl ether alkylated impurity contained in Compound 2 (AUC, HPLC).

Steps 2A and 2B: Preparation of Phosphonic Acid, [[(S)-2-(4-amino-2-oxo-1(2H)-pyrimidinyl)-1-(hydroxymethyl) ethoxy]methyl]mono[3-(hexadecyloxy)propyl] ester (Compound 1)

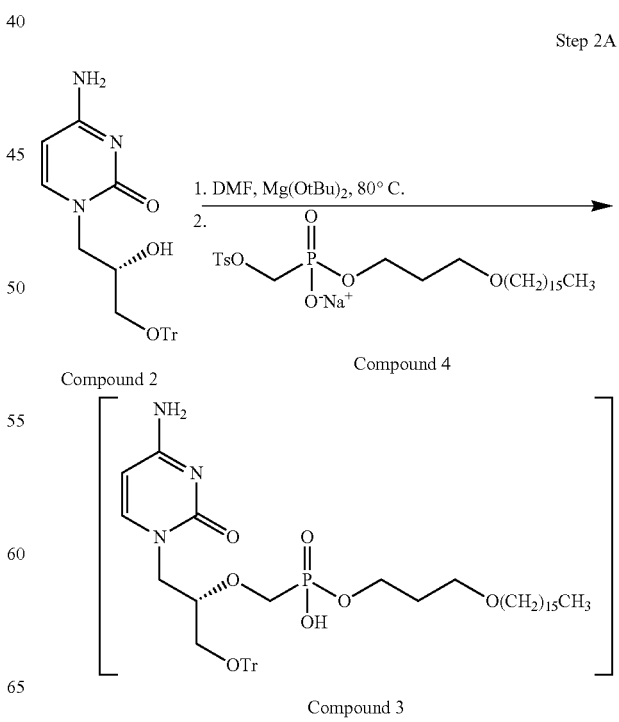

-continued

Step 2B

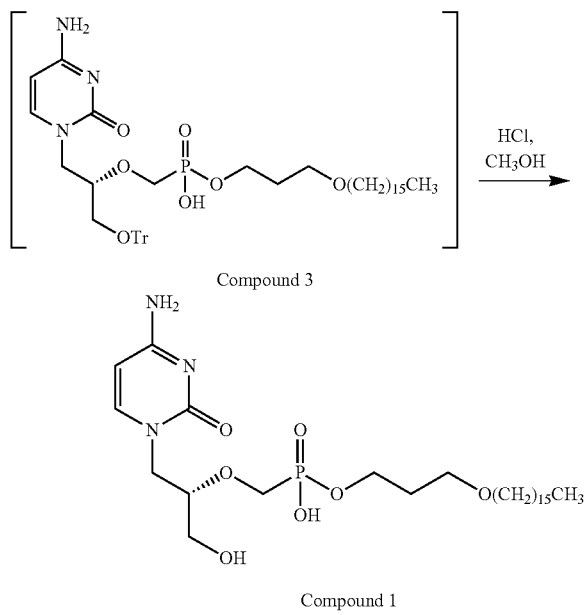

Compound 3

HCl, CH3OH

Compound 1

Representative Material Ratios:

| | | |
|---|---|---|
| (S)-4-Amino-1-(2-hydroxy-3-(trityloxy)propyl)pyrimidin-2(1H)-one (Compound 2) | 120 kg (238.6 moles) | 45.0 kg (105.3 mol) |
| Phosphonic acid, P-[[[(4-methylphenyl)sulfonyl]oxy]methyl]-, mono[3-(hexadecyloxy)propyl]ester, sodium salt(Compound 4) | 151.4 kg (265.3 moles) | 66.1 kg (115.8 mol) |
| Magnesium di-tert-butoxide | 43.3 kg (253.9 moles) | 18.9 kg (110.5 mol) |
| N,N-Dimethylformamide | 309 kg | 273.0 kg |
| Isopropyl Acetate | 824.0 kg | 387.0 kg |
| Hydorchloric Acid | 51.5 kg | 22.8 kg |
| Water (for hydrochloric acid solution) | 177.2 gal | 290.8 kg |
| Sodium Chloride (brine) | 370.8 kg | 161.3 kg |
| Water (for brine solution) | 207.7 gal | 606.3 kg |
| Methanol | 1905 kg | 852 kg |
| Hydrogen chloride gas | 26.8 kg | 11.7 kg |
| Water | 199 kg | 546.0 kg |
| Acetone | 3,121 kg | 537.6 kg |
| Methanol (for recrystallization) | 3,254 kg | 1250 kg |
| Sodium Hydroxide | 103.0 kg | 29.4 kg |
| Water (for sodium hydroxide solution) | | 337.6 kg |
| CMX001 Seed Stock | | 390.0 g |
| Yield | 87.0 kg to 100.5 kg | 38.4 kg to 44.3 kg (68.4 to 79.0 mol) |

Under a nitrogen atmosphere at ambient temperature an anhydrous N,N-dimethylformamide-rinsed (2×) reactor was charged with anhydrous N,N-dimethylformamide, Compound 2, magnesium di-tert-butoxide, and Compound 4. The reaction mixture was heated and maintained at 75 to 85° C. until complete. The reaction mixture was then cooled to between 25 and 35° C., diluted with isopropyl acetate and washed with an aqueous hydrochloric acid solution. The aqueous layer was removed and the organic layer was washed twice with a sodium chloride solution. The organic phase was concentrated and the solvent was switched from isopropyl acetate to methanol via vacuum distillation. The resulting solution of intermediate (Compound 3) in methanol was cooled to −5 to 5° C. Hydrogen chloride gas was charged to the reactor and the reaction was agitated at approximately 15° C. until the reaction was complete. The reaction mixture was then filtered to remove any insoluble material. The mixture was quenched with water and the pH was adjusted to approximately 2.5 with a solution of sodium hydroxide. The resulting solids were filtered and washed with water. The solids were triturated in acetone at approximately 40° C., filtered, washed with acetone, and dried. The solids were recrystallized from methanol, filtered, and washed with methanol. The solids were recrystallized a second time from methanol, filtered, and washed with methanol. The solids were dissolved in methanol and seeded with morphic form II seed stock. The resulting solid was collected through filtration, washed with methanol, dried under vacuum at approximately 40° C. until there was less than or equal to 0.5% residual solvents remaining. Typical yield of compound 1 morphic form II: 65 to 75% of theoretical based on Compound 2.

Step 3: Sample Recrystallization Procedure

Representative Material Ratios

| | | |
|---|---|---|
| 3-(hexadecyloxy)propyl hydrogen ((S)-1-(4-amino-2-oxopyrimidin-1(2H)-yl)-3-hydroxypropan-2-yloxy)methylphosphonate (Compound 1) | 40.0 kg (71.2 moles) | 60 g |
| n-heptane | 253.0 kg | 400 mL |
| Methanol | 487.9 kg | 400 mL + 500 mL |
| Compound 1 seed stock (morphic form II) | 360.0 g | |

Part-1. Reprocess from Methanol:

The solid (Compound 1) obtained from step 2B of was dissolved in refluxing MeOH (450 mL, at around 65° C.) in a 1 L round-bottom flask and the clear solution obtained was held at around 65° C. for 1 h and cooled to around 61° C.

The contents were stirred at 60° C. for 1 h before gradually cooling to 50° C. over an 8 hr period. After holding at 50° C. for 2 hrs, the contents were further cooled from 50° C. to 20° C. over at least 6 hrs (overnight), stirred at 20° C. for at least 2 hrs and filtered.

The solid obtained was washed with and MeOH (2×25 mL) and dried at 45° C. under vacuum. This process was repeated again two more times.

Part-2A. Reprocess from MeOH-Heptane:

To the hot solution of Compound 1 (60 g) dissolved in refluxing MeOH (360 mL, at around 64° C.) in a 1 L 3-neck round bottom flask was slowly added n-heptane (360 mL) by maintaining the internal temp above 50° C. (over 40 min). The contents were held at around 55° C. for 30 min before gradually cooling to 40° C. over 6 h period.

After stirring at 40° C. for 2 h, the contents were gradually cooled from 40° C. to 20° C. over at least 6 h and stirred at 20° C. for at least 2 h.

The solid obtained was filtered and sequentially washed with n-Heptane (2×20 mL) and MeOH (2×20 mL) and dried under vacuum at ≤45° C. for 12 h, affording white solid. The filtrate was concentrated to dryness and gave an off-white solid (2.6 g).

Part-2B. Form Conversion in MeOH (Process is Performed Three Times, and Seeded with Form II Only for the Last Recrystallization):

The solid obtained from Part-2A was dissolved in refluxing MeOH (450 mL, at around 65° C.) in a 1 L RB flask and the clear solution obtained was held at around 65° C. for 1 h and cooled to approximately 61° C. and seeded with Compound 1 (1 g).

The contents were stirred at 60° C. for 1 h before gradually cooling to 50° C. over an 8 hr period. After holding at 50° C. for 2 hrs, the contents were further cooled from 50° C. to 20° C. over at least 6 hrs (overnight), stirred at 20° C. for at least 2 hrs and filtered.

The solid obtained was washed with and MeOH (2×25 mL) and dried at 45° C. under vacuum, affording shiny white crystalline solid (57 g).

Approximate yield: 85 to 95% based on Compound 1.

The process for the preparation of Compound 1 contained four in-process checks to ensure consistent quality of the intermediate: 1. Confirm that reaction is complete by measuring the level of Compound 2 remaining (should be ≤10.0% (AUC, HPLC)); 2. Determine the content of isopropyl acetate (the amount of isopropyl acetate remaining should be ≤5.0% (AUC, GC); 3. Confirm that reaction is complete by measuring the amount of Compound 3 remaining (should be ≤5.0% (AUC, HPLC)); 4. Determine the amount of residual acetone (the amount of residual acetone is LOD≤0.4% (gas chromatography); 5. Ensure the final product is dry with a residual solvent check (LOD≤0.4%).

Example 4: Compound 1 Second Purification Procedure

Materials Used

| | |
|---|---|
| 3-(hexadecyloxy)propyl hydrogen ((S)-1-(4-amino-2-oxopyrimidin-1(2H)-yl)-3-hydroxypropan-2-yloxy)methylphosphonate (CMX001) | 40.0 kg (71.2 mol) |
| n-heptane | 219.0 kg |
| methanol | 521.9 kg |
| CMX001 seed stock (morphic form II) | 360.0 kg |

Procedure:

Under a nitrogen atmosphere a reactor was charged with CMX001 and methanol. The mixture was heated to reflux (~65° C.) and stirred until a clear solution was formed. n-Heptane was added slowly to the reactor over a period of about 40 min while keeping the temperature above 50° C. The temperature was held at about 55° C. for 30 min and then cooled to about 40° C. over a period of 6 hours. The mixture was stirred at about 40° C. for 2 hours, then cooled to 20° C. over a period of 6 hours. The mixture was stirred at 20° C. for 2 hours. The mixture was then filtered, washed with n-heptane and methanol, and dried under vacuum at ≤45° C.

The resulting solids and methanol were charged to a reactor under a nitrogen atmosphere. The mixture was heated to reflux and stirred for at least one hour. The temperature was adjusted to 60±2° C. and CMX001 seed stock (morphic form II) was added to the reactor. The mixture was stirred for at least one hour at 60±2° C. and then cooled to 50±2° C. over at least eight hours. The mixture was stirred at 50±2° C. for at least two hours then cooled to 20±3° C. over at least six hours. The mixture was then stirred at 20±3° C. for two hours, filtered, washed with methanol, and dried at ≤45° C. until dry (when residual n-heptane level is ≤5000 ppm).

The above recrystallization steps are repeated iteratively (e.g., once, twice, three or more times) until the material has reached the desired purity. The material is then milled and packaged.

A 5 g sample thus produced was labelled Sample 3 and was subjected to DSC and XRPD analysis. The results are given in FIGS. 20-26.

Yield is approximately 36.0 kg to 39.2 kg (64.1 to 69.8 moles) of compound 1 (90 to 98% of theoretical).

The process for the preparation of purified Compound 1 contained two in-process checks to ensure quality of the intermediate: 1. Confirm the residual n-heptane is ≤5000 ppm; 2. Confirm that final product is dry (LOD≤0.4%). The residual methanol (≤300 ppm), acetone (≤200 ppm), isopropyl acetate (≤200 ppm), DMF (≤200 ppm), toluene (≤200 ppm), heptanes (≤5000 ppm) and total volatiles other than water (≤6200) were conducted by GC-HS.

Example 5—Characterization of Compound 1 Form II

General

Compound 1 Form II isolated by the methods described in Example 2 was characterized by XRPD. The XRPD pattern was consistent with crystalline material. The crystalline material was indexed to determine if the crystal was composed primarily of a single phase. $^1$H NMR spectroscopy of the crystalline form was consistent with the chemical structure of Compound 1. The DSC thermogram was carried out, which showed a minor endotherm at ~43° C. (peak max) followed by overlapping major endotherms at ~90 and ~95° C. (peak max). A final endotherm was observed with an onset at ~196° C. Hot stage microscopy showed no significant observations prior to flow at ~189° C. other than some potential sublimation observed at ~98° C. Methanol crystallization at a slower cooling profile, but without any stirring also formed Form II. The DSC thermogram of the Form II formed without stirring had a minor endotherm at ~41° C., overlapping endotherms at ~90 and ~95° C. (peak max), and a final endotherm with an onset at ~200° C.

Crystallization

Crystallization experiments were performed using the Mettler Toledo EasyMax™102 with Julabo F26 chiller/circulator. Crystallizations were performed in 100-mL glass reactors with turbidity probe, temperature probe, and overhead stirring. Experiments performed on the EasyMax™ were conducted under non-GMP conditions.

Crystallization pilots using EasyMax were run at ~5 gram scale. In each of the experiments, the starting material was heated to ~65° C. to ensure complete dissolution. Several process parameters were varied in each experiment, however a slow cooling (>9 hours) profile was used in each of the crystallizations. In experiments where seeding was utilized, hand ground seeds of Form II were used. Solids were isolated by vacuum filtration and dried in a vacuum oven between ~40° C. and ~48° C.

Differential Scanning Calorimetry (DSC)

DSC was performed using a TA Instruments Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The method code on the thermogram is an abbreviation for the start and end temperature as well as the heating rate; e.g., −30-250–10 means "from −30° C. to 250° C., at 10° C./min." See, e.g., FIG. 4.

Hot Stage Microscopy (HSM)

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using a 10 or 20 objective with crossed polarizers and a first order red compensator. Images were captured using SPOT software (v. 4.5.9).

Scanning Electron Microscopy (SEM)

SEM was performed using a FEI Quanta 200 scanning electron microscope equipped with an Everhart Thornley (ET) detector. Images were collected and analyzed using xTm (v. 2.01) and XT Docu (v. 3.2) software, respectively. The magnification was verified using a NIST-traceable standard. Each sample was prepared for analysis by placing a small amount on a carbon adhesive tab supported on an aluminum mount. Each sample was then sputter coated with Au/Pd using a Cressington 108auto Sputter Coater at approximately 20 mA and 0.13 mbar (Ar) for 75 seconds. Each sample was observed under high vacuum using a beam voltage of 5.0 kV. The magnification reported on each image was calculated upon the initial data acquisition. The scale bar reported in the lower portion of each image is accurate upon resizing and should be used when making size determinations.

X-Ray Powder Diffraction (XRPD)

XRPD patterns shown in Figures. 1, 2, 10, 12-14, and 16-17 were generated using Pattern Match 2.3.6. XRPD patterns were collected with a PANalytical X'Pert PRO MPD diffractometer either in reflection or transmission geometry. For reflection geometry, the diffractometer was configured using the symmetric Bragg-Brentano geometry and the incident beam of Cu Kα radiation was produced using a long, fine-focus source and a nickel filter. A specimen of the sample was prepared as a thin, circular layer centered on a silicon zero-background substrate. Anti-scatter slits (SS) were used to minimize the background generated by air. In transmission geometry, the diffractometer used an incident beam of Cu radiation produced using an Optix long, fine-focus source. An elliptically graded multilayer mirror was used to focus Cu Kα X-rays through the specimen and onto the detector. A specimen of the sample was sandwiched between 3-μm-thick films and analyzed in transmission geometry. A beam-stop, short anti-scatter extension, and anti-scatter knife edge, were used to minimize the background generated by air. Transmission configuration was used most frequently throughout this study. For either configuration, prior to the analysis, a silicon specimen (NIST SRM 640d) was analyzed to verify the Si 111 peak position. Soller slits for the incident and diffracted beams were used to minimize broadening from axial divergence. Diffraction patterns were collected using a scanning position-sensitive detector (X'Celerator) located 240 mm from the sample and Data Collector software v. 2.2b.

An Anton Paar TTK 450 stage was used to collect in-situ XRPD patterns as a function of temperature. The sample was heated with a resistance heater located directly under the sample holder, and the temperature was monitored with a platinum-100 resistance sensor located in the specimen holder. The heater was powered and controlled by an Anton Paar TCU 100 interfaced with Data Collector.

Figure 21:
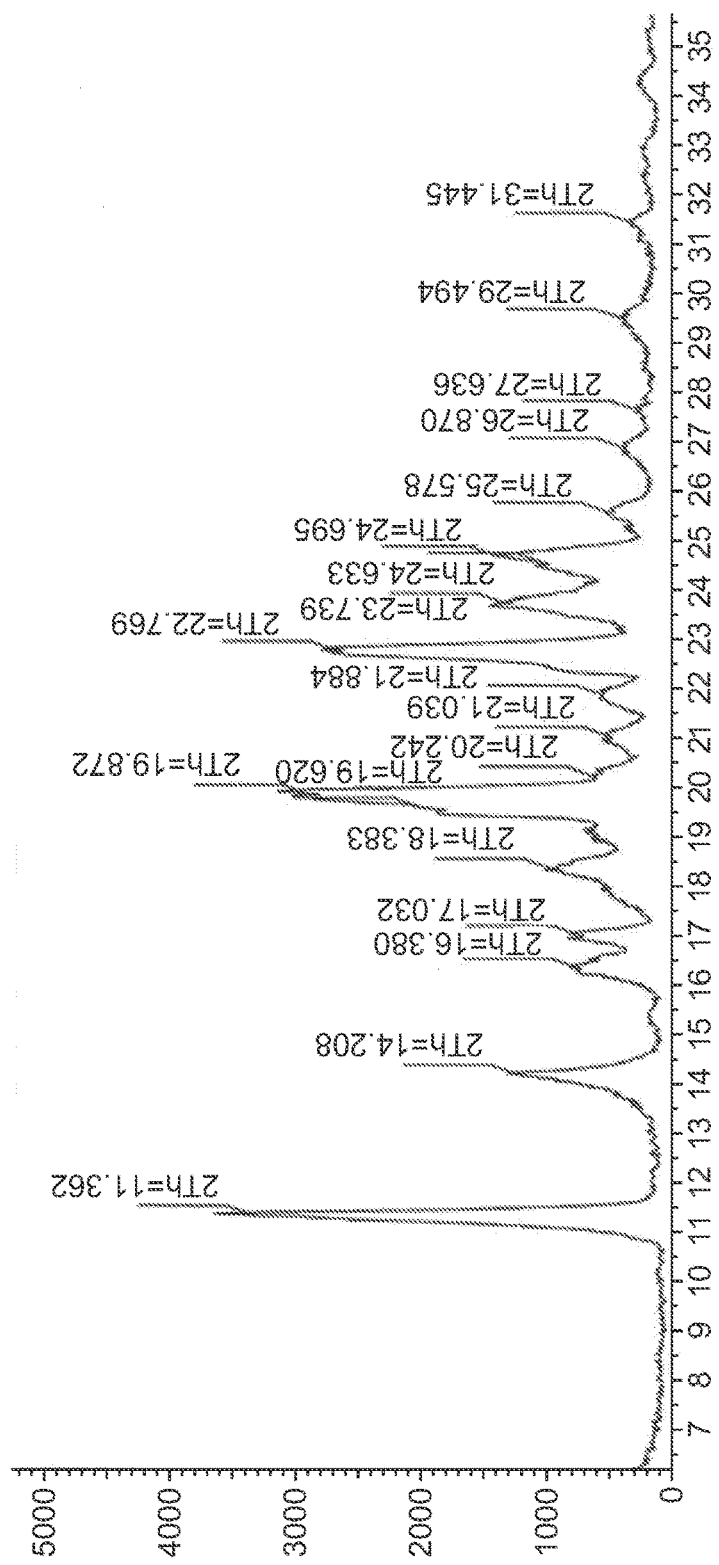
FIG. 21 shows a second XRPD scatter for a sample of Compound 1, Form II (sample 3).
Figure 25:
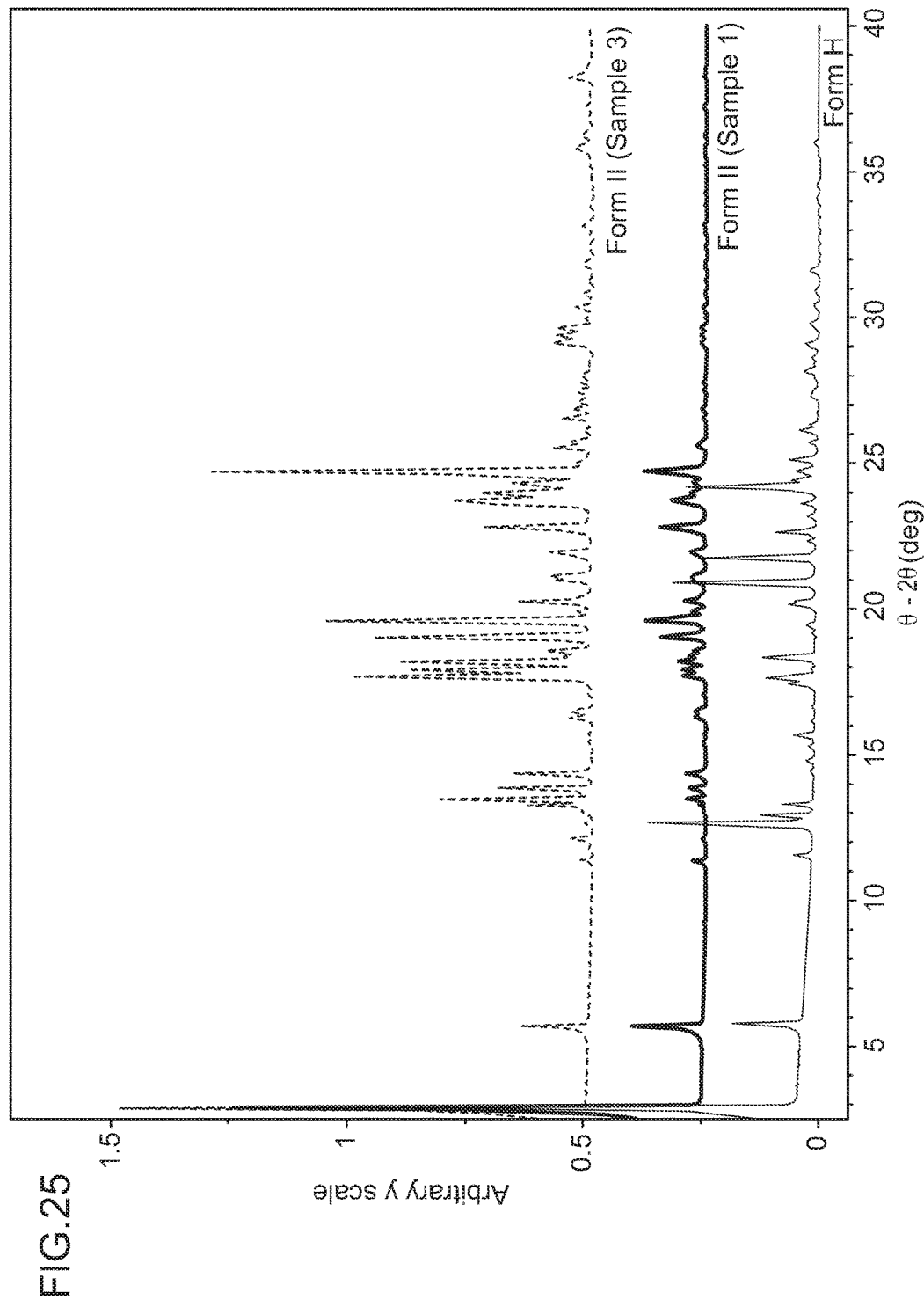
FIG. 25 shows a comparison XRPD overlay of Compound 1, Form II (sample 3); Compound 1, Form II (sample 1); and Compound 1, Form H.
Figure 26:
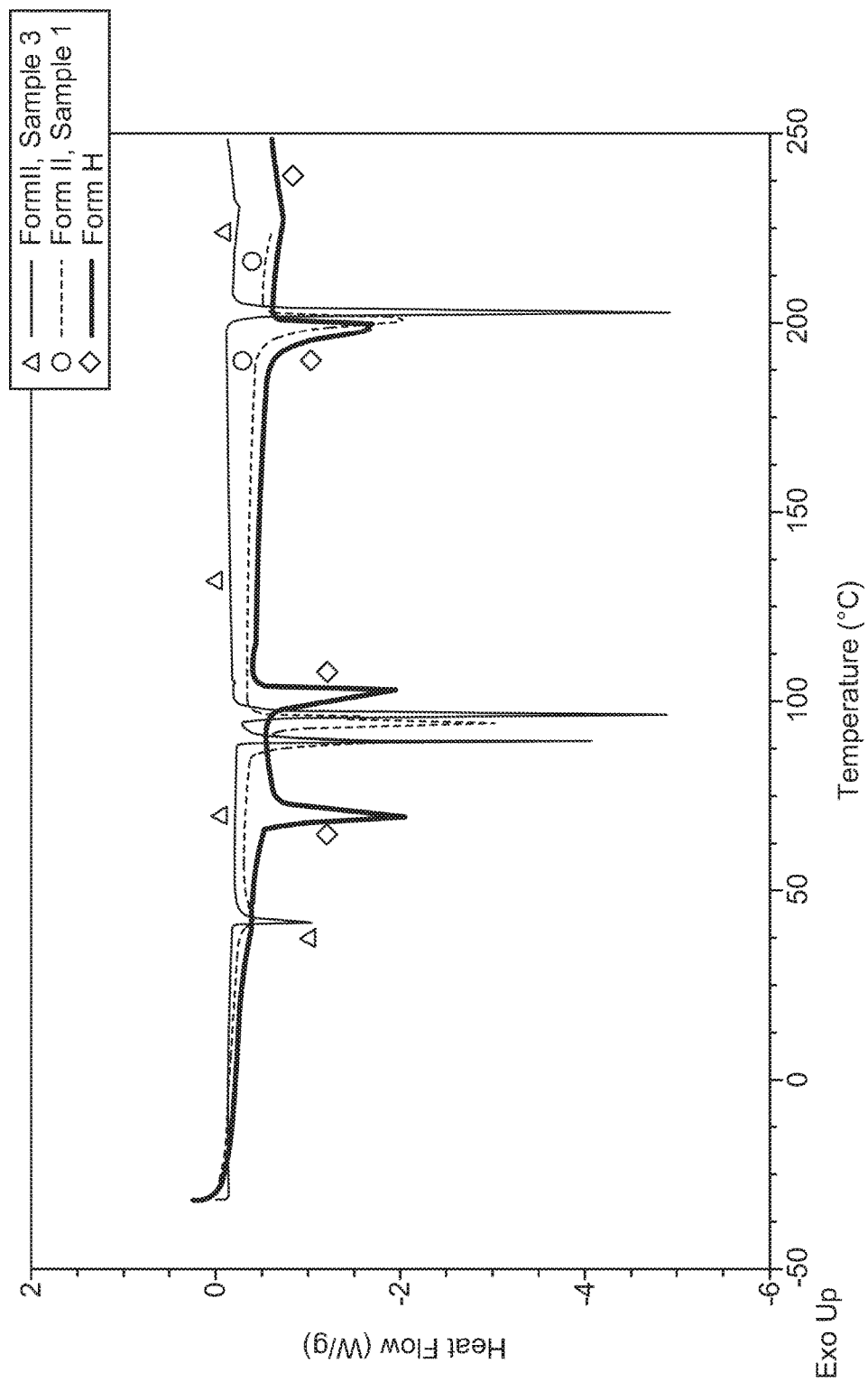
FIG. 26 shows a comparison DSC thermogram overlay of Compound 1 Form II (sample 3); Compound 1, Form II and Compound 1, Form H.

XRPD patterns shown in FIGS. 20, 21, and 25 were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short anti-scatter extension, and an antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. PatternMatch v2.3.6 was used to create FIG. 25.

Computational Techniques

XRPD Indexing

XRPD patterns were indexed using X-Pert High Score Plus (v.2.2.1). Indexing and structure refinement are computational studies which were performed under the "Procedures for SSCI Non-cGMP Activities." Agreement between the allowed peak positions and the observed peaks indicated a consistent unit cell determination. Successful indexing of a pattern indicated that the sample was composed primarily of a single crystalline phase. Space groups consistent with the assigned extinction symbol, unit cell parameters, and derived quantities were tabulated in the respective figures providing the indexing solution for each form. To confirm the tentative indexing solution, the molecular packing motifs within the crystallographic unit cells are determined.

XRPD Peak Identification

Under most circumstances, peaks within the range of up to about 30° 2Θ were selected. Rounding algorithms were used to round each peak to the nearest 0.1° or 0.01° 2Θ, depending upon the instrument used to collect the data and/or the inherent peak resolution. The location of the peaks along the x-axis (°2Θ) in both the figures and the tables were determined using proprietary software and rounded to one or two significant figures after the decimal point. For d-space listings, the wavelength used to calculate d-spacing was 1.541874 Å, a weighted average of the Cu—$K_{\alpha 1}$ and Cu—$K_{\alpha 2}$ wavelengths.

Variability associated with d-spacing estimates was calculated from the USP recommendation, at each d-spacing, and provided in the respective data tables. Per USP guidelines, variable hydrates and solvates may display peak variances greater than 0.2° 2Θ and therefore peak variances of 0.2° 2Θ were not applicable to these materials. For samples with only one XRPD pattern and no other means to evaluate whether the sample provides a good approximation of the powder average, peak tables contain data identified only as "Prominent Peaks." These peaks were a subset of the entire observed peak list. Prominent peaks were selected from observed peaks by identifying preferably non-overlapping, low-angle peaks, with strong intensity.

Particle Size Analysis (PSA)

Particle size data was acquired using a Malvern Instruments Mastersizer 2000 equipped with a Hydro2000 μP dispersion unit. Data was collected and analyzed using Mastersizer 2000 software (v. 5.60) using volume based measurements. NIST-traceable glass beads were used to qualify the instrument.

Particle size analysis and Scanning Electron Microscopy (SEM) were carried out on the isolated crystal Form II. The SEM images showed large agglomerates along with smaller plate-shaped particles for Compound 1 Form II (FIGS. 22-25). Most samples had a bi-modal distribution with a mode of small particles at ~6-10 μm and a larger mode at ~60-160 μm. Sizes of the particles differed depending on the type of sample. Three samples were characterized by SEM and particle size analysis. These included: the starting material; the methanol recrystallized material; and the comilled material from a ~45 kg recrystallization batch.

The starting material contained agglomerates (~100 μm) composed of smaller plates. The particle size distribution for the starting material was bi-modal. The methanol recrystallized sample contained larger primary particles, some agglomeration without cementation and a single particle size mode. The comilled sample was similar to the methanol recrystallized sample but showed a slightly smaller particle distribution suggesting that only minor particle attrition occurred during the milling step. The SEM images also suggested little attrition based on the morphology of the particles.

Example 6—Characterization of Drug Product Samples

Figure 18:
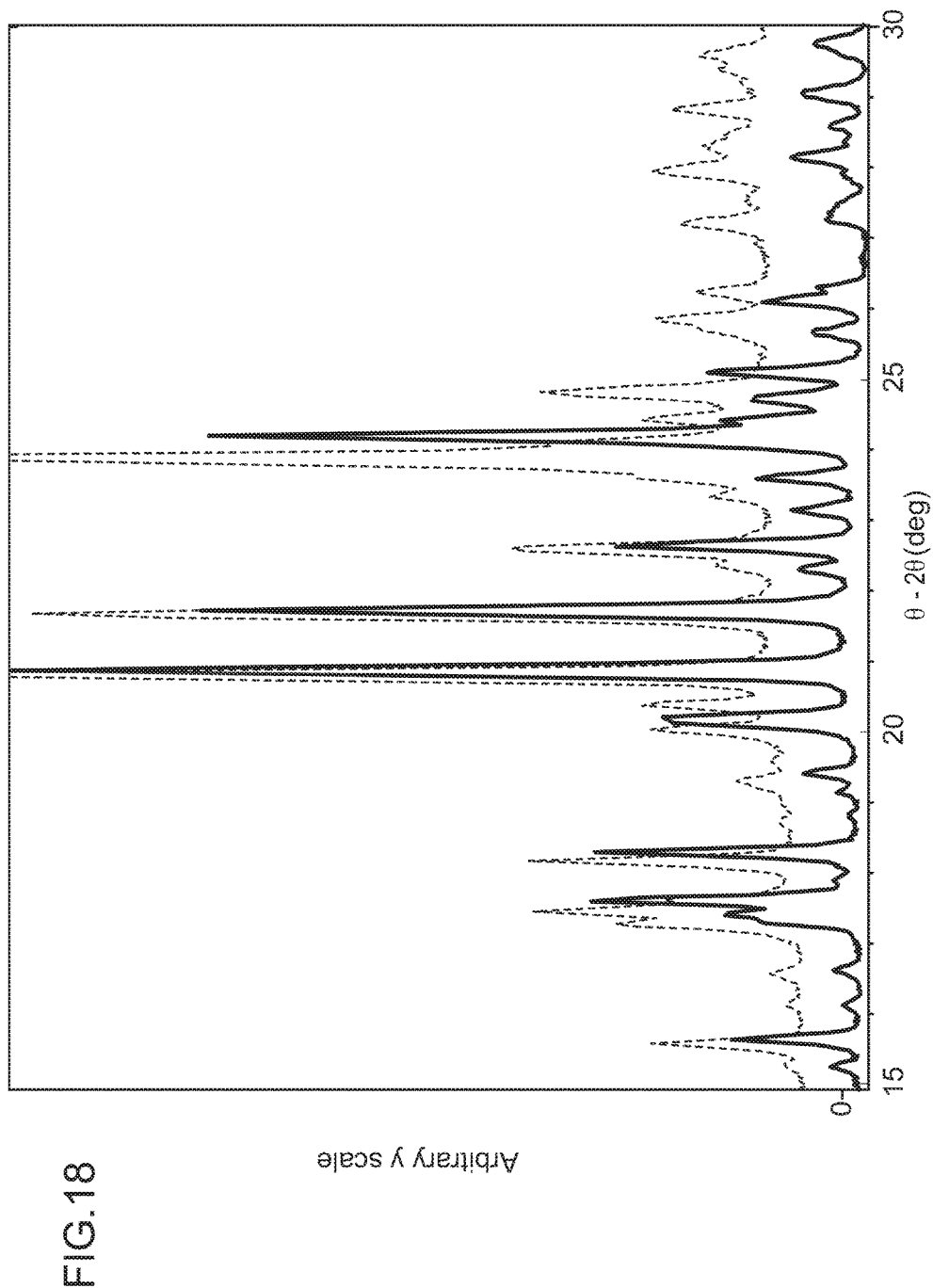
FIG. 18 shows XRPD overlay (~15-30 2-Theta) of two Form H samples of Compound 1 with peak shifting.
Figure 19:
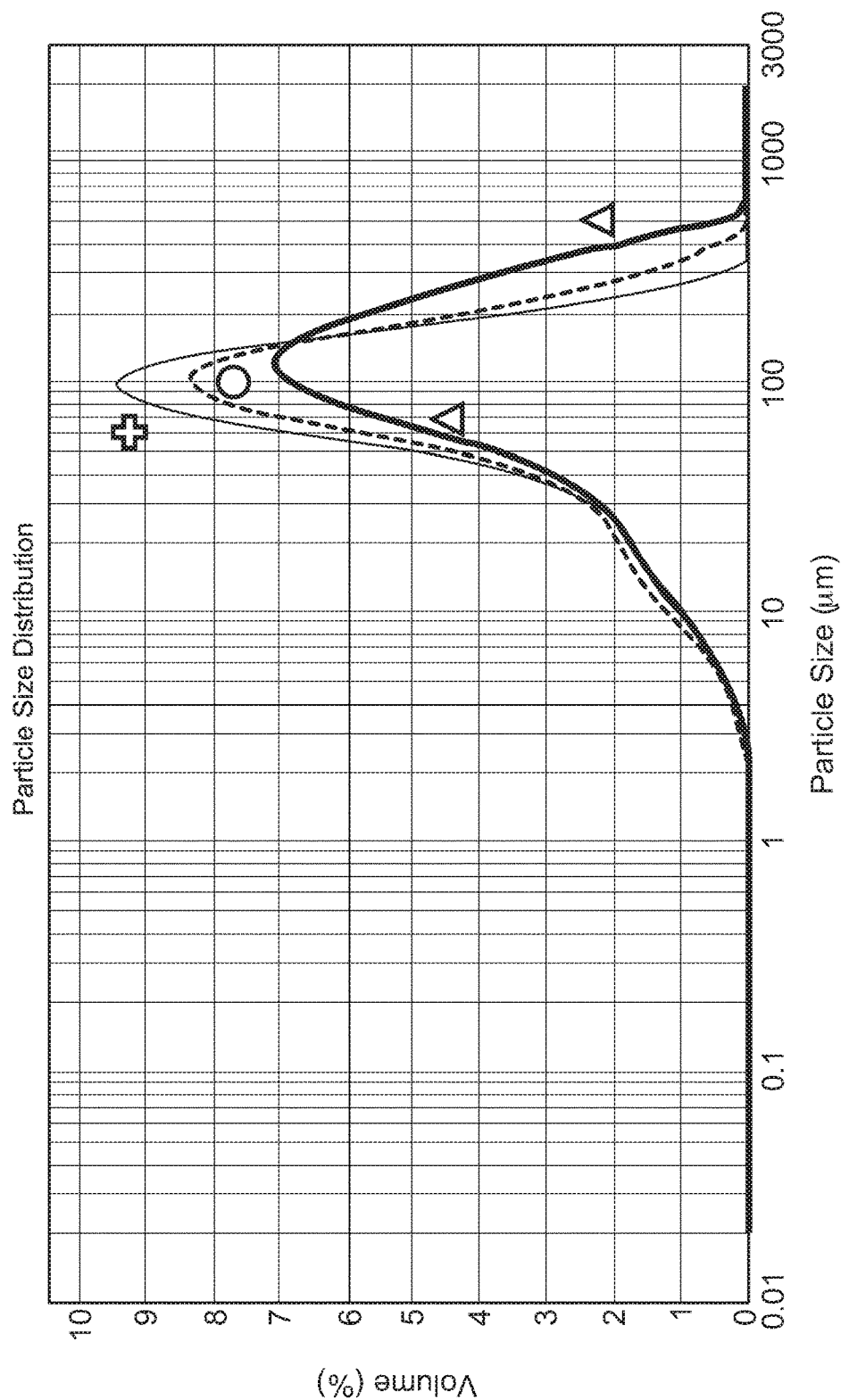
FIG. 19 shows a comparison of particle size distribution overlay of Compound 1 Form II samples produced by recrystallized from methanol and rapid cooling (cross) with samples 3 (circle) and 4 (triangle) produced with seeding and slow cooling.

XRPD and DSC analysis were completed on two samples of Compound 1 tablets. Prior to analysis, the tablets were lightly ground using a mortar and pestle. The two tablet samples showed very similar XRPD patterns (see FIGS. 16 and 17) indicative of crystalline material with diffuse scatter potentially from one or more excipients. Comparison with Form I, Form II, and Form H showed several peaks consistent with Form II in both tablet samples (FIG. 14). The DSC thermograms (FIGS. 18 and 19) for both tablet samples showed overlapping minor endotherms at ~90° C. and ~95° C. (peak max) and a major endotherm with an onset at ~165° C. The two minor endotherms were consistent with endotherms observed for Form II; however Form II also showed a large endotherm at about 196° C. that was not observed in either sample. Compare FIGS. 18 & 19 with FIG. 4.

Example 7—Stable Form Screening of Compound 1 Form II

In order to aid in the design of solid form screening experiments, solubility estimates were completed in various solvent systems using Form II at ambient and elevated temperature. Generally poor solubility was observed in each of the solvents tested. Solubility greater than 5 mg/mL was observed in Trifluoroethanol. Slurries were set up in a variety of solvent systems to determine the stable form and the potential of Compound 1 to form stable solvates. The slurries were prepared using Form II and each was seeded with Form I. Each of the slurries was stirred for about two weeks and most of the slurries were run at room temperature although a few were run at sub-ambient and elevated temperatures (~45° C.). Form II was recovered in each of the anhydrous solvent systems. A few samples did show a minor amount of Form I in Form II likely due to poor conversion kinetics due to limited solubility. Each of the slurries in aqueous solvent systems was found to have converted to the hydrated form, Form H. No evidence of new forms, including a potential methanol solvate, was observed. Interconversion studies starting with a mixture of Form I and Form II were also run in methanol at room temperature and ~45° C. Solids recovered from these experiments were found to be consistent with Form II suggesting Form II is the most stable anhydrous form between room temperature and ~45° C.

Example 8—Methanol Solubility and Metastable Zone

Solubility Determination: Aliquots of test solvents or solvent mixtures were added to weighed samples of Compound 1. Samples were sonicated as needed between additions to facilitate dissolution. Complete dissolution of the test material in each solvent was determined by visual inspection. The solubility was estimated based on the total volume of solvent needed to provide complete dissolution. The actual solubility may be greater than the value calculated due to the incremental addition of solvent and kinetics of dissolution of the material. The solubility is expressed as "less than" if dissolution did not occur during the experiment, or "more than" if dissolution occurred after the addition of the first aliquot. See Table 2 and discussion under "Solubility" section in the "Detailed Description" of the present disclosure.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method of treating a viral infection in a subject in need thereof, the method comprising administering to the subject in need thereof a therapeutically effective amount of a pharmaceutical composition comprising morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester, and a pharmaceutically acceptable carrier.

2. The method of claim 1, wherein the morphic Form II is characterized by an X-ray diffraction pattern including prominent peaks at about 2.81 and about 5.63 degrees 2θ.

3. The method of claim 1, wherein the morphic Form II is characterized by an X-ray diffraction pattern with three or more peaks expressed in degrees 2θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61.

4. The method of claim 1, wherein the subject is an immunodeficient subject.

5. The method of claim 1, wherein the morphic Form II is administered orally.

6. The method of claim 5, wherein the morphic Form II is administered in the form of a tablet or capsule.

7. The method of claim 1, wherein the morphic Form II is administered at a dose of about 200 mg once a week.

8. The method of claim 1, wherein the morphic Form II has a purity of at least 91%.

9. The method of claim 1, wherein the viral infection is cytomegalovirus infection.

10. The method of claim 1, wherein the viral infection is BK virus infection.

11. The method of claim 1, wherein the subject is a pre-organ or pre-tissue transplantation subject.

12. The method of claim 1, wherein the subject is a post-organ or post-tissue transplantation subject.

13. The method of claim 1, wherein the viral infection is resistant to valganciclovir hydrochloride or ganciclovir.

14. The method of claim 1, wherein the subject exhibits side effects to valganciclovir hydrochloride or ganciclovir.

15. The method of claim 1, wherein the subject is a stem cell transplant patient and there is a risk for bone marrow toxicity from ganciclovir in the subject.

16. A method of preventing a viral infection in a subject in need thereof, the method comprising administering to the subject in need thereof a pharmaceutical composition comprising a therapeutically effective amount of morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester, and a pharmaceutically acceptable carrier.

17. The method of claim 16, wherein the morphic Form II is characterized by an X-ray diffraction pattern including prominent peaks at about 2.81 and about 5.63 degrees 2θ.

18. The method of claim 16, wherein the morphic Form II is characterized by an X-ray diffraction pattern with three or more peaks expressed in degrees 2θ (±0.2) selected from 2.81, 5.63, 11.30, 12.05, 13.22, 13.45, 13.81, 14.32, 14.92, 15.64, 16.25, 16.41, 17.00, 17.67, 17.87, 18.15, 18.35, 18.50, 19.00, 19.57, 19.85, 20.22, 20.96, 21.06, 21.89, 22.76, 23.70, 23.95, 24.32, 24.70, 25.54, 26.12, 26.52, 26.81, 27.07, 27.48, 27.71, 29.11, 29.36, and 29.61.

19. The method of claim 16, wherein the subject is an immunodeficient subject.

20. The method of claim 16, wherein the morphic Form II is administered orally.

21. The method of claim 20, wherein the morphic Form II is administered in the form of a tablet or capsule.

22. The method of claim 16, wherein the morphic Form II is administered at a dose of about 200 mg once a week.

23. The method of claim 16, wherein the morphic Form II has a purity of at least 91%.

24. The method of claim 16, wherein the viral infection is cytomegalovirus infection.

25. The method of claim 16, wherein the viral infection is BK virus infection.

26. The method of claim 16, wherein the morphic Form II is administered prior to the onset of the viral infection.

27. The method of claim 16, wherein the subject is a pre-organ or pre-tissue transplantation subject.

28. The method of claim 16, wherein the subject is a post-organ or post-tissue transplantation subject.

29. The method of claim 16, wherein the subject exhibits side effects to valganciclovir hydrochloride or ganciclovir.

30. The method of claim 16, wherein the subject is a stem cell transplant patient and there is a risk for bone marrow toxicity from ganciclovir in the subject.

31. A pharmaceutical composition comprising:
(i) a morphic Form II of phosphonic acid, [[(S)-2-(4-amino-2-oxo-1(2H)-pyrimidinyl)-1-(hydroxymethyl) ethoxy]methyl]mono[3-(hexadecyloxy)propyl] ester characterized by an X-ray diffraction pattern including prominent peaks at about 2.81 and about 5.63 degrees 2θ; and
(ii) a pharmaceutically acceptable carrier.

* * * * *